(12) United States Patent
Suh et al.

(10) Patent No.: US 11,953,502 B2
(45) Date of Patent: Apr. 9, 2024

(54) THIOREDOXIN 1 EPITOPE, ENCODING NUCLEIC ACID AND METHODS OF BINDING A MONOCLONAL ANTIBODY

(71) Applicant: E&S HEALTHCARE CO., LTD., Daejeon (KR)

(72) Inventors: Kyong Hoon Suh, Daejeon (KR); Dae Joong Kim, Seoul (KR); Young Kim, Cheongju-si (KR); Mi Kyung Kim, Daejeon (KR); Jong Hwan Jung, Daejeon (KR); Ki Se Lee, Sejong (KR)

(73) Assignee: E&S HEALTHCARE CO., LTD., Daejeon (KR)

( * ) Notice: Subject to any disclaimer, the term of this patent is extended or adjusted under 35 U.S.C. 154(b) by 595 days.

(21) Appl. No.: 16/755,035

(22) PCT Filed: Oct. 12, 2018

(86) PCT No.: PCT/KR2018/012069
§ 371 (c)(1),
(2) Date: Apr. 9, 2020

(87) PCT Pub. No.: WO2019/074333
PCT Pub. Date: Apr. 18, 2019

(65) Prior Publication Data
US 2020/0309778 A1    Oct. 1, 2020

(30) Foreign Application Priority Data

Oct. 12, 2017 (KR) .................. 10-2017-0132536

(51) Int. Cl.
| | | |
|---|---|---|
| C07K 7/08 | (2006.01) | |
| C07K 7/00 | (2006.01) | |
| C07K 7/06 | (2006.01) | |
| C07K 14/00 | (2006.01) | |
| C07K 16/40 | (2006.01) | |
| G01N 33/543 | (2006.01) | |
| G01N 33/574 | (2006.01) | |
| G01N 33/577 | (2006.01) | |
| G01N 33/58 | (2006.01) | |

(52) U.S. Cl.
CPC ......... *G01N 33/57415* (2013.01); *C07K 7/08* (2013.01); *C07K 16/40* (2013.01); *G01N 33/54393* (2013.01); *G01N 33/577* (2013.01); *G01N 33/581* (2013.01); *C07K 7/00* (2013.01); *C07K 7/06* (2013.01); *C07K 14/00* (2013.01); *C07K 2317/21* (2013.01); *C07K 2317/24* (2013.01); *C07K 2317/34* (2013.01); *C07K 2317/54* (2013.01); *C07K 2317/55* (2013.01); *C07K 2317/565* (2013.01); *C07K 2317/622* (2013.01)

(58) Field of Classification Search
CPC ... C07K 7/00; C07K 7/06; C07K 7/08; C07K 14/00; C07K 2317/34; C07K 2317/365
See application file for complete search history.

(56) References Cited

U.S. PATENT DOCUMENTS

| 8,512,963 B2 * | 8/2013 | Graham ............. G01N 33/5735 435/7.1 |
|---|---|---|
| 2002/0102654 A1 | 8/2002 | Tang et al. |
| 2011/0143379 A1 | 6/2011 | Graham et al. |
| 2012/0289431 A1 | 11/2012 | Kim |

FOREIGN PATENT DOCUMENTS

| EP | 2410336 | 1/2012 |
|---|---|---|
| EP | 3708575 | 9/2020 |
| JP | 06261783 | 9/1994 |
| KR | 10-2005-0114268 B1 | 12/2005 |
| KR | 20100104110 | 9/2010 |
| KR | 101058230 | 8/2011 |
| RU | 2344831 | 1/2009 |
| WO | WO2005/117930 | 12/2005 |

(Continued)

OTHER PUBLICATIONS

Uniparc—UPI0000DFC16 (https://www.uniprot.org/uniparc/UPIOOOOD9FC_16) web capture Oct. 9, 2021.
International Search Report and Written Opinion issed in Application No. PCT/KR2018/012069, dated May 17, 2019.
NCBI, GenBank; AAA16583.1, "Immunoglobulin Heavy Chain, Partial [Mus musculus]", Mar. 9, 1991.
NCBI, GenBank; AAB05154.1, "Ig 6D12.F1 Light Chain, Partial [Mus musculus]", Sep. 14, 2001.
NCBI, GenBank; AAF88053.1, "Immunoglobulin Light Chain Variable Region, Partial [Mus musculus]", Jul. 26, 2016.
NCBI, GenBank; BAU30829.1, "Immunoglobulin Heavy Chain, Partial [Mus musculus]", Jan. 14, 2016.

(Continued)

*Primary Examiner* — Robert S Landsman
(74) *Attorney, Agent, or Firm* — NORTON ROSE FULBRIGHT US LLP

(57) ABSTRACT

The present invention relates to an epitope of a thioredoxin-1 (Trx1) antigen and a use thereof, and more particularly, to the epitope, and an antibody or an antigen-binding fragment binding thereto. The epitope region of the human Trx1 antigen confirmed in the present invention may be effectively used in the development of an improved antibody to enhance the binding affinity of an anti-Trx1 antibody. In addition, the improved antibody of the present invention is effective in improvement of performance of a breast cancer diagnosis kit due to excellent binding affinity for Trx1 and very high sensitivity and specificity, compared to a conventional anti-Trx1 antibody. Further, the accuracy and reliability of breast cancer diagnosis may significantly increase because exceptionally high sensitivity and specificity are exhibited by detecting the monoclonal antibody of the present invention, which specifically binds to Trx1, rather than detecting CA15-3, another conventional breast cancer diagnostic biomarker.

11 Claims, 35 Drawing Sheets
Specification includes a Sequence Listing.

(56) References Cited

FOREIGN PATENT DOCUMENTS

WO    WO 2010/107158    9/2010
WO    WO2018/052153    3/2018

OTHER PUBLICATIONS

NCBI, PDB: 2IIY_A, "Chain A, Crystal Structure of S-Nitroso Thioredoxin", Oct. 10, 2012.
Park et al., "Thioredoxin 1 as a serum marker for breast cancer and its use in combination with CEA or CA15-3 for improving the sensitivity of breast cancer diagnoses" *BMC Research Notes* 2014, 7(7), 12 pages.
Weichsel et al., "Buried S-Nitrosocysteine Revealed in Crystal Structures of Human Thioredoxin" *Biochemistry* 2007, 46, 1219-1227.
Schellens, et al. "Comprehensive analysis of the naturally processed peptide repertoire: differences between HLA-A and B in the immunopeptidome", *PLOS One*, 2015.
Office Action issued in corresponding Russian Application No. 2022120507/10, dated Mar. 15, 2023.
Office Action issued in corresponding UAE Application No. P6000534/2020, dated Nov. 12, 2023.

* cited by examiner

(a)

SEQUENCE: >Unnamed-1

```
  1  QIVLTQSPAIMSASPGEKVTMTCSASSRLSYMYWYQQKPGTSPKRWIYDTSKLASGVPARFSGSGSGTSYSLTISTMEAE
 81  DAATYYCHQRSSYPTPGAGTKLEIKRADAAPTVSIFPPSSEQLTSGGASVVCFLNNFYPKDINVKWKIDGSERQNGVLNS
161  WTDQDSKDSTYSMSSTLTLTKDEYERHNSYTCEATHKTSTSPIVKSFNRNEC
```
(SEQ ID NO: 186)

COMPOSITION:

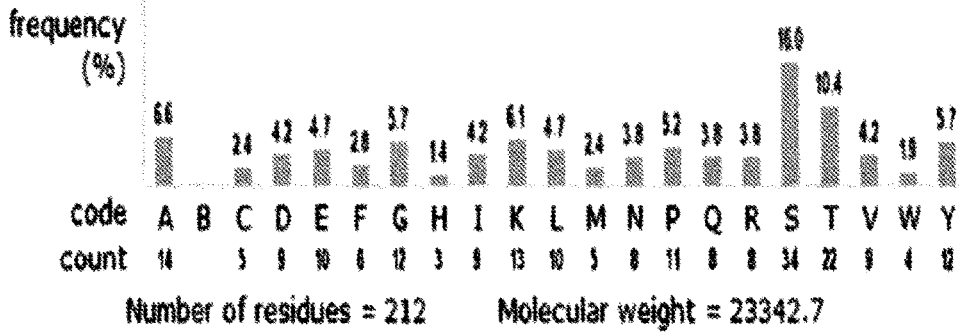

Number of residues = 212    Molecular weight = 23342.7

(b)

SEQUENCE: >Unnamed-1

```
  1  EVQLQQSGAELVKPGASVKLSCTASGFNIKDTFMHWVKQRPEQGLEWIGRIDPANGNTKYDPKFQGKATITADTSSNTAY
 81  LQLSSLTSEDTAVYYCALLQYSAMDYWGQGTSVTVSSAKTTPPSVYPLAPGCGDTTGSSVTLGCLVKGYFPESVTVTWNS
161  GSLSSSVHTFPALLQSGLYTMSSSVTVPSSTWPSQTVTCSVAHPASSTTVDKKLEPSGPISTINPCPPCKECHKCPAPNL
241  EGGPSVFIFPPNIKDVLMISLSPKVTCVVVDVSEDDPDVQISWFVNNVEVHTAQTQTHREDYNSTIRVVSTLPIQHQDWM
321  SGKEFKCKVNNKDLPSPIERTISKIKGLVRAPQVYILPPPAEQLSRKDVSLTCLVVGFNPGDISVEWTSNGHTEENYKDT
401  APVLDSDGSYFIYSKLNMKTSKWEKTDSFSCNVRHEGLKNYYLKKTISRSPG
```
(SEQ ID NO: 187)

COMPOSITION:

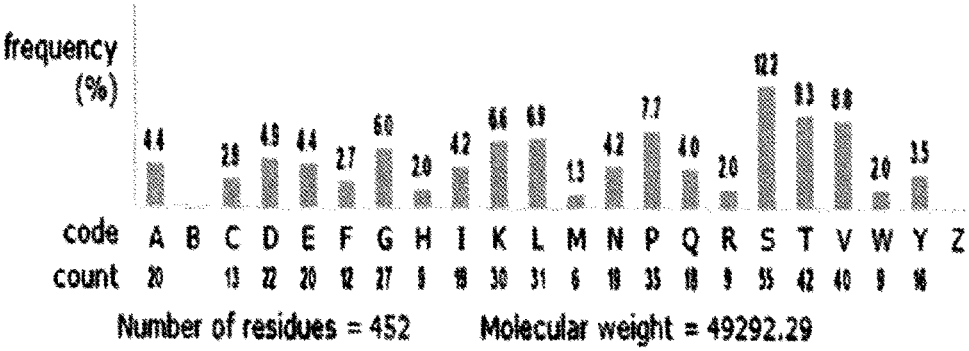

Number of residues = 452    Molecular weight = 49292.29

SEQUENCE: >Unnamed-1

1 DVLMTQTPLSLPVSLGDQASISCRSSQSIVHSNGNTYLEWYLQKPGQSPKLLIYKVSNRFSGVPDRFSGSGSGTDFTLKI
81 SRVEAEDLGVYYCFQGSHVPYTFGGGTKLEIKRADAAPTVSIFPPSSPEQLTSGGASVVCFLNNFYPKDINVKWKIDGSER
161 QNGVLNSWTDQDSKDSTYSMSSTLTLTKDEYERHNSYTCEATHKTSTSPIVKSFNRNEC (SEQ ID NO: 188)

COMPOSITION:

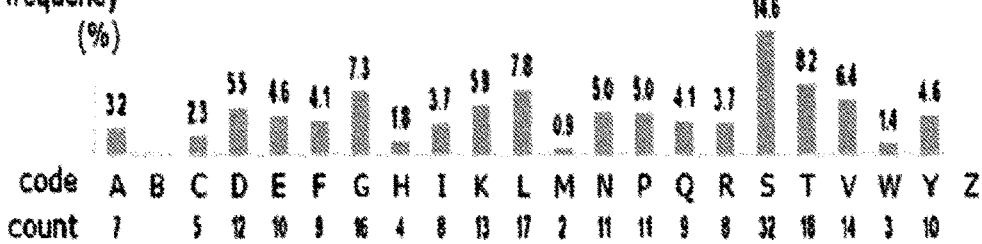

Number of residues = 219    Molecular weight = 24157.65

(b)

SEQUENCE: >Unnamed-1

1 QVQLQQSGAELARPGASVKMSCKASGYTFTSYTMHWVKQRPGQGLEWIGYINPTSDYTNYNQKFKDKATLTADKSSSTAY
81 MQLSSLTSEDSAVYFCASEGGPLYYFDYWGQGTTLTVSSAKTTPPSVYPLAPGSAAQTNSMVTLGCLVKGYFPEPVTVTW
161 NSGSLSSGVHTFPAVLQSDLYTLSSSVTVPSSTWPSETVTCNVAHPASSTKVDKKIVPRDCGCKPCICTVPEVSSVFIFP
241 PKPKDVLTITLTPKVTCVVVDISKDDPEVQFSWFVDDVEVHTAQTQPREEQFNSTFRSVSELPIMHQDWLNGKEFKCRVN
321 SAAFPAPIEKTISKTKGRPKAPQVYTIPPPKEQMAKDKVSLTCMITDFFPEDITVEWQWNGQPAENYKNTQPIMDTDGSY
401 FVYSKLNVQKSNWEAGNTFTCSVLHEGLHNHHTEKSLSHSPG (SEQ ID NO: 189)

COMPOSITION:

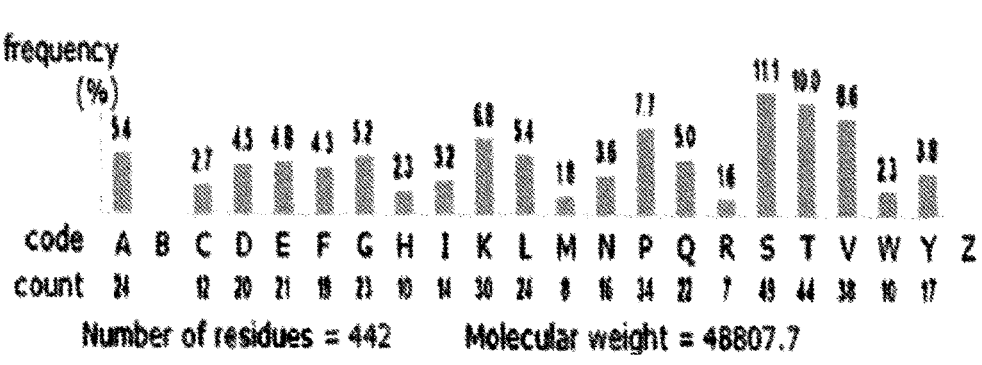

Number of residues = 442    Molecular weight = 48807.7

FIG. 3

PREDICTED: thioredoxin-like [Chrysochloris asiatica]
Sequence ID: XP_006863063.1 Length: 105 Number of Matches: 1

Query: human TRX1
Sbject: *Chrysochloris asiatica* TRX1

Range 1: 2 to 104 SignPart Graphics

| Score | Expect | Method | Identities | Positives | Gaps |
|---|---|---|---|---|---|
| 176 bits(446) | 1e-55 | Compositional matrix adjust | 84/103(82%) | 92/103(89%) | 0/103(0%) |

Match  Previous Match

```
Query  1   VKQIESKTAFQEALDAAGDKLVVVDFSATWCGPCKMIKPFFHSLSEKYSNVIFLEVDVDD  60
           VK+IE K  F  AL +AGDKLVVVDFSATWCGPCKMIKPF+HSLSEK+ N++FLEVDVDD
Sbjct  2   VKEIEGKEDFHAALSSAGDKLVVVDFSATWCGPCKMIKPFYHSLSEKFGNMVFLEVDVDD  61

Query  61  CQDVASECEVKCMPTFQFFKKGQKVGEFSGANKEKLEATINEL  103
           CQDVASECEVKCM TFQF+KK +KVGEFSG NKEKLEA IMEL
Sbjct  62  CQDVASECEVKCMITFQFYKKREKVGEFSGVNKEKLEAIINEL  104
```

Translation of Chrysochloris asiatica  1  VKEIEGKEDFHAALSSAGDKLVVVDFSATWCGPCKMIKPFYHSLSEKFGNMVFLEVDVDDCQDVASECEVKCMITFQFYKKREKVGEFSGVNKEKLEATINELC (SEQ ID NO: 205)
Translation of human TRX  1  VKQIESKTAFQEALDAAGDKLVVVDFSATWCGPCKMIKPFFHSLSEKYSNVIFLEVDVDDCQDVASECEVKCMPTFQFFKKGQKVGEFSGANKEKLEATINELV (SEQ ID NO: 206)

Human    VKEIEGKEDFHAALSSAGDKLVVVDFSATWCGPCKMIKPFYHSLSEKFGNMVFLEVDVDDCQDVASECEVKCMITFQFYKKREKVGEFSGVNKEKLEATINELC (SEQ ID NO: 205)

Asiatica VKQIESKTAFQEALDAAGDKLVVVDFSATWCGPCKMIKPFFHSLSEKYSNVIFLEVDVDDCQDVASECEVKCMPTFQFFKKGQKVGEFSGANKEKLEATINELV (SEQ ID NO: 206)

M1 ........ VKQIESKT[IEGKED]QEALDAAGDKLVVVDFSATWCGPCKMIKPFFHSLSEKYSNVIFLEVDVDDCQDVASECEVKCMPTFQFFKKGQKVGEFSGANKEKLEATINELV (SEQ ID NO: 207)
M2 ........ VKQIESKTA[HAALSS]AGDKLVVVDFSATWCGPCKMIKPFFHSLSEKYSNVIFLEVDVDDCQDVASECEVKCMPTFQFFKKGQKVGEFSGANKEKLEATINELV (SEQ ID NO: 208)
M3 ........ VKQIESKTAFQEALDAAGDKLVVVDFSATWCGPCKMIKP[FY]HSLSEKYSNVIFLEVDVDDCQDVASECEVKCMPTFQFFKKGQKVGEFSGANKEKLEATINELV (SEQ ID NO: 209)
M4 ........ VKQIESKTAFQEALDAAGDKLVVVDFSATWCGPCKMIKPFFHSLSEK[YSNVIF]LEVDVDDCQDVASECEVKCMPTFQFFKKGQKVGEFSGANKEKLEATINELV (SEQ ID NO: 210)
M5 ........ VKQIESKTAFQEALDAAGDKLVVVDFSATWCGPCKMIKPFFHSLSE[FGNM]LEVDVDDCQDVASECEVKCMPTFQFFKKGQKVGEFSGANKEKLEATINELV (SEQ ID NO: 211)
M6 ........ VKQIESKTAFQEALDAAGDKLVVVDFSATWCGPCKMIKPFFHSLSEKYSNVIFLEVDVDDCQDVASECEVKCM[IT]FQFFKKGQKVGEFSGANKEKLEATINELV (SEQ ID NO: 212)
M7 ........ VKQIESKTAFQEALDAAGDKLVVVDFSATWCGPCKMIKPFFHSLSEKYSNVIFLEVDVDDCQDVASECEVKCMPTFQ[YKKRE]VGEFSGANKEKLEATINELV (SEQ ID NO: 213)
M8 ........ VKQIESKTAFQEALDAAGDKLVVVDFSATWCGPCKMIKPFFHSLSEKYSNVIFLEVDVDDCQDVASECEVKCMPTFQFFKKGQKVGEFSG[VNKEKLEATINELC] (SEQ ID NO: 214)

| Lane | Fragment | Lane | Fragment |
|---|---|---|---|
| 1 | TRX1-M1-F1 | 9 | TRX1-M5-F1 |
| 2 | TRX1-M1-F2 | 10 | TRX1-M5-F2 |
| 3 | TRX1-M2-F1 | 11 | TRX1-M6-F1 |
| 4 | TRX1-M2-F2 | 12 | TRX1-M6-F2 |
| 5 | TRX1-M3-F1 | 13 | TRX1-M7-F1 |
| 6 | TRX1-M3-F2 | 14 | TRX1-M7-F2 |
| 7 | TRX1-M4-F1 | 15 | TRX1-M8-F1 |
| 8 | TRX1-M4-F2 | 16 | TRX1-M8-F2 |

| Antibody | W | M1 | M2 | M3 | M4 | M5 | M6 | M7 | M8 | C |
|---|---|---|---|---|---|---|---|---|---|---|
| | | | | TRX N-His W(wild) & M(mutants) & C (asiatica TRX N-his) | | | | | | |
| Ab1 hIgG1 | 2.5023 | 2.3006 | 2.3268 | 2.2046 | 0.4352 | 2.4078 | 2.1154 | 2.2253 | 2.2148 | 0.045 |
| Ab2 mIgG1 | 1.1369 | 0.0424 | 0.094 | 0.824 | 0.1813 | 0.4921 | 0.6594 | 0.7608 | 0.999 | 0.048 |

FIG. 18C

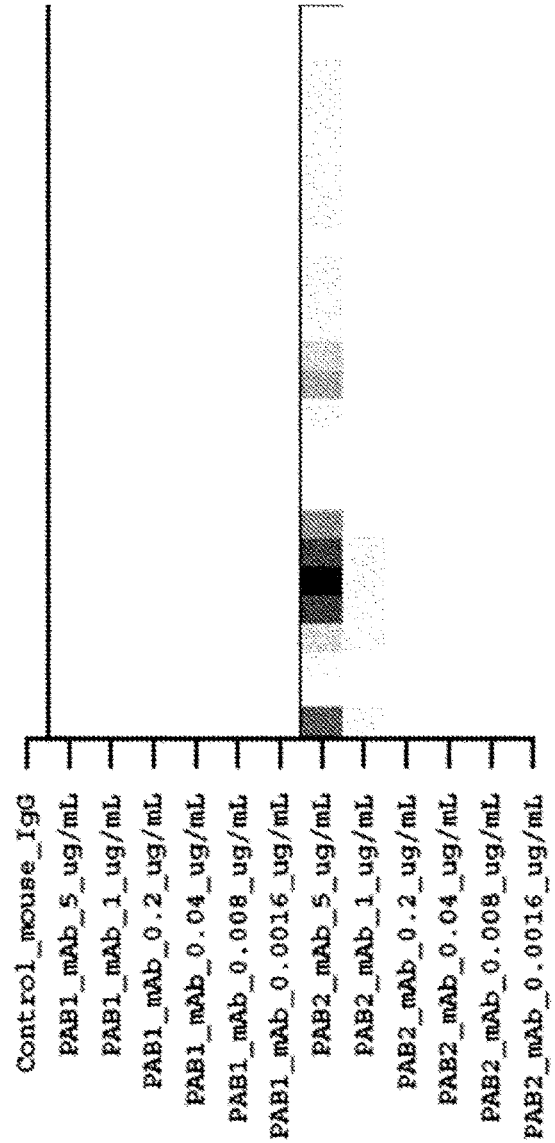

| | | |
|---|---|---|
| TAFQEALDAAGDKLV | - Peptide_026 | (SEQ ID NO: 89) |
| AFQEALDAAGDKLVV | - Peptide_027 | (SEQ ID NO: 90) |
| FQEALDAAGDKLVVV | - Peptide_028 | (SEQ ID NO: 91) |
| QEALDAAGDKLVVVD | - Peptide_029 | (SEQ ID NO: 92) |
| EALDAAGDKLVVVDF | - Peptide_030 | (SEQ ID NO: 93) |
| ALDAAGDKLVVVDFS | - Peptide_031 | (SEQ ID NO: 94) |
| LDAAGDKLVVVDFSA | - Peptide_032 | (SEQ ID NO: 95) |
| DAAGDKLVVVDFSAT | - Peptide_033 | (SEQ ID NO: 96) |
| AAGDKLVVVDFSATW | - Peptide_034 | (SEQ ID NO: 97) |
| AGDKLVVVDFSATWC | - Peptide_035 | (SEQ ID NO: 98) |
| GDKLVVVDFSATWCG | - Peptide_036 | (SEQ ID NO: 99) |
| DKLVVVDFSATWCGP | - Peptide_037 | (SEQ ID NO: 100) |
| KLVVVDFSATWCGPC | - Peptide_038 | (SEQ ID NO: 101) |
| LVVVDFSATWCGPCK | - Peptide_039 | (SEQ ID NO: 102) |
| VVVDFSATWCGPCKM | - Peptide_040 | (SEQ ID NO: 103) |
| VVDFSATWCGPCKMI | - Peptide_041 | (SEQ ID NO: 104) |
| VDFSATWCGPCKMIK | - Peptide_042 | (SEQ ID NO: 105) |
| DFSATWCGPCKMIKP | - Peptide_043 | (SEQ ID NO: 106) |
| FSATWCGPCKMIKPF | - Peptide_044 | (SEQ ID NO: 107) |
| SATWCGPCKMIKPFF | - Peptide_045 | (SEQ ID NO: 108) |
| ATWCGPCKMIKPFFH | - Peptide_046 | (SEQ ID NO: 109) |
| TWCGPCKMIKPFFHS | - Peptide_047 | (SEQ ID NO: 110) |
| WCGPCKMIKPFFHSL | - Peptide_048 | (SEQ ID NO: 111) |
| CGPCKMIKPFFHSLS | - Peptide_049 | (SEQ ID NO: 112) |
| GPCKMIKPFFHSLSE | - Peptide_050 | (SEQ ID NO: 113) |
| PCKMIKPFFHSLSEK | - Peptide_051 | (SEQ ID NO: 114) |

FIG. 21B

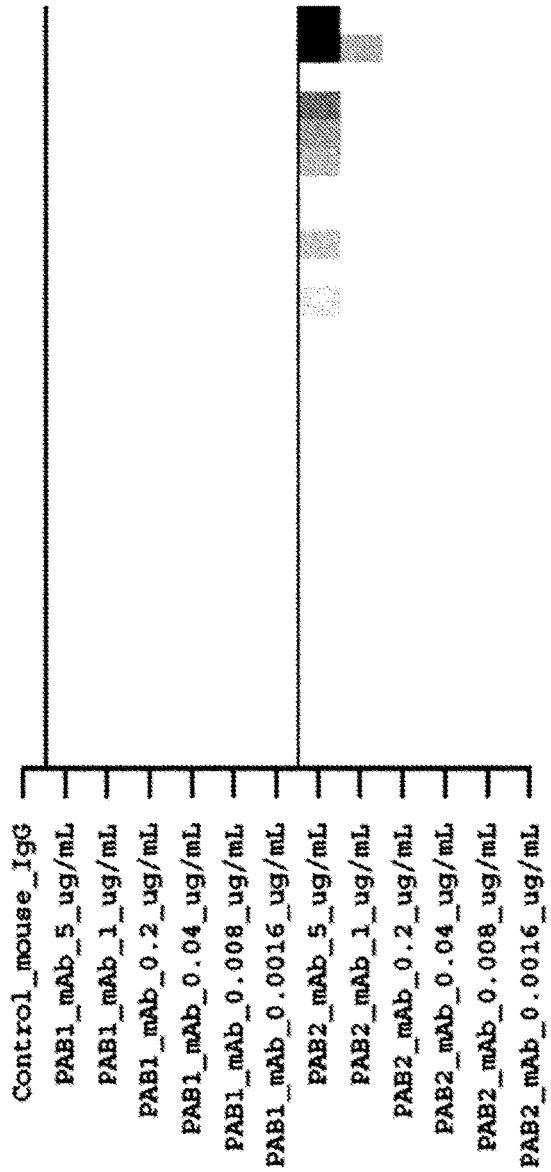

```
CKMIKPFFHSLSEKY - Peptide_052 (SEQ ID NO: 115)
KMIKPFFHSLSEKYS - Peptide_053 (SEQ ID NO: 116)
MIKPFFHSLSEKYSN - Peptide_054 (SEQ ID NO: 117)
IKPFFHSLSEKYSNV - Peptide_055 (SEQ ID NO: 118)
KPFFHSLSEKYSNVI - Peptide_056 (SEQ ID NO: 119)
PFFHSLSEKYSNVIF - Peptide_057 (SEQ ID NO: 120)
FFHSLSEKYSNVIFL - Peptide_058 (SEQ ID NO: 121)
FHSLSEKYSNVIFLE - Peptide_059 (SEQ ID NO: 122)
HSLSEKYSNVIFLEV - Peptide_060 (SEQ ID NO: 123)
SLSEKYSNVIFLEVD - Peptide_061 (SEQ ID NO: 124)
LSEKYSNVIFLEVDV - Peptide_062 (SEQ ID NO: 125)
SEKYSNVIFLEVDVD - Peptide_063 (SEQ ID NO: 126)
EKYSNVIFLEVDVDD - Peptide_064 (SEQ ID NO: 127)
KYSNVIFLEVDVDDC - Peptide_065 (SEQ ID NO: 128)
YSNVIFLEVDVDDCQ - Peptide_066 (SEQ ID NO: 129)
SNVIFLEVDVDDCQD - Peptide_067 (SEQ ID NO: 130)
NVIFLEVDVDDCQDV - Peptide_068 (SEQ ID NO: 131)
VIFLEVDVDDCQDVA - Peptide_069 (SEQ ID NO: 132)
IFLEVDVDDCQDVAS - Peptide_070 (SEQ ID NO: 133)
FLEVDVDDCQDVASE - Peptide_071 (SEQ ID NO: 134)
LEVDVDDCQDVASEC - Peptide_072 (SEQ ID NO: 135)
EVDVDDCQDVASECE - Peptide_073 (SEQ ID NO: 136)
VDVDDCQDVASECEV - Peptide_074 (SEQ ID NO: 137)
DVDDCQDVASECEVK - Peptide_075 (SEQ ID NO: 138)
VDDCQDVASECEVKC - Peptide_076 (SEQ ID NO: 139)
DDCQDVASECEVKCM - Peptide_077 (SEQ ID NO: 140)
DCQDVASECEVKCMP - Peptide_078 (SEQ ID NO: 141)
```

FIG. 21C

THIOREDOXIN 1 EPITOPE, ENCODING NUCLEIC ACID AND METHODS OF BINDING A MONOCLONAL ANTIBODY

CROSS-REFERENCE TO RELATED APPLICATIONS

This application is a national phase application under 35 U.S.C. § 371 of International Application No. PCT/KR2018/012069, filed Oct. 12, 2018, which claims priority to and the benefit of Korean Patent Application No. 10-2017-0132536, filed Oct. 12, 2017. The contents of the referenced patent applications are incorporated into the present application by reference.

This application contains a sequence listing submitted in ASCII format and is hereby incorporated by reference in its entirety. The sequence listing named "ELIPP0105US_SequenceListing" was created Apr. 24, 2023, and is 108,091 bytes in size.

FIELD OF THE DISCLOSURE

The present invention relates to an epitope of a thioredoxin-1 (Trx1) antigen and a monoclonal antibody specifically binding thereto, and more particularly, to the epitope, a monoclonal antibody binding thereto, an antigen-binding fragment thereof, a nucleic acid molecule encoding a heavy chain and/or light chain of the antibody or antigen-binding fragment thereof, a recombinant vector containing the nucleic acid molecule, a host cell containing the recombinant vector, a method of preparing the antibody or antigen-binding fragment thereof, a kit for diagnosing breast cancer, and a method of providing information necessary for breast cancer diagnosis.

DESCRIPTION OF RELATED ART

Thioredoxin (Trx) is a small redox protein of about 12 kDa, which is present in the reduced state by a thioredoxin reductase through NADPH-dependent reduction, and includes thioredoxin-1 (Trx1) and thioredoxin-2 (Trx2) in mammals. Thioredoxin acts as a growth factor, removes hydrogen peroxide which is toxic in cells, promotes binding of critical factors relating to the role of a ribonucleotide reductase and transcription in bacteria to DNA, and affects the activity of a transcription factor such as nuclear transcription factor kB (NF-kB) in eukaryotic cells. Therefore, thioredoxin affects cell death and tumors and thus plays a pivotal role in regulation of cancer cell growth, and cleaves a disulfide bond of another oxidized protein to assist the maintenance of activity in a reduced state. Thioredoxin-1 and 2 reductases remove nitrogen oxide of cysteines in mammalian cells to affect cell death, and have potential significance in various diseases including an inflammatory disease, a heart attack, and cancer. In addition, immunohistochemical analysis using an anti-thioredoxin antibody shows the expression of thioredoxin in human cancer tissues including the liver, colon, pancreas and cervix, and such expression indicates the possibility of involving thioredoxin in tumorigenesis.

Under these circumstances, the inventors had studied a marker for breast cancer diagnosis which can diagnose breast cancer or predict a prognosis thereof early, thioredoxin-1 was lowly expressed in normal breast tissue, but very highly expressed in breast cancer tissue, demonstrating that thioredoxin-1 is useful as a marker for breast cancer diagnosis (Korean Patent No. 10-1058230).

To develop in vitro diagnostics (IVD) based on an enzyme-linked immunosorbent assay (ELISA) to have high accuracy and high precision, a pair of antibodies having different sites with different affinities to the same antigen protein are required. Moreover, it is necessary to have a system producing antibodies having a certain affinity every time with low costs. In the present invention, to detect thioredoxin-1 (Trx1) present in human serum, two types of high-performance recombinant monoclonal antibodies were developed, the antibodies very specifically bind to thioredoxin-1 and thus can be useful for screening breast cancer patients. In addition, by identifying a site of a human Trx1 antigen to which the two types of antibodies bind, the present invention was completed.

SUMMARY OF THE INVENTION

The present invention has been suggested to solve the above-mentioned problems, and is directed to providing a monoclonal antibody or an antigen-binding fragment thereof, which is able to diagnose breast cancer with high sensitivity and specificity.

The present invention is also directed to providing a nucleic acid molecule encoding a heavy chain and/or a light chain of the monoclonal antibody or antigen-binding fragment thereof.

The present invention is also directed to providing a recombinant vector containing the nucleic acid molecule.

The present invention is also directed to providing a host cell containing the recombinant vector.

The present invention is also directed to providing an epitope of a human Trx1 antigen to which the monoclonal antibody or a binding fragment thereof binds, a nucleic acid molecule encoding the same, a recombinant vector containing the nucleic acid molecule and a host cell containing the recombinant vector.

The present invention is also directed to providing a method of preparing a monoclonal antibody specifically binding to Trx1 or an antigen-binding fragment thereof, which includes culturing the host cell.

The present invention is also directed to providing a kit for diagnosing breast cancer, including the above-described monoclonal antibody or antigen-binding fragment thereof.

The present invention is also directed to providing a method of providing information necessary for breast cancer diagnosis using the above-described monoclonal antibody or antigen-binding fragment thereof.

To solve the above-described problems, the present invention provides a monoclonal antibody specifically binding to Trx1 or an antigen-binding fragment thereof, which includes a light chain variable region including light chain CDR1 consisting of an amino acid sequence of SEQ ID NO: 1, light chain CDR2 consisting of an amino acid sequence of SEQ ID NO: 2 and light chain CDR3 consisting of an amino acid sequence of SEQ ID NO: 3, and a heavy chain variable region including heavy chain CDR1 consisting of an amino acid sequence of SEQ ID NO: 4, heavy chain CDR2 consisting of an amino acid sequence of SEQ ID NO: 5 and heavy chain CDR3 consisting of an amino acid sequence of SEQ ID NO: 6.

According to an exemplary embodiment of the present invention, the antibody may include a light chain variable region consisting of an amino acid sequence of SEQ ID NO: 13 and a heavy chain variable region consisting of an amino acid sequence of SEQ ID NO: 14.

According to another exemplary embodiment of the present invention, the antibody may include a light chain consisting of an amino acid sequence of SEQ ID NO: 17 and a heavy chain consisting of an amino acid sequence of SEQ ID NO: 18.

The present invention also provides a monoclonal antibody specifically binding to Trx1 or an antigen-binding fragment thereof, which includes a light chain variable region including light chain CDR1 consisting of an amino acid sequence of SEQ ID NO: 7, light chain CDR2 consisting of an amino acid sequence of SEQ ID NO: 8 and light chain CDR3 consisting of an amino acid sequence of SEQ ID NO: 9, and a heavy chain variable region including heavy chain CDR1 consisting of an amino acid sequence of SEQ ID NO: 10, heavy chain CDR2 consisting of an amino acid sequence of SEQ ID NO: 11 and heavy chain CDR3 consisting of an amino acid sequence of SEQ ID NO: 12.

According to one exemplary embodiment of the present invention, the antibody may include a light chain variable region consisting of an amino acid sequence of SEQ ID NO: 15 and a heavy chain variable region consisting of an amino acid sequence of SEQ ID NO: 16.

According to another exemplary embodiment of the present invention, the antibody may include a light chain consisting of an amino acid sequence of SEQ ID NO: 19 and a heavy chain consisting of an amino acid sequence of SEQ ID NO: 20.

According to still another exemplary embodiment of the present invention, the antibody may include a light chain consisting of an amino acid sequence of SEQ ID NO: 25 and a heavy chain consisting of an amino acid sequence of SEQ ID NO: 26.

According to yet another exemplary embodiment of the present invention, the antibody may include an IgG1 heavy chain and a kappa (κ) light chain.

According to yet another exemplary embodiment of the present invention, the antigen-binding fragment may be Fab, F(ab'), F(ab')$_2$, Fv or a single chain antibody molecule.

According to yet another exemplary embodiment of the present invention, the antibody may be a chimeric antibody, a humanized antibody or a human antibody.

The present invention also provides a nucleic acid molecule encoding a heavy chain and/or light chain of the above-described antibody or antigen-binding fragment thereof.

According to one exemplary embodiment of the present invention, the nucleic acid molecule encoding the light chain may consist of a nucleotide sequence of SEQ ID NO: 21, a nucleotide sequence of SEQ ID NO: 23 or a nucleotide sequence of SEQ ID NO: 27.

According to one exemplary embodiment of the present invention, the nucleic acid molecule encoding the heavy chain may consist of a nucleotide sequence of SEQ ID NO: 22, a nucleotide sequence of SEQ ID NO: 24 or a nucleotide sequence of SEQ ID NO: 28.

The present invention also provides a recombinant vector containing the nucleic acid molecule encoding the heavy chain, the nucleic acid encoding the light chain or both of the nucleic acid molecules encoding the heavy chain and the light chain, and a host cell containing the same.

The present invention also provides an epitope of a human Trx1 antigen consisting of any one amino acid sequence selected from the group consisting of SEQ ID NOs: 32 to 34 and 172 to 176, and a nucleic acid molecule encoding the same.

According to one exemplary embodiment of the present invention, the nucleic acid molecule may consist of any one nucleotide sequence selected from the group consisting of SEQ ID NOs: 35 to 37 and 177 to 181.

The present invention also provides a recombinant vector containing the nucleic acid molecule and a host cell containing the same.

The present invention also provides a method of preparing a monoclonal antibody specifically binding to Trx1 or an antigen-binding fragment thereof, which includes culturing a host cell containing a recombinant vector including a nucleic acid molecule encoding a heavy chain of the above-described antibody, a nucleic acid encoding a light chain thereof, or both of the nucleic acid molecules encoding the heavy chain and the light chain thereof.

The present invention also provides a kit for diagnosing breast cancer, which includes the above-described antibody or antigen-binding fragment thereof.

According to one exemplary embodiment of the present invention, the kit may be an enzyme-linked immunosorbent assay (ELISA) kit.

According to another exemplary embodiment of the present invention, the ELISA may be any one selected from the group consisting of direct ELISA, indirect ELISA, direct sandwich ELISA and indirect sandwich ELISA.

The present invention also provides a method of providing information necessary for breast cancer diagnosis, which includes: (a) bringing the above-described monoclonal antibody or antigen-binding fragment thereof into contact with a biological sample isolated from a subject suspected of having breast cancer; (b) measuring an expression level of the Trx1 protein binding to the monoclonal antibody or antigen-binding fragment thereof in the biological sample through the formation of an antigen-antibody complex; and (c) comparing the expression level of the Trx1 protein, measured in Step (b) with that of a control and, if the protein expression level is higher than that of the control, determining the subject to be a breast cancer patient.

Further, the present invention provides a method of providing information necessary for breast cancer diagnosis, which includes: (a) coating a solid support with a monoclonal antibody or an antigen-binding fragment thereof, including light chains CDR1 to CDR3 and heavy chains CDR1 to CDR3 of antibody B266 or B266-1, a monoclonal antibody or an antigen-binding fragment thereof including a light chain variable region and a heavy chain variable region of antibody B266 or B266-1, or antibody B266 or B266-1 or an antigen-binding fragment thereof; (b) applying a biological sample isolated from a subject suspected of having breast cancer to the coated solid support; (c) removing an unbound sample; (d) applying a monoclonal antibody or an antigen-binding fragment thereof, including light chains CDR1 to CDR3 and heavy chains CDR1 to CDR3 of antibody B264, a monoclonal antibody or an antigen-binding fragment thereof, including a light chain variable region and a heavy chain variable region of antibody B264, or antibody B264 or an antigen-binding fragment thereof to the solid support; (e) removing an unbound monoclonal antibody or antigen-binding fragment thereof; (f) measuring an expression level of Trx1 protein; and (g) comparing the expression level of the Trx1 protein, measured in Step (f), with that of a control, and, if the protein expression level is higher than that of the control, determining the subject to be a breast cancer patient.

According to one exemplary embodiment of the present invention, the expression level of the Trx1 protein may be measured by any one method selected from the group consisting of Western blotting, ELISA, sandwich ELISA, a radioimmunoassay, radioimmunodiffusion, Ouchterlony immunodiffusion, an immunoprecipitation assay, a complement fixation assay, an immunochromatographic assay, FACS and a protein chip assay.

According to another exemplary embodiment of the present invention, the isolated biological sample may be any one or more selected from the group consisting of whole blood, serum, plasma, breast tissue and breast cells.

Unless defined otherwise, all technical and scientific terms used in the specification have the same meaning as commonly understood by one of ordinary skill in the art to which the invention belongs. Generally, the nomenclature used herein is well known and commonly used in the art.

The definitions of key terms used herein are as follows.

The term "antigen" refers to a molecule which can be bound by an antibody, and can be used in an animal to produce an antibody capable of binding to an epitope of the antigen or a part of the molecule. The antigen may have one or more epitopes.

The term "antibody" or "Ab" is an immunoglobulin molecule which can recognize a specific target or antigen, for example, a carbohydrate, a polynucleotide, a lipid or a polypeptide through one or more antigen recognition sites, located in a variable region of the immunoglobulin molecule, and bind thereto. The term "antibody" used herein may refer to any type of antibody, which encompasses, but is not limited to, a monoclonal antibody; a polyclonal antibody; an "antigen-binding fragment" of an antibody possessing an ability of specifically binding to a specific antigen (e.g., Trx1), for example, Fab, Fab', F(ab')$_2$, Fd, Fv, Fc, etc.; an isolated complementarity-determining region (CDR); a bispecific antibody; a hetero-conjugated antibody, or a mutant thereof; an antibody, or a fusion protein having an antigen-binding fragment (e.g., a domain antibody); a single-chain variable fragment (ScFv) and a single domain antibody [e.g., shark and camelid antibodies]; a maxibody, a minibody, an intrabody, a diabody, a triabody, a tetrabody, v-NAR and bis-scFv; a humanized antibody; a chimeric antibody; and all other modified configurations of an immunoglobulin molecule including an antigen recognition site with required specificity (including glycosylated variants of an antibody, amino acid sequence variants of an antibody and a covalently modified antibody). The antibody may be derived from a mouse, a rat, a human, or any other origin (including a chimeric or humanized antibody).

An antibody or polypeptide which "specifically binds" to a specific target or antigen (e.g., Trx1 protein) is a term generally understood in the related art, and a method of determining such specific binding has also been widely known in the related art. A specific molecule is considered to have "specific binding" when reacting or linked to a special cell or material more frequently, more rapidly, more consistently and/or with higher affinity than that with another type of cells or material. A specific antibody "specifically binds" to a specific target or antigen with higher affinity, higher binding activity, more rapidly and/or more consistently than when binding to another material.

The term "binding affinity" or "$K_D$" used herein refers to an equilibrium dissociation constant of a particular antigen-antibody interaction. $K_D$ is a ratio of a dissociation rate (also referred to as "release rate" or "$k_d$") to a binding rate or an "operation rate" or "$k_a$ (association rate constant)". Therefore, $K_D$ is $k_d/k_a$, which is expressed as molar concentration (M). It concludes that the lower $K_D$, the higher binding affinity. Therefore, a $K_D$ of 1 µM indicates a lower binding affinity, compared with a $K_D$ of 1 nM. The $K_D$ value of the antibody may be determined using a method widely established in the art. One method of determining the $K_D$ of an antibody typically utilizes surface plasmon resonance using a biosensor system, for example, a Biacore® system.

The term "vector" includes a nucleic acid molecule capable of delivering a linked different nucleic acid. One type of vector is a "plasmid," and refers to a circular double-stranded DNA loop into which an additional DNA fragment can be ligated. A different type of vector is a viral vector, and here, an additional DNA fragment may be attached to a viral genome. Some vectors can be self-replicated in host cells into which they are introduced (e.g., a bacterial vector having a bacterial origin of replication and an episomal mammalian vector). Other vectors (e.g., a non-episomal mammalian vector) may be integrated into the genome of host cells when introduced into the host cells, and thus replicated in accordance with the host genome. In addition, some vectors may direct the expression of operatively linked genes. The vectors are referred to as "recombinant expression vectors" (or simply as "expression vectors") in the specification. Generally, the expression vector useful in the recombinant DNA technique is often present in the form of a plasmid. The "plasmid" and "vector" used herein are the types of vectors most generally used, and thus can be interchangeably used. However, the present invention is to include different types of expression vectors having the same function, for example, viral vectors (e.g., a replication-deficient retrovirus, an adenovirus, and an adeno-related virus).

The term "host cells" is used to express cells which are transformed, or transformed by a nucleic acid sequence to express a selected gene of interest. The term encompasses the descendants of mother cells whether or not the descendants are identical to the original parent in the morphological or genetic aspect, as long as the selected gene is present.

A monoclonal antibody of the present invention has excellent binding affinity to thioredoxin-1, thereby very specifically binding to thioredoxin-1, and has very high sensitivity and specificity, thereby being effectively used in screening a breast cancer patient. Further, detection of thioredoxin-1 using the monoclonal antibody specifically binding to thioredoxin-1 of the present invention, rather than detection using a conventional breast cancer diagnostic biomarker CA15-3, exhibits exceptionally high sensitivity and specificity, and thus the accuracy and reliability of breast cancer diagnosis can be significantly increased. An epitope region of a human Trx1 antigen to which an antibody binds according to the present invention can be effectively used in the development of an improved antibody to enhance the binding affinity of an anti-Trx1 antibody.

BRIEF DESCRIPTION OF THE DRAWINGS

FIG. 2 shows the amino acid sequences of a light chain (a) and a heavy chain (b) of a 9G7(AB1) antibody obtained in Example 1.

FIG. 3 shows the amino acid sequences of a light chain (a) and a heavy chain (b) of a 2B4(AB2) antibody obtained in Example 1.

FIG. 11 shows the comparison of amino acid sequence homology between human Trx1 and *Chrysochloris asiatica* Trx1.

FIG. 15A shows the comparison of amino acid sequences between CaTrx1 and hTrx1.

FIG. 15B shows the positioning of mutations according to the comparison of amino acid sequences between CaTrx1 and hTrx1.

FIGS. 18A to 18C show results of analyzing the binding strength of an anti-Trx1 antibody with respect to the 8 types of hTrx1 mutant proteins of the present invention.

FIGS. 21A to 21D are a heatmap diagram showing the extent of reaction of controls reacting with antibody samples and all probe peptides, in which the y axis represents the peptide sequences of a library, and the x axis represents the concentrations of the applied antibody samples. MMC2 values are represented by a color code range including white (0 or low intensity), yellow (medium intensity) and red (high intensity).

DETAILED DESCRIPTION OF THE INVENTION

Hereinafter, the present invention will be described in further detail.

As described above, the inventors confirmed through previous research that thioredoxin-1 is expressed in normal breast tissue at a low level, but expressed in breast cancer tissue at a very high level. Therefore, it is proved that thioredoxin-1 is useful as a marker for breast cancer diagnosis.

Therefore, through further research, the inventors developed a monoclonal antibody which very specifically binds to thioredoxin-1 and is useful in screening a breast cancer patient. The monoclonal antibody of the present invention very specifically binds to thioredoxin-1 due to excellent binding affinity to thioredoxin-1 and has very high sensitivity and specificity, such that it can be effectively used in screening a breast cancer patient. Further, the detection of thioredoxin-1 using the monoclonal antibody of the present invention, which specifically binds to thioredoxin-1, rather than the detection of CA15-3, which is another, conventionally used biomarker for breast cancer diagnosis, exhibits excellent sensitivity and specificity, such that the accuracy and reliability of the diagnosis of breast cancer can be significantly increased. In addition, an epitope region of a human Trx1 antigen to which the antibody binds may be effectively used in the development of an improved antibody to enhance the binding affinity of an anti-Trx1 antibody.

The present invention provides a monoclonal antibody binding to thioredoxin-1 (Trx1) or an antigen-binding fragment thereof.

The monoclonal antibody of the present invention may be prepared using a variety of methods known in the art such as hybridoma, recombination and phage display technologies, and a combination method thereof. For example, the monoclonal antibody may be prepared using a hybridoma technique, which is known in the art. The term "monoclonal antibody" used herein is not limited to an antibody produced using a hybridoma technique. The term "monoclonal antibody" refers to an antibody derived from a single clone of any eukaryote, prokaryote, or a phage clone, but does not refer to a method of producing the same.

Figure 1:
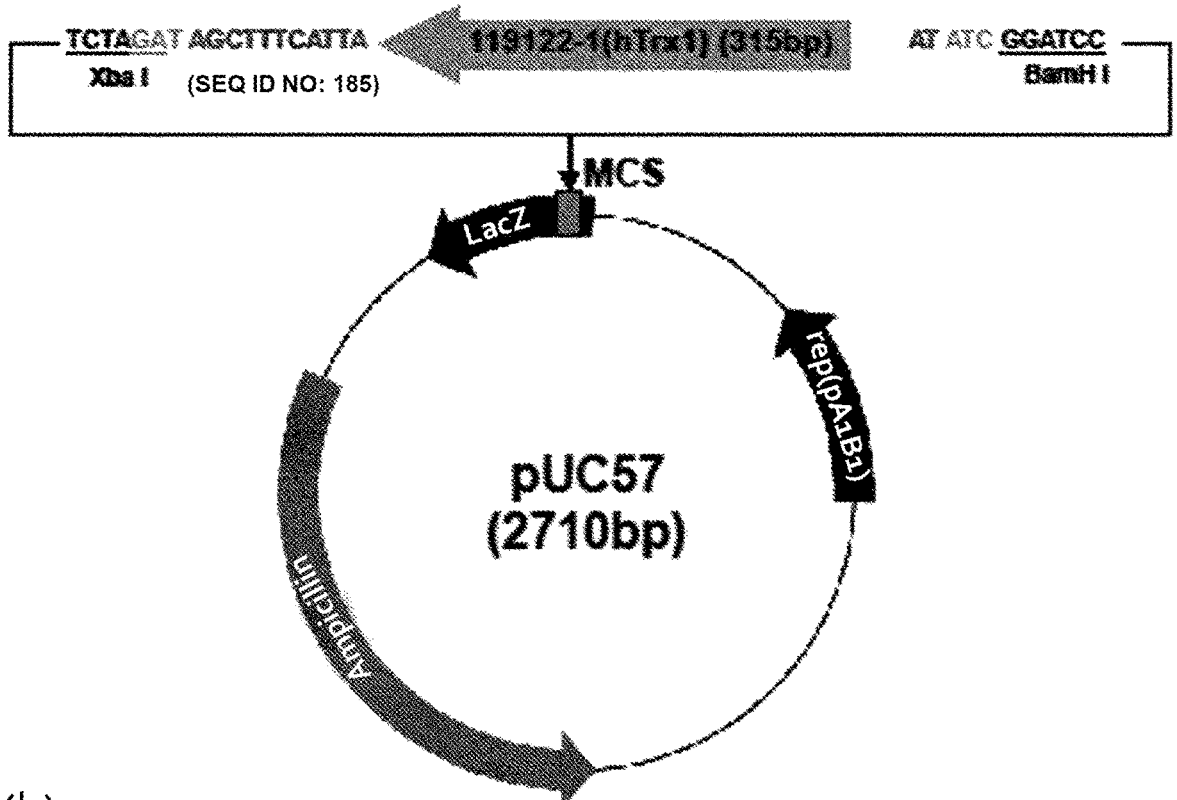
FIG. 1 shows the cleavage map of a recombinant vector expressing the thioredoxin-1 antigen and an isotyping result of an antibody obtained in Example 1.
Figure 4:
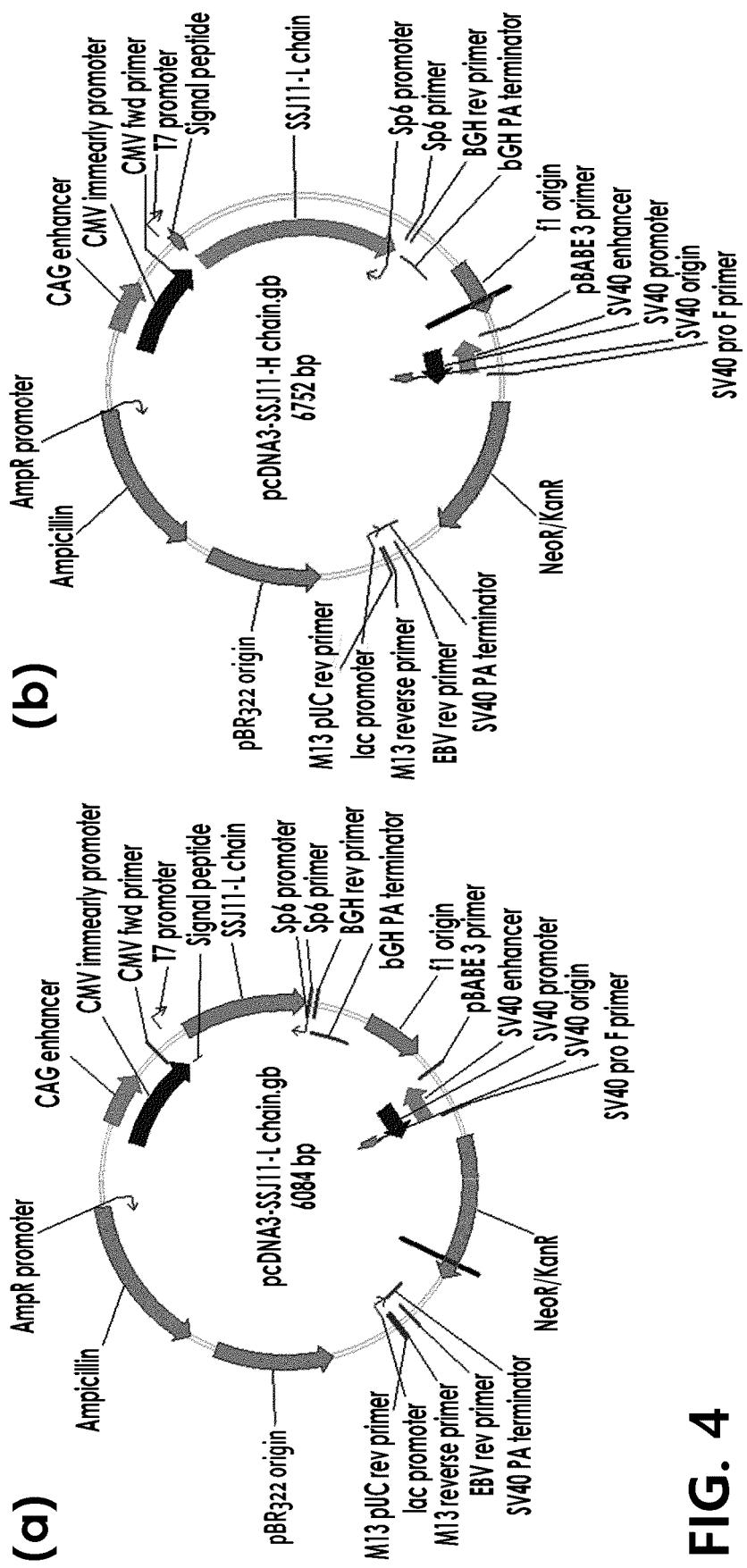
FIG. 4 shows a set of cleavage maps of a recombinant vector expressing a light chain (a) and a heavy chain (b) of a B264 antibody with high affinity.
Figure 5:
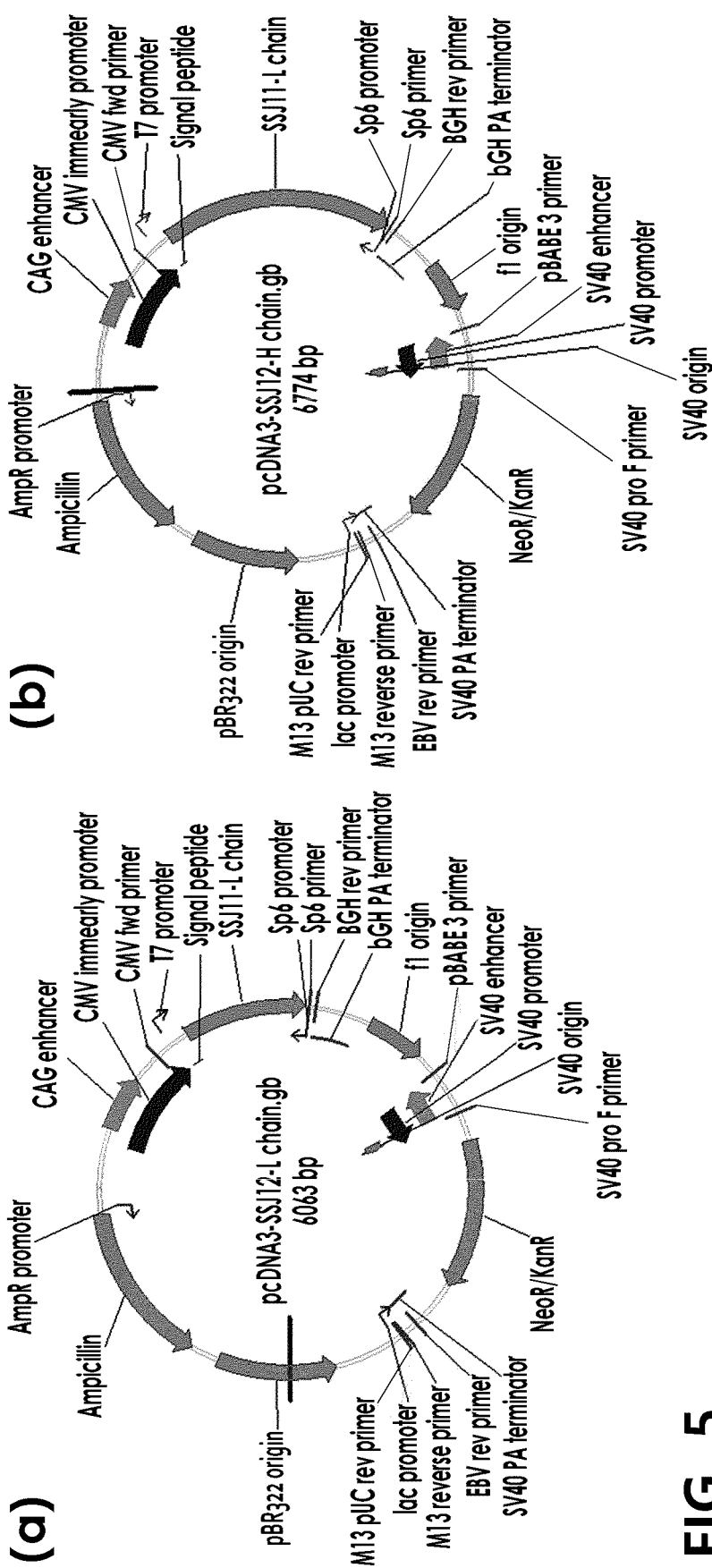
FIG. 5 shows a set of cleavage maps of a recombinant vector expressing a light chain (a) and a heavy chain (b) of a B266 antibody with high affinity.

A method of producing and screening a specific antibody using a hybridoma technique is common and well known in the art. As a non-limited example, a mouse can be immunized with a target antigen or cells expressing the same. When the immune reaction is detected, for example, an antibody specific to the antigen is detected from a mouse serum, a mouse spleen is collected to isolate spleen cells. Subsequently, the spleen cells are fused with any suitable myeloma cells, for example, P3U1, P3X63-Ag8, P3X63-Ag8-U1, P3NS1-Ag4, SP2/0-Ag14, or P3X63-Ag8-653 by a known method. A hybridoma is selected, and cloned by limiting dilution. Afterward, the hybridoma clone is evaluated for its ability to be a cell secreting an antibody capable of binding to an antigen by a method known in the art. Generally, ascites containing a high level of antibodies may be prepared by injecting positive hybridoma clones into the abdominal cavity of a mouse. In an exemplary embodiment of the present invention, a Trx1 antigen is prepared by transfecting *E. coli* with a recombinant vector having the cleavage map of FIG. 1(*a*). Afterward, the spleen of a rat immunized with the antigen is separated, and cells fused with myeloma cells (sp2/0) to produce an antibody reacting with Trx1 are identified by ELISA.

The exemplary monoclonal antibody of the present invention or antigen-binding fragment thereof may include (a) or (b) as follows, which may be referred to as B264 or B266-1, respectively:

(a) a light chain variable region including a light chain CDR1 consisting of the amino acid sequence of SEQ ID NO: 1, a light chain CDR2 consisting of the amino acid sequence of SEQ ID NO: 2 and a light chain CDR3 consisting of the amino acid sequence of SEQ ID NO: 3, and a heavy chain variable region including a heavy chain CDR1 consisting of the amino acid sequence of SEQ ID NO: 4, a heavy chain CDR2 consisting of the amino acid sequence of SEQ ID NO: 5 and a heavy chain CDR3 consisting of the amino acid sequence of SEQ ID NO: 6; or (b) a light chain variable region including a light chain CDR1 consisting of the amino acid sequence of SEQ ID NO: 7, a light chain CDR2 consisting of the amino acid sequence of SEQ ID NO: 8 and a light chain CDR3 consisting of the amino acid sequence of SEQ ID NO: 9, and a heavy chain variable region including a heavy chain CDR1 consisting of the amino acid sequence of SEQ ID NO: 10, a heavy chain CDR2 consisting of the amino acid sequence of SEQ ID NO: 11 and a heavy chain CDR3 consisting of the amino acid sequence of SEQ ID NO: 12.

The term "complementarity-determining region (CDR)" used herein refers to the amino acid sequence of a hypervariable region of the heavy chain or light chain in an immunoglobulin. Each of heavy chains (CDRH1, CDRH2 and CDRH3) and light chains (CDRL1, CDRL2 and CDRL3) has three CDRs, and these CDRs provide key contact residues when an antibody binds to an antigen or epitope.

The exemplary monoclonal antibody of the present invention or antigen-binding fragment thereof may include (c) or (d) as follows, and may be referred to as B264 or B266-1, respectively:

(c) a light chain variable region consisting of the amino acid sequence of SEQ ID NO: 13 and a heavy chain variable region consisting of the amino acid sequence of SEQ ID NO: 14; or (d) a light chain variable region consisting of the amino acid sequence of SEQ ID NO: 15 and a heavy chain variable region consisting of the amino acid sequence of SEQ ID NO: 16.

The exemplary monoclonal antibody of the present invention or antigen-binding fragment thereof may include (e) or (f) as follows, which may be referred to as B264 or B266, respectively:

(e) a light chain consisting of the amino acid sequence of SEQ ID NO: 17 and a heavy chain consisting of the amino acid sequence of SEQ ID NO: 18; or (f) a light chain consisting of the amino acid sequence of SEQ ID NO: 19 and a heavy chain consisting of the amino acid sequence of SEQ ID NO: 20.

The exemplary monoclonal antibody of the present invention is referred to as B264, B265, B266, B267, B268 or B269, and most preferably B264 or B266-1. B266-1 is a monoclonal antibody in which the Fc part of B266 is modified to human IgG1.

The structural unit of a naturally-occurring antibody generally includes a tetramer. The tetramer is generally composed of two pairs of identical polypeptide chains, and each pair has one full-length light chain (generally having a molecular weight of about 15 kDa) and one full-length heavy chain (generally having a molecular weight of about 50 to 70 kDa). The amino end of each of the light chain and heavy chain generally includes a variable region with about 100 to 110 or more amino acids, involved in antigen recognition. The carboxyl end of each chain defines a constant region generally involved in the function of an effector. A human light chain is generally classified into κ and λ light chains. A heavy chain is generally classified into μ, δ, γ, α and ε heavy chains, which define isotypes of an antibody, such as IgM, IgD, IgG, IgA and IgE, respectively. IgG has, but is not limited to, some subclasses including IgG1, IgG2, IgG3 and IgG4. IgM has, but is not limited to, subclasses including IgM1 and IgM2. Similarly, IgA is, but is not limited to, classified into subclasses including IgA1 and IgA2. In the full-length light and heavy chains, generally, variable and constant regions are connected by a "J" region with about 12 or more amino acids, and the heavy chain also includes a "D" region with about 10 or more amino acids. A variable region of each light chain/heavy chain pair generally forms an antigen-binding site. According to an exemplary embodiment of the present invention, in the monoclonal antibody of the present invention, the heavy chain may be an IgG1, IgG2a, IgG2b, IgG3, IgA or IgM isotype, and the light chain may be a κ chain or a λ chain, and preferably, a κ light chain and an IgG1 heavy chain.

In the monoclonal antibody of the present invention or antigen-binding fragment thereof, the "antigen-binding fragment thereof" means a fragment having an antigen-binding function, and includes Fab, F(ab'), F(ab')$_2$, Fv or a single-chain antibody molecule. Among the antibody-binding fragments, Fab is a structure having light and heavy chain variable regions and a light chain constant region and the first constant region (CH1) of a heavy chain, and includes one antigen-binding site. F(ab') is different from Fab in that it has a hinge region including one or more cysteine residues at the C-terminus of the heavy chain CH1 domain. F(ab')$_2$ is formed by a disulfide bond between cysteine residues in a hinge region of Fab'. Fv is the smallest antibody fragment only having a heavy chain variable region and a light chain variable region. Such an antibody fragment may be obtained using a protease, preferably gene recombination technology. For example, Fab may be obtained by, for example, digestion of the total antibody with papain, and a F(ab')$_2$ fragment may be obtained by digestion of the total antibody with pepsin.

The exemplary antibody of the present invention may be a chimeric antibody, a humanized antibody or a complete human antibody.

The chimeric antibody may be prepared by combining variable light chain and heavy chain (VL and VH) domains obtained from one type of antibody-producing cells and constant light chain and heavy chain domains obtained from another type of antibody using a recombination means. Generally, the chimeric antibody uses a rodent or rabbit variable domain and a human constant domain to produce an antibody usually having a human domain. The production of such a chimeric antibody is widely known in the art, and may be achieved by a standard means. It is further considered that the human constant region of the chimeric antibody of the present invention can be selected from an IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant region.

The humanized antibody is engineered to contain an immunoglobulin domain further more similar to a human, and includes a complementarity-determining region of an animal-derived antibody. This is achieved by closely examining the sequence of a hypervariable loop of the variable region in a monoclonal antibody, and adapting the sequence to the structure of the human antibody chain.

The complete human antibody is an antibody molecule which includes CDRs such that the total sequences of both of a light chain and a heavy chain are derived from a human gene.

The present invention also provides a nucleic acid molecule(s) encoding a heavy chain and/or a light chain of a monoclonal antibody of the present invention or an antigen-binding fragment thereof.

The term "nucleic acid molecule" used herein encompasses DNA (gDNA and cDNA) and RNA molecules, and in the nucleic acid molecule, a nucleotide, which is a basic unit, also includes an analogue in which a sugar or base part is modified, as well as a natural nucleotide.

The sequences of nucleic acid molecules encoding the heavy chain and light chain variable regions of the present invention may be modified. The modification includes additions, deletions, or non-conservative or conservative substitutions of nucleotides.

The nucleic acid molecule of the present invention is interpreted to also include a nucleotide sequence having substantial identity to the nucleotide sequence described above. The substantial identity refers to a nucleotide sequence exhibiting at least 80% homology, at least 90% homology in one specific example, or at least 95% homology in another specific example when the nucleotide sequence of the present invention is aligned to correspond to a different sequence as much as possible, and the aligned sequence is analyzed using an algorithm generally used in the art.

According to an exemplary embodiment of the present invention, the nucleic acid molecule encoding a light chain of the monoclonal antibody of the present invention may consist of the nucleotide sequence of SEQ ID NO: 21, and the nucleic acid molecule encoding a heavy chain of the monoclonal antibody of the present invention may consist of the nucleotide sequence of SEQ ID NO: 22.

According to another exemplary embodiment of the present invention, the nucleic acid molecule encoding a heavy chain of the monoclonal antibody of the present invention may consist of the nucleotide sequence of SEQ ID NO: 23, and the nucleic acid molecule encoding a light chain of the monoclonal antibody of the present invention may consist of the nucleotide sequence of SEQ ID NO: 24.

According to another exemplary embodiment of the present invention, a nucleic acid molecule encoding a light chain of the monoclonal antibody of the present invention may consist of a nucleotide sequence of SEQ ID NO: 27, and a nucleic acid molecule encoding a heavy chain thereof may consist of a nucleotide sequence of SEQ ID NO: 28.

The present invention also provides a recombinant vector, which includes the nucleic acid molecule encoding a heavy chain, the nucleic acid molecule encoding a light chain in the monoclonal antibody, or both of the nucleic acid molecules.

The recombinant vector system of the present invention may be constructed by various methods known in the art. The vector of the present invention may be typically constructed as a vector for cloning or a vector for expression. In addition, the vector of the present invention may be constructed using prokaryotic or eukaryotic cells as a host. For example, the vector of the present invention is an expression vector, and when prokaryotic cells are used as a host, the vector generally includes a potent promoter capable of performing transcription (e.g., a tac promoter, a lac promoter, a lacUV5 promoter, a lpp promoter, a pLλ promoter, a pRλ promoter, a rac5 promoter, an amp promoter, a recA promoter, an SP6 promoter, a trp promoter or a T7 promoter), a ribosome-binding site for the initiation of translation and transcription/translation termination sequences. When *E. coli* (e.g., HB101, BL21, DH5α, etc.) is used as a host cell, promoter and operator regions of an *E. coli* tryptophan biosynthesis pathway, and a pLλ promoter may be used as regulatory regions. When *Bacillus* is used as a host cell, the promoter of a toxic protein gene of *Bacillus thuringiensis* or any promoter capable of being expressed in *Bacillus* may be used as a regulatory region.

Meanwhile, the recombinant vector of the present invention may be manufactured by manipulating a plasmid used in the art (e.g., pCL, pSC101, pGV1106, pACYC177, ColE1, pKT230, pME290, pBR322, pUC8/9, pUC6, pBD9, pHC79, pIJ61, pLAFR1, pHV14, pGEX series, pET series or pUC19), a phage (e.g., λgt4·λB, λ-Charon, λΔz1 or M13) or a virus (e.g., SV40).

When the vector of the present invention is an expression vector and eukaryotic cells are used as a host, the vector generally has a promoter derived from the genome of mammalian cells (e.g., a metallothionine promoter, a β-actin promoter, a human hemoglobin promoter or a human muscle creatine promoter) or a promoter derived from a mammalian virus (e.g., an adenovirus late promoter, a vaccinia virus 7.5K promoter, SV40 promoter, a cytomegalovirus (CMV) promoter, a tk promoter of HSV, a mouse mammary tumor virus (MMTV) promoter, an LTR promoter of HIV, a Moloney virus promoter, an Epstein-Barr virus (EBV) promoter or a Rous sarcoma virus (RSV) promoter), and a polyadenylation sequence as a transcription termination sequence.

The recombinant vector of the present invention may be fused with a different sequence to facilitate the purification of an antibody expressed from the recombinant vector. The fused sequence may be, for example, a glutathione S-transferase (Amersham Pharmacia Biotech, USA); a maltose-binding protein (NEB, USA); FLAG (IBI, USA); a tag sequence such as 6×His (hexahistidine; Qiagen, USA), Pre-S1 or c-Myc; or a leading sequence such as ompA or pelB. In addition, since a protein expressed from the vector of the present invention is an antibody, the expressed antibody may be easily purified using a protein A column without an additional sequence for purification.

Meanwhile, the recombinant vector of the present invention includes an antibiotic-resistant gene generally used in the art as a selective marker, for example, a gene resistant to ampicillin, gentamicin, carbenicillin, chloramphenicol, streptomycin, kanamycin, geneticin, neomycin or tetracycline.

The vector expressing an antibody of the present invention may be a vector system expressing both of a light chain and a heavy chain using one vector, or a vector system respectively expressing a light chain and a heavy chain using two vectors. In the latter, two vectors are introduced into host cells through co-transformation and targeted transformation. The co-transformation is a method of selecting cells expressing both a light chain and a heavy chain after vector DNAs respectively encoding the light chain and the heavy chain are introduced into host cells. Targeted transformation is a method of selecting cells transformed by a vector including a light chain (or a heavy chain), transforming the selected cells expressing the light chain by a vector including a heavy chain (or a light chain), and finally selecting cells expressing both of the light chain and the heavy chain.

The present invention also provides host cells including a recombinant vector of the present invention. The host cells are cells transformed with the recombinant vector of the present invention. Host cells capable of stably and continuously cloning and expressing the vector of the present invention may be any host cells known in the art, and include prokaryotic host cells, for example, *Bacillus* sp. strains such as *Escherichia coli*, *Bacillus subtilis* and *Bacillus thuringiensis*, *Streptomyces*, *Pseudomonas* (e.g., *Pseudomonas putida*), *Proteus mirabilis* or *Staphylococcus* (e.g., *Staphylococcus carnosus*), but the present invention is not limited thereto.

As eukaryotic host cells suitable for the vector, multicellular fungi such as *Aspergillus* sp. strains belonging to the Phylum Ascomycota and *Neurospora crassa*, and unicellular fungi including enzymes such as yeasts such as *Pichia pastoris*, *Saccharomyces cerevisiae* and *Schizosaccharomyces*, other low eukaryotic cells, high eukaryotic cells such as insect-derived cells, and cells derived from a plant or mammal may be used.

The term "transfection" used herein refers to introduction of a gene of interest into host cells using the recombinant vector of the present invention, and is used with the same meaning as "transformation." Therefore, the "transfection" and/or "transformation" into host cells may be performed by suitable standard technology known in the art according to host cells, including methods of introducing a nucleic acid into an organism, cells, tissue or an organ. Such methods include electroporation, protoplast fusion, calcium phosphate ($CaPO_4$) precipitation, calcium chloride ($CaCl_2$)) precipitation, stirring using a silicon carbide fiber, agrobacteria-mediated transformation, PEG, dextran sulfate, Lipofectamine and drying/inhibition-mediated transformation, but the present invention is not limited thereto.

The present invention also provides an epitope of a human Trx1 antigen consisting of any one amino acid sequence selected from the group consisting of SEQ ID NOs: 32 to 34 and 172 to 176.

Figure 15C:
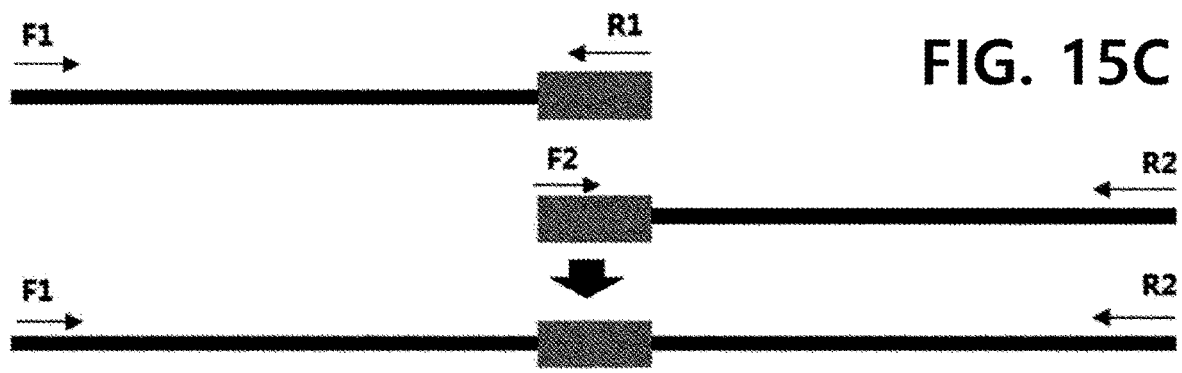
FIG. 15C is a schematic diagram of fusion PCR for manufacturing a hTrx1 mutant gene, which results from DNA fragment amplification and overlapping PCR, which are sequentially performed.

The inventors confirmed that although hTrx1 and CaTrx1 have an amino acid homology of 82%, two types of antibodies against hTrx1 according to the present invention do not bind to CaTrx1 (FIGS. 11 and 15A). Accordingly, eight parts at which the amino acid sequences of hTrx1 and CaTrx1 are different were identified (FIG. 15B), and gene cassettes for expressing hTrx1 mutant proteins were manufactured to clone the genes (FIGS. 15C to 15F). The cloned genes were transformed into an N293F cell line, the expression of 8 types of hTrx1 mutant proteins was confirmed (FIG. 16), and each mutant protein was purified (FIG. 17), followed by confirming the binding strengths with antibody B266-1 (hTrx1-hIgG1) and with antibody B264 (hTrx1-mIgG1).

Figure 18A:
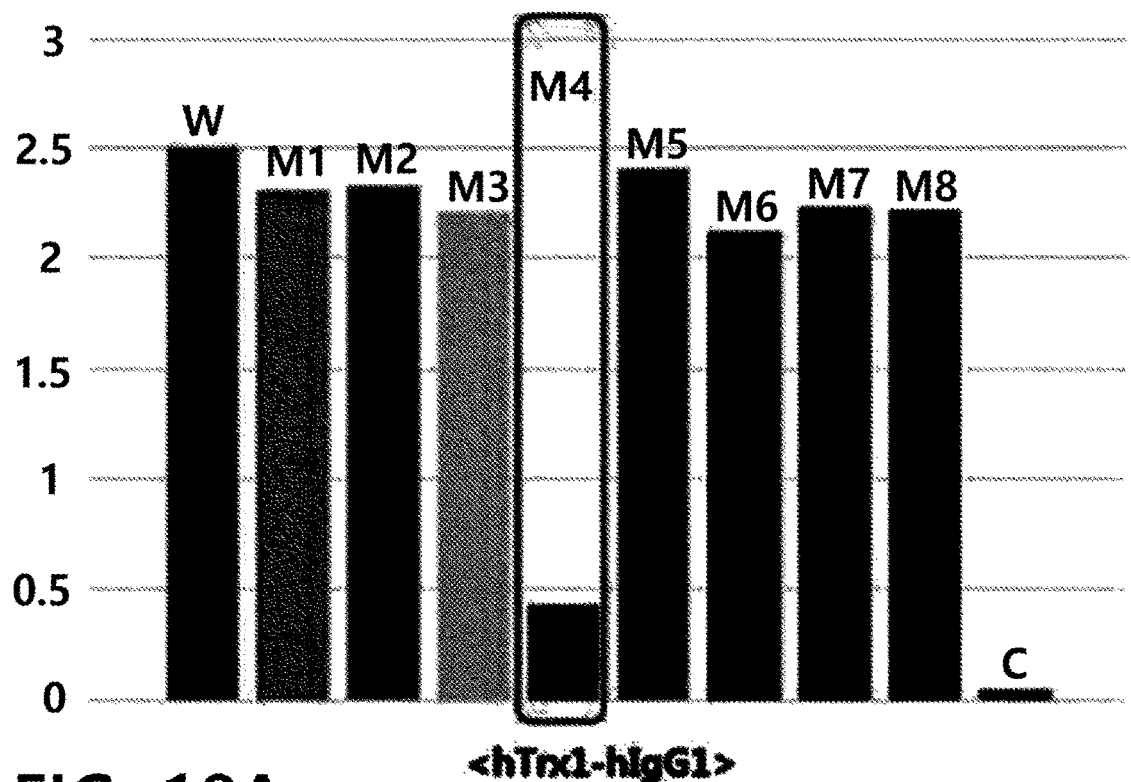
Figure 18B:
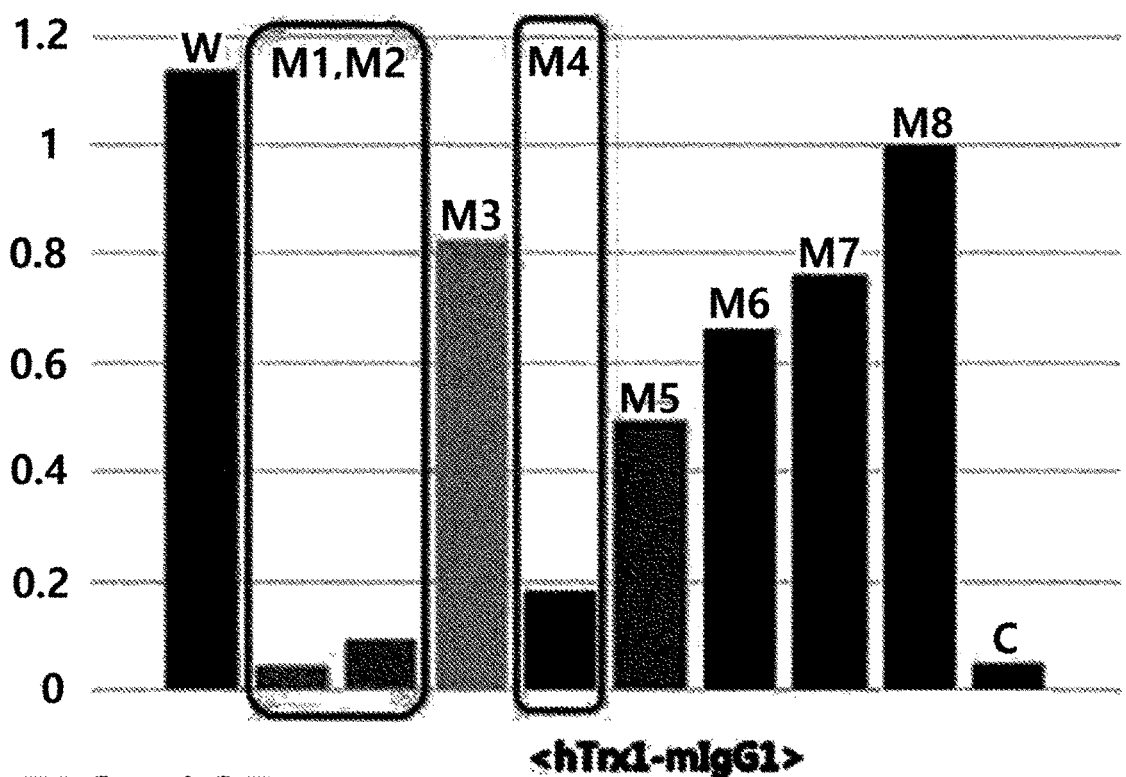

As shown in FIGS. 18A to 18C, it was confirmed that binding between the antibody B266-1 and a M4 mutant protein (YSNVIFGNMV; SEQ ID NO: 184) was decreased compared to hTrx1, and bindings between the antibody B264 and M1 (QIESKTAEIEGKED; SEQ ID NO: 182), M2 (QEALDAHAALSS; SEQ ID NO: 183) and M4 mutant proteins were decreased compared to hTrx1. Therefore, it was confirmed that the antibodies B266-1 and B264 are most likely to share an M4 site of the binding sites.

In addition, a microarray analysis was performed using 108 peptides manufactured by overlapping the amino acid sequence of a hTrx1 protein by one amino acid residue (FIGS. 19 and 20), and epitopes of the antibodies B266-1 and B264 were identified through heatmap evaluation, as shown in Table 25 (FIGS. 21A to 21D and 22A to 22F).

The present invention also provides a nucleic acid molecule encoding the above-described epitope of the Trx1 antigen, a recombinant vector containing the same, and a host cell containing the recombinant vector.

The nucleic acid molecule of the epitope of the Trx1 antigen according to the present invention may consist of any one amino acid sequence selected from the group consisting of SEQ ID NOs: 32 to 34 and 172 to 176.

Descriptions of the nucleic acid molecule encoding the above-described epitope, the recombinant vector containing the same, and the host cell containing the recombinant vector are the same as those of the antibody of the present invention described above, and thus will be omitted.

The present invention also provides a method of preparing a monoclonal antibody specifically binding to thioredoxin-1 or an antigen-binding fragment thereof, which includes culturing the host cells.

The culture of host cells to prepare an antibody or antigen-binding fragment thereof may be performed in a suitable medium known in the art under culture conditions. The culture process may be easily adjusted according to a strain by one of ordinary skill in the art. Cell culture is classified by suspension culture or attachment culture depending on a growth method, and batch culture, fed-batch culture or continuous culture according to a culture method. The medium used in culture has to suitably satisfy requirements for specific strains.

The medium used in animal cell culture includes various carbon sources, nitrogen sources, and trace elements. Examples of carbon sources used herein may be carbohydrates such as glucose, sucrose, lactose, fructose, maltose, starch and cellulose, lipids such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used independently or in combination. Examples of nitrogen sources used herein include organic nitrogen sources such as peptones, yeast extracts, beef stock, malt extracts, corn steep liquor (CSL) and soybean powder, and inorganic nitrogen sources such as urea, ammonium sulfate, ammonium chloride, ammonium phosphate, ammonium carbonate and ammonium nitrate. These nitrogen sources may be used independently or in combination. The medium may include potassium dihydrogen phosphate, dipotassium hydrogen phosphate and a corresponding sodium-containing salt as a phosphorus source. In addition, the medium may contain a metal salt such as magnesium sulfate or iron sulfate. In addition, an amino acid, a vitamin, and a suitable precursor may be included.

During culture, compounds such as ammonium hydroxide, potassium hydroxide, ammonia, phosphoric acid and sulfuric acid may be added to a cell culture by a suitable method to adjust a pH of the cell culture. In addition, the generation of bubbles may be inhibited using a foaming agent such as fatty acid polyglycol ester during culture. In addition, to maintain an aerobic condition of the cell culture, oxygen or an oxygen-containing gas (e.g., air) is injected into the cell culture. The temperature of the cell culture is generally 20 to 45° C., and preferably 25 to 40° C.

The antibody obtained by culturing host cells may be used without purification, or may be used by purification with high purity using various conventional methods, for example, dialysis, salt precipitation, and chromatography. Among these methods, chromatography is most widely used, and the types and order of columns may be selected for ion exchange chromatography, size exclusion chromatography, or affinity chromatography according to the characteristic of an antibody or a culture method.

The present invention provides a breast cancer diagnostic kit which includes the monoclonal antibody of the present invention or antigen-binding fragment thereof, and a method of providing information necessary for breast cancer diagnosis using the same.

The term "diagnosis" used herein refers to confirmation of the presence or feature of a pathological state. For the purpose of the present invention, diagnosis is to confirm whether breast cancer occurs or not.

The thioredoxin-1 protein is a breast cancer diagnostic marker, and highly expressed in breast cancer tissue, compared with normal breast tissue.

According to an exemplary embodiment of the present invention, the breast cancer diagnostic kit may be an enzyme linked immunosorbent assay (ELISA) kit, and preferably, one or more selected from the group consisting of direct ELISA, indirect ELISA, direct sandwich ELISA and indirect sandwich ELISA. In an exemplary embodiment of the present invention, two types of antibodies included in the sandwich ELISA kit include a monoclonal antibody B266-1 as a coating antibody, and a monoclonal antibody B264 as a detection antibody.

The breast cancer diagnostic kit of the present invention may further include a tool or reagent known in the art, which is used in immunological analysis, in addition to an antibody against Trx1.

Here, the immunological analysis may be carried out with any of the methods capable of measuring the binding of an antibody to an antigen. Such methods are known in the art include, for example, western blotting, ELISA, radioimmunoprecipitation, radial immunodiffusion, an immunofluorescence assay, immunoblotting, Ouchterlony immunodiffusion, rocket immunoelectrophoresis, immunohistochemical staining, an immunoprecipitation assay, a complement fixation assay, an immunochromatographic assay, FACS, and a protein chip assay, but the present invention is not limited thereto.

As a tool or reagent used in immunological analysis, a suitable carrier or support, a marker capable of producing a detectable signal, a solubilizer, a cleaning agent, or a stabilizer may be included. When a marker is an enzyme, suitable carriers include a substrate capable of measuring enzyme activity, a suitable buffer solution, a secondary antibody labeled with a chromogenic enzyme or a fluorescent material, a chromogenic substrate or a reaction stopping agent, but the present invention is not limited thereto.

The antibody against Trx1 included in the kit of the present invention is preferably fixed to a suitable carrier or support using various methods disclosed in a document, and examples of suitable carriers and supports include PBS, polystyrene, polyethylene, polypropylene, polyester, polyacrylonitrile, a fluorine resin, agarose, cellulose, nitrocellulose, dextran, Sephadex, Sepharose, a liposome, carboxymethyl cellulose, polyacrylamide, polystyrene, gabbro, filter paper, an ion exchange resin, a plastic film, a plastic tube, a polyamine-methyl vinyl-ether-maleic acid copolymer, an amino acid copolymer, an ethylene-maleic acid copolymer, nylon, a metal, glass, a glass bead, and a magnetic particle. Other solid supports include a cell culture plate, an ELISA plate, a tube and a polymer film. The support may have any possible shape, for example, a spherical (bead), cylindrical (test tube or the inside of well), or a planar (sheet or test strip) shape.

The marker capable of producing a detectable signal is able to qualitatively or quantitatively measure the formation of an antigen-antibody complex, and may be, for example, an enzyme, a fluorescent material, a ligand, a luminous material, a microparticle, a redox molecule or a radioisotope. As an enzyme, β-glucuronidase, β-D-glucosidase, a urease, a peroxidase (e.g., horseradish peroxidase), alkaline phosphatase, acetylcholinesterase, glucose oxidase, a hexokinase, malate dehydrogenase, glucose-6-phosphate dehydrogenase, invertase, or a luciferase may be used. As a fluorescent material, fluorescein, isothiocyanate, rhodamine, phycoerythrin, phycocyanin, allophycocyanin, or fluorescein isothiocyanate may be used. As a ligand, a biotin derivative may be used, and as a luminous material, acridinium ester or a luciferin may be used. As a microparticle, colloidal gold or colored latex may be used, and as a redox molecule, ferrocene, a ruthenium complex, a viologen, a quinone, a Ti ion, a Cs ion, diimide, 1,4-benzoquinone or hydroquinone may be used. As a radioisotope, $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, or $^{186}$Re may be used. However, other than the materials listed above, any one capable of being used in immunological analysis may be used.

As an enzyme chromogenic substrate, for example, when horseradish peroxidase (HRP) is selected as an enzyme marker, a solution containing 3-amino-9-ethylcarbazole, 5-aminosalicylic acid, 4-chloro-1-naphthol, o-phenylenediamine, 2,2'-azino-bis(3-ethylbenzothiazoline-6-sulfonic acid), 3,3-diaminobenzidine, 3,3',5,5'-tetramethylbenzidine, o-dianisidine or 3,3-dimethoxybenzidine may be used as a substrate. In addition, when an alkaline phosphatase is selected as an enzyme marker, a solution containing 5-bromo-4-chloro-3-indolyl phosphate, nitroblue tetrazolium or p-nitrophenyl phosphate may be used as a substrate. In addition, when β-D-galactosidase is selected as an enzyme marker, a solution containing o-nitrophenyl-β-D-galactoside or 5-bromo-4-chloro-3-indolyl-β-D-galactopyranoside may be used as a substrate. Other than these, various enzymes and enzyme chromogenic substances, which are known in the art, may be used.

According to an exemplary embodiment of the present invention, the method of providing information necessary for breast cancer diagnosis of the present invention may be performed with the following steps:

(a) bringing any one type of monoclonal antibody of the present invention or antigen-binding fragment thereof into contact with a biological sample isolated from a subject suspected of having breast cancer;

(b) measuring an expression level of the thioredoxin-1 protein binding to the monoclonal antibody or an antigen-binding fragment thereof in the biological sample through the formation of an antigen-antibody complex; and (c) comparing the expression level of the thioredoxin-1 protein, measured in step (b) with that of a control and, if the protein expression level is higher than that of the control, determining the subject to be a breast cancer patient.

According to another exemplary embodiment of the present invention, a method of providing information necessary for the diagnosis of breast cancer may be performed with the following steps:
(a) coating a solid support with a monoclonal antibody or an antigen-binding fragment thereof, including light chains CDR1 to CDR3 and heavy chains CDR1 to CDR3 of antibody B266 or B266-1, a monoclonal antibody or an antigen-binding fragment thereof, including a light chain variable region and a heavy chain variable region of antibody B266 or B266-1, or antibody B266 or B266-1 or an antigen-binding fragment thereof;
(b) applying a biological sample isolated from a subject suspected of having breast cancer to the coated solid support;
(c) removing an unbound sample;
(d) applying a monoclonal antibody or an antigen-binding fragment thereof, including light chains CDR1 to CDR3 and heavy chains CDR1 to CDR3 of antibody B264, a monoclonal antibody or an antigen-binding fragment thereof, including a light chain variable region and a heavy chain variable region of antibody B264, or antibody B264 or an antigen-binding fragment thereof to the solid support;
(e) removing an unbound monoclonal antibody or antigen-binding fragment thereof;
(f) measuring an expression level of Trx1 protein; and
(g) comparing the expression level of the Trx1 protein, measured in Step (f), with that of a control, and, if the protein expression level is higher than that of the control, determining the subject to be a breast cancer patient.

The term "isolated biological sample" used herein includes tissue (breast tissue), cells (breast cells), whole blood, plasma, serum, blood, saliva, synovial fluid, urine, sputum, lymphatic fluid, cerebrospinal fluid, a tissue autopsy sample (brain, skin, lymph nodes, spinal cord or the like), a cell culture supernatant, or ruptured eukaryotic cells, which is different in expression level of the Trx1 protein, which is a breast cancer marker, and includes a sample derived from a primary lesion or metastatic lesion. These biological samples, which are manipulated or not manipulated, may be reacted with the monoclonal antibody of the present invention to confirm an expression level of the Trx1 protein.

The term "subject" used herein includes mammals including a cow, a pig, sheep, a chicken, a dog and a human, birds, etc., and any subject suspected of having breast cancer without limitation.

Hereinafter, the present invention will be described in detail with reference to examples to help in understanding the present invention. However, examples according to the present invention may be modified into a variety of different forms, and it should not be construed that the scope of the present invention is limited to the following examples. The examples of the present invention are provided to more completely explain the present invention to those of ordinary skill in the art.

EXAMPLES

Example 1

Preparation of Human Thioredoxin-1 (Trx1) Antigen
1-1. Preparation of Trx1 Expression Vector
A gene was synthesized based on the *E. coli* codon usage to express the gene encoding the human thioredoxin-1 protein in *E. coli*. A sequence of the synthesized human thioredoxin-1 gene is shown in Table 1 below.

TABLE 1

| | Base sequence |
|---|---|
| Trx 1 gene | ATGGTCAAACAGATCGAATCAAAAACCGCATTTCAAGAA GCCCTGGACGCCGCTGGTGACAAACTGGTCGTGGTGGAC TTTAGTGCTACCTGGTGCGGCCCGTGTAAAATGATTAAA CCGTTTTTCCATAGCCTGTCTGAAAAATACAGTAACGTT ATCTTTCTGGAAGTGGATGTTGATGACTGCCAGGACGTC GCGAGCGAATGCGAAGTGAAATGTATGCCGACGTTCCAG TTTTTCAAAAAAGGTCAAAAAGTCGGTGAATTTAGCGGT GCCAACAAAGAAAAACTGGAAGCCACGATTAACGAACTG GTG (SEQ ID NO: 29) |

A primer sequence used to amplify the human thioredoxin-1 gene is shown in Table 2 below.

TABLE 2

| hTrx1-For | TAATGGTCAAACAGATCGAATC (SEQ ID NO: 30) |
|---|---|
| hTrx1-Rev | CACCAGTTCGTTAATCGTGGTAATGAAAGCT (SEQ ID NO: 31) |

To amplify a gene for cloning in a plasmid, a polymerase chain reaction (PCR) was performed. 10 pmol of a gene synthesized as a template, 10 pmol each of primers (hTrx1-For and hTrx1-Rev), dNTPs (each 2.5 mM), Exprime taq polymerase, and a buffer solution were mixed. This solution was reacted for 35 cycles at 95° C. for 2 minutes, at 95° C. for 30 seconds, at 55° C. for 30 seconds, and at 70° C. for 20 seconds, and further reacted at 70° C. for 2 minutes, and then the reaction was terminated. The amplified gene was purified, and then to clone an EcoRV site present in the multi-cloning site (MCS) of a pUC57 plasmid, the plasmid was treated with the corresponding restriction enzyme and purified. The plasmid treated with the purified gene and the restriction enzyme, a ligase and a buffer solution were mixed and reacted. To transform *E. coli* DH5α with the plasmid, a *E. coli* DH5α competent cell line was warmed at 4° C., mixed with a plasmid-mixed solution, and reacted at 4° C. for 30 minutes. After the reaction, the cells were subjected to heat shock at 42° C. for 30 seconds, stabilized at 4° C. for 2 minutes, dispensed on a Luria-Bertani (LB) solid medium containing an antibiotic (50 ug/mL of ampicillin) for uniform absorption, and cultured at 37° C. for 16 hours or more. A plasmid having the human thioredoxin-1 gene was screened from colonies grown in the cultured medium.

1-2. Trx1 Expression and Purification
The screened plasmid having the human thioredoxin-1 gene was purified, and then to express the protein, an *E. coli* BL21 strain was transformed with the purified plasmid according to the method described above. To express the thioredoxin-1 protein from the transformed strain, the strain was cultured in an LB broth containing an antibiotic to $OD_{600}=0.5$ at 37° C., and further cultured for 3 hours by adding isopropyl 3-D-thiogalactopyranoside (IPTG) so that a concentration became 1 mM. Afterward, SDS-PAGE was performed to confirm protein expression. To purify the protein, the obtained cell line was disrupted using ultrasonication and then centrifuged (12,000 rpm, 30 min, 4° C.), thereby obtaining a supernatant. A commercially available anti-thioredoxin I antibody (LF-MA0055, Abfrontier) was added to the obtained supernatant to bind to the expressed thioredoxin-1, protein A/G PLUS-agarose (sc-2003, Santa Cruz) which bound to the antibody was added to react therewith, and then centrifugation and purification were performed. Afterward, the purity and molecular weight of the resulting product were confirmed through SDS-PAGE.

Example 2

Production and Purification of Trx1-Specific Monoclonal Antibody 2-1. Immunization of Mouse The purified human thioredoxin-1 protein was mixed with an adjuvant and then injected into a mouse (BALB/c), and the mouse blood was collected and subjected to ELISA to confirm antibody production. After two immunizations, it was confirmed that an antibody titer (1:5,000) increases properly.

2-2. Cell Fusion and Preparation of Hybridoma

A B lymphocyte was isolated from the spleen extracted from the immunized mouse, and fused with cultured myeloma cells (sp2/0). The fused cells were cultured in a medium (HAT medium) containing hypoxanthine, aminopterine and thymidine, and cells (hybridomas) in which only a myeloma cell and a B lymphocyte are fused were selectively cultured.

2-3. Selection of Hybridoma Cells Producing Trx1-Specific Monoclonal Antibody

In the obtained hybridoma cells, three types of antibodies that react with the human thioredoxin-1 protein were confirmed through ELISA. The hybridoma producing an antibody that reacts with an antigen was selected from the ELISA-positive cells using a limiting dilution method.

2-4. Production and Purification of Monoclonal Antibody

The obtained three types of hybridomas were injected into mice, and then ascites was obtained from each mouse and purified using protein A affinity chromatography. The purified antibody was identified by SDS-PAGE.

Example 3

Identification of Isotype of Monoclonal Antibody

The three antibody isotypes obtained in Example 2 were confirmed using a Rapid ELISA Mouse mAbs Isotyping Kit (Pierce, Cat. 37503).

As a result, as shown in FIG. 1(b), it was confirmed that the heavy chain of a monoclonal antibody 2B4 is IgG1, the heavy chain of a monoclonal antibody 8F3 is IgG12a, and the heavy chain of a monoclonal antibody 9G7 is IgG2b, and the light chains are all kappa types.

Example 4

Analyses of Amino Acid Sequences of Monoclonal Antibodies 9G7(AB1) and 2B4(AB2)

The heavy chain and light chain amino acid sequences of the monoclonal antibodies 9G7(AB1) and 2B4(AB2) of the three types of monoclonal antibodies obtained in Example 2 were analyzed. As a sequence capable of being fused with an Fc region, which is suitable for back-translation and recombination expression, an amino acid sequence was determined. The sequence determined by IMTG gap alignment was aligned, and hypermutated and complete CDR3 parts were found using a hypermutation table. The sequences were identified using accurate mass peptide maps (FIGS. 2 and 3), and hypermutation and CDR3s were confirmed using MS/MS spectra.

Example 5

Comparison of Affinity and Determination of Antibody Using ELISA

A hypermutation-available position was determined in the amino acid sequence obtained through the above-described process, and therefore, genes were synthesized by altering amino acid sequences of four types (B266, B297, B268 and B269) of 9G7(AB1) and two types (B264 and B265) of 2B4(AB2). The six types of antibodies obtained above (B264~B269) were expressed, and then affinity of each antibody to an antigen was confirmed through ELISA (the numbers after "T" in Tables 3 to 5 represent production batch numbers, respectively).

Affinities to three types of antigens, that is, naked Trx1, Fc-binding Trx1(Trx1-Fc) and His-tagged Trx1 (Trx1-His) were determined through direct ELISA, and the results are sequentially shown in Tables 3 to 5. As shown in Tables 3 to 5, B264 as IgG1(κ) and B266 as IgG2b(κ) exhibited the highest affinity to three types of antigens.

TABLE 3

Results of reactions to naked Trx1 antigens

| Antibody ID | 5000X(OD Value) |
| --- | --- |
| AB264-T150514-7 | 2.0575 |
| B265-T150514-10 | 1.3225 |
| AB264-T150514-8 | 1.1635 |
| B265-T150514-9 | 0.9515 |
| B267-T150519-5 | 0.8155 |
| B269-T150519-9 | 0.735 |
| B268-T150519-8 | 0.716 |
| B268-T150519-7 | 0.670 |
| B266-T150519-3 | 0.6625 |
| B266-T150519-4 | 0.6615 |
| B269-T150519-10 | 0.626 |
| B267-T150519-6 | 0.522 |

TABLE 4

Results of reactions to Trx1-Fc antigens

| Antibody ID | 5000X(OD Value) |
| --- | --- |
| AB264-T150514-7 | 1.171 |
| AB264-T150514-8 | 0.494 |
| B265-T150514-10 | 0.378 |
| B265-T150514-9 | 0.273 |
| B266-T150519-3 | 0.198 |
| B266-T150519-4 | 0.181 |
| B267-T150519-5 | 0.043 |
| B267-T150519-6 | 0.023 |
| B268-T150519-8 | 0.015 |
| B268-T150519-7 | 0.003 |
| B269-T150519-9 | 0.002 |
| B269-T150519-10 | −0.001 |

TABLE 5

Results of reactions to Trx1-His antigens

| Antibody ID | 5000X(OD Value) |
| --- | --- |
| AB264-T150514-7 | 1.996 |
| B265-T150514-10 | 1.465 |
| AB264-T150514-8 | 1.142 |
| B265-T150514-9 | 1.03 |
| B267-T150519-5 | 0.857 |
| B268-T150519-8 | 0.783 |
| B269-T150519-9 | 0.77 |

TABLE 5-continued

Results of reactions to Trx1-His antigens

| Antibody ID | 5000X(OD Value) |
|---|---|
| B268-T150519-7 | 0.761 |
| B269-T150519-10 | 0.717 |
| B266-T150519-3 | 0.696 |
| B266-T150519-4 | 0.667 |
| B267-T150519-6 | 0.554 |

The amino acid sequences of the antibodies B264 and B266 with high affinity are shown in Table 6 below.

TABLE 6

| | Amino acid sequence |
|---|---|
| B264 light chain | DVLMTQTPLSLPVSLGDQASISCRSSQSIVHSNGNTY LEWYLQKPGQSPKLLIYKVSNRFSGVPDRFSGSGSGT DFTLKISRVEAEDLGVYYCFQGSHVPYTFGGGTKLEI KRADAAPTVSIFPPSSEQLTSGGASVVCFLNNFYPKD INVKWKIDGSERQNGVLNSWTDQDSKDSTYSMSSTLT LTKDEYERHNSYTCEATHKTSTSPIVKSFNRNEC (SEQ ID NO: 17) |
| B264 heavy chain | QVQLQQSGAELARPGASVKMSCKASGYTFTSYTMHWV KQRPGQGLEWIGYINPTSDYTNYNQKFKDKATLTADK SSSTAYMQLSSLTSEDSAVYFCASEGGFLYYFDYWGQ GTTLTVSSASTTPPSVYPLAPGSAAQTNSMVTLGCLV KGYFPEPVTVTWNSGSLSSGVHTFPAVLQSDLYTLSS SVTVPSSTWPSETVTCNVAHPASSTKVDKKIVPRDCG CKPCICTVPEVSSVFIFPPKPKDVLTITLTPKVTCVV VDISKDDPEVQFSWFVDDVEVHTAQTQPREEQFNSTF RSVSELPIMHQDWLNGKEFKCRVNSAAFPAPIEKTIS KTKGRPKAPQVYTIPPPKEQMAKDKVSLTCMITDFFP EDITVEWQWNGQPAENYKNTQPIMDTDGSYFVYSKLN VQKSNWEAGNTFTCSVLHEGLHNHHTEKSLSHSPGK (SEQ ID NO: 18) |
| B266 light chain | QIVLTQSPAIMSASPGEKVTMTCSASSRISYMYWYQQ KPGTSPKRWIYDTSKLASGVPARFSGSGSGTSYSLTI STMEAEDAATYYCHQRSSYPTFGAGTKLELKRADAAP TVSIFPPSSEQLTSGGASVVCFLNNFYPKDINVKWKI DGSERQNGVLNSWTDQDSKDSTYSMSSTLTLTKDEYE RHNSYTCEATHKTSTSPIVKSFNRNEC (SEQ ID NO: 19) |
| B266 heavy chain | EVQLQQSGAELVKPGASVKLSCTASGFNIKDTFMHWV KQRPEQGLEWIGRIDPANGNTKYDPKFQGKATITADT SSNTAYLQLSSLTSEDTAVYYCALLQYSAMDYWGQGT SVTVSSAKTTPPSVYPLAPGCGDTTGSSVTLGCLVKG YFPESVTVTWNSGSLSSSVHTFPALLQSGLYTMSSSV TVPSSTWPSQTVTCSVAHPASSTTVDKKLEPSGPIST INPCPPPCKECHKCPAPNLEGGPSVFIFPPNIKDVLMI SLTPKVTCVVVDVSEDDPDVQISWFVNNVEVHTAQTQ THREDYNSTIRVVSTLPIQHQDWMSGKEFKCKVNNKD LPSPIERTISKIKGLVRAPQVYILPPPAEQLSRKDVS LTCLVVGFNPGDISVEWTSNGHTEENYKDTAPVLDSD GSYFIYSKLNMKTSKWEKTDSFSCNVRHEGLKNYYLK KTISRSPG (SEQ ID NO: 20) |

Example 6

Production of Antibodies B264 and B266

6-1. Preparation of Plasmids Expressing Antibodies B264 and B266

Since the amino acid sequences of the antibodies B264 and B266 are identified as shown in Table 6, genes corresponding to the light chain and heavy chain of the respectively antibodies can be chemically synthesized. The synthesized gene sequences are shown in Table 7 below. The synthesized genes were cloned in pcDNA3.0.

TABLE 7

| | Gene sequence |
|---|---|
| B264 light chain | GACGTGCTGATGACACAGACACCACTCAGCCTCCCTGTGAGC CTGGGCGACCAGGCCTCTATTTCTTGCCGGTCTAGCCAGAGC ATCGTGCACTCCAACGGCAACACATACTTGGAGTGGTATCTA CAGAAGCCCGGCCAGTCCCCTAAGCTGCTGATATACAAGGT GTCTAACCGCTTCTCCGGCGTGCCCGACAGGTTCTCTGGCAG CGGCTCTGGCACCGACTTCACCCTCAAAATATCTAGGGTGGA GGCCGAGGACCTGGGCGTGTACTACTGCTTCCAGGGCTCCA CGTTCCATACACATTCGGCGGCGGCACAAAGTTGGAAATTA AGCGCGCTGACGCAGCCCCAACAGTGAGCATCTTTCCTCCAT CCTCTGAACAACTTACCTCTGGAGGAGCCTCTGTGGTGTGTT TCCTGAACAACTTCTACCCAAAGGACATCAATGTGAAGTGG AAGATTGATGGCTCTGAGAGACAGAATGGAGTGCTGAACTC CTGGACAGACCAGGACAGCAAGGACAGCACCTACAGTATGA GTAGCACCCTGACCCTGACCAAGGATGAATATGAGAGACAC AACTCCTACACTTGTGAGGCTACCCACAAGACCAGCACCAG CCCAATTGTCAAATCCTTCAACAGGAATGAGTGTTAA (SEQ ID NO: 21) |
| B264 heavy chain | CAGGTGCAGCTCCAGCAGTCCGGCGCCGAACTGGCCAGACCT GGCGCCAGCGTGAAGATGAGCTGCAAGGCCTCCGGCTACACA TTCACATCTTACACCATGCACTGGGTGAAGCAGAGACCCGGC CAGGGCCTGGAGTGGATTGGCTACATTAACCCAACATCCGAC TACACAAACTACAACCAGAAGTTCAAGGACAAGGCCACACTC ACCGCCGACAAGTCTTCTAGCACAGCCTACATGCAGCTGTCT AGCCTGACAAGCGAGGACTCTGCCGTGTACTTCTGCGCCTCT GAGGGCGGCTTCCTGTACTACTTCGACTACGGGGCCAGGGC ACCACCCTGACCGTGTCCTCTGCCAAAACGACACCCCCATCT GTCTATCCACTGGCCCCTGGATCTGCTGCCCAAACTAACTCC ATGGTGACCCTGGGATGCCTGGTCAAGGGCTATTTCCCTGAG CCAGTGACAGTGACCTGGAACTCTGGATCCCTGTCCAGCGGT GTGCACACCTTCCCAGCTGTCCTGCAGTCTGACCTCTACACT CTGAGCAGCTCAGTGACTGTCCCCTCCAGCACCTGGCCCAGC GAGACCGTCACCTGCAACGTTGCCCACCCGGCCAGCAGCACC AAGGTGGACAAGAAAATTGTGCCCAGGGATTGTGGTTGTAAG CCTTGCATATGTACAGTCCCAGAAGTATCATCTGTCTTCATC TTCCCCCCAAAGCCCAAGGATGTGCTCACCATTACTCTGACT CCTAAGGTCACGTGTGTTGTGGTAGACATCAGCAAGGATGAT CCCGAGGTCCAGTTCAGCTGGTTTGTAGATGATGTGGAGGTG CACACAGCTCAGACGCAACCCCGGGAGGAGCAGTTCAACAGC ACTTTCCGCTCAGTCAGTGAACTTCCCATCATGCACCAGGAC TGGCTCAATGGCAAGGAGTTCAAATGCAGGGTCAACAGTGCA GCTTTCCCTGCCCCCATCGAGAAAACCATCTCCAAAACCAAA GGCAGACCGAAGGCTCCACAGGTGTACACCATTCCACCTCCC AAGGAGCAGATGGCCAAGGATAAAGTCAGTCTGACCTGCATG ATAACAGACTTCTTCCCTGAAGACATTACTGTGGAGTGGCAG TGGAATGGGCAGCCAGCGGAGAACTACAAGAACACTCAGCCC ATCATGGACACAGATGGCTCTTACTTCGTCTACAGCAAGCTC AATGTGCAGAAGAGCAACTGGGAGGCAGGAAATACTTTCACC TGCTCTGTGTTACATGAGGGCCTGCACAACCACCATACTGAG AAGAGCCTCTCCCACTCTCCTGGTAAATAA (SEQ ID NO: 22) |
| B266 light chain | CAGATCGTGCTCACACAGTCTCCAGCCATCATGAGCGCCTCT CCTGGCGAGAAGGTGACAATGACCTGCTCTGCCTCTAGCCGC ATTTCTTACATGTACTGGTATCAGCAGAAGCCAGGCACCTCC CCTAAGAGGTGGATATACGACACATCCAAGCTGGCCTCCGG CGTGCCCGCCCGGTTCAGCGGCTCTGGCAGCGGCACAAGCT ACTCCCTGACAATTAGCACGATGGAGGCCGAGGACGCCGCC ACATACTACTGCCACCAGCGCTCGTCCTACCCAACATTCGGC GCCGGCACAAAATTGGAACTGAAGAGAGCTGACGCAGCCCC AACAGTGAGCATCTTTCCTCCATCCTCTGAACAACTTACCTC TGGAGGAGCCTCTGTGGTGTGTTTCCTGAACAACTTCTACCC AAAGGACATCAATGTGAAGTGGAAGATTGATGGCTCTGAGA GACAGAATGGAGTGCTGAACTCCTGGACAGACCAGGACAGC AAGGACAGCACCTACAGTATGAGTAGCACCCTGACCCTGAC CAAGGATGAATATGAGAGACACAACTCCTACACTTGTGAGG CTACCCACAAGACCAGCACCAGCCCAATTGTCAAATCCTTCA ACAGGAATGAGTGTTAA (SEQ ID NO: 23) |
| B266 heavy chain | GAGGTGCAGTTACAACAGTCCGGCGCCGAGCTAGTGAAGCCA GGCGCCAGCGTGAAGCTGTCTTGCACAGCCAGCGGCTTCAAC ATTAAGGACACCTTCATGCACTGGGTGAAGCAGAGACCTGAG CAGGGCTTAGAGTGGATTGGCCGGATCGACCCCGCCAACGGC AACACAAAGTACGACCCAAAGTTCCAGGGCAAGGCCACAATT ACCGCCGACACATCTTCCAACACAGCCTACCTCCAGCTGTCG TCTCTCACCAGCGAGGACACCGCCGTGTACTACTGCGCCCTG CTCCAGTACTCCGCGATGGACTACTGGGGCCAGGGCACATCT GTGACCGTGTCTAGCGCCAAGACCACCCCACCATCCGTGTAC |

TABLE 7-continued

Gene sequence

```
CCACTCGCCCCAGGCTGCGGCGACACCACAGGCTCTAGCGTG
ACACTGGGCTGCCTGGTGAAGGGCTACTTCCCCGAGTCTGTG
ACAGTGACCTGGAACTCTGGCTCTCTGTCTAGCTCTGTGCAC
ACCTTCCCCGCCCTGCTGCAATCCGGCCTGTACACAATGTCT
TCTTCTGTGACAGTGCCTAGCTCTACATGGCCATCTCAGACA
GTGACATGCTCTGTGGCCCACCCCGCCTCTAGCACAACCGTG
GACAAGAAGCTGGAGCCATCCGGCCCTATTTCTACAATTAAC
CCTTGCCCTCCTTGCAAAGAATGCCACAAGTGCCCCGCCCCA
AACCTGGAGGGCGGCCCTTCTGTGTTCATTTTCCCTCCTAAC
ATTAAGGACGTGCTGATGATCAGCCTCACCCCAAAGGTGACA
TGCGTGGTGGTGGACGTGTCCGAGGACGACCCTGACGTGCAG
ATTTCTTGGTTCGTGAACAACGTGGAGGTGCACACCGCCCAG
ACCCAGACCCACCGGGAGGACTACAACTCCACCATTCGGGTG
GTGTCTACACTGCCTATTCAGCACCAGGACTGGATGAGCGGC
AAAGAGTTCAAGTGCAAGGTGAACAACAAGGACCTGCCATCT
CCTATTGAGAACAATTTCTAAGATTAAGGGCCTGGTGCGC
GCCCCTCAGGTGTACATTCTGCCTCCTCCCGCCGAGCAGCTG
AGCCGGAAGGACGTGTCCCTCACATGCCTCGTGGTGGGCTTC
AACCCTGGCGACATTAGCGTGGAGTGGACATCTAACGGCCAC
ACAGAAGAAAACTACAAGGACACAGCCCCTGTGCTCGACTCC
GACGGCTCTTACTTCATATACTCTAAGCTGAACATGAAAACA
TCTAAGTGGGAAAAGACCGACTCTTTCTCTTGCAACGTGCGG
CACGAGGGCCTGAAGAACTACTACCTCAAGAAAACCATTAGC
AGAAGTCCAGGCTAA (SEQ ID NO: 24)
```

6-2. Expression and Purification of Antibodies B264 and B266

A HEK293 cell line was co-transfected with pcDNA3-SSJ11-L and pcDNA3-SSJ11-H to express a B264 antibody or pcDNA3-SSJ12-L and pcDNA3-SSJ12-H to express a B266 antibody, and cultured for 7 days. The cell line was cultured, and recombinant monoclonal antibodies secreted into the culture medium were collected and purified through protein A chromatography. An eluent containing the recombinant monoclonal antibodies was concentrated by ultrafiltration, and the antibodies were obtained with high purity using a 0.2-μm sterile filter.

Figure 6:
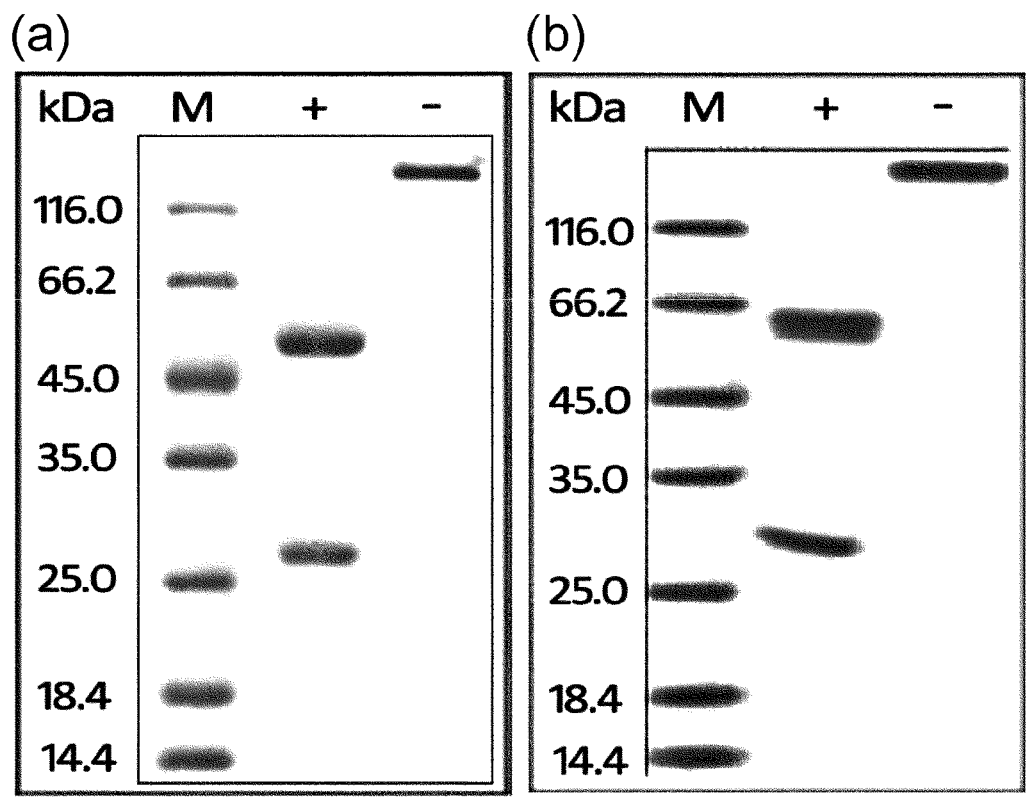
FIG. 6 shows results of identifying the reduced (+) and non-reduced (−) states of antibodies using SDS-PAGE, where (a) is the result for the antibody B264, and (b) is the result for the antibody B266.

The purity and size of the purified antibodies were determined through SDS-PAGE. As a result of SDS-PAGE, as shown in FIG. 6, it was confirmed that the antibodies B264 and B266 are expressed with sizes, for example, 47 kDa for the heavy chain and 25 kDa for the light chain under a reducing condition, and 150 kDa under a non-reducing condition, suggesting that the sizes correspond to estimated sizes.

Example 7

Confirmation of Pairing of Two Types of Monoclonal Antibodies Obtained Through Sandwich ELISA 100 μl of a coating buffer (0.015 M Na$_2$CO$_3$, 0.035 M NaHCO$_3$, 0.003 M NaN$_3$, pH9.6) and 100 ng of a coating antibody (B266) were mixed and dispensed to each well, and an O/N reaction was performed at 4° C. 200 μl of 1% BSA-containing PBS (PBSA; blocking buffer) per well was dispensed, and subjected to a reaction at room temperature for 60 minutes. Afterward, 20 μl of an antigen (50, 25, 12.5 or 0 ng) was dispensed, 80 μl of a detection antibody (biotin-labeled B264; B264-B) was dispensed, and the resulting mixture was reacted at 37° C. for 90 minutes. A reaction solution was removed, and washing was performed by dispensing 200 μl of PBS containing 0.05% Tween 20 (PBST; washing buffer) to each well. The above-described process was performed three times.

100 μl of streptavidin-HRP diluted 1:200 was treated in each well and reacted at 37° C. for 30 minutes. After a reaction solution was removed, washing was performed by dispensing 200 μl of PBS containing 0.05% Tween 20 (PBST; washing buffer) to each well. The above-described process was performed three times.

100 μl of a TMB solution was dispensed to each well and reacted under a dark condition at room temperature for 10 minutes, 100 μl of a 2.5M sulfuric acid solution (H$_2$SO$_4$; stop buffer) was treated in each well, and the result was confirmed at 450 nm.

As a result, as shown in Table 8, the reaction value increases according to the concentration of an antigen, showing the detection of the antigen by these antibodies. However, since the O.D. value is high when there is no antigen, a performance improvement experiment using an antibody is needed.

TABLE 8

Sandwich ELISA using B266 as coating antibody and B264 as detection antibody

| Trx1 (ng/mL) | 0 | 12.5 | 25 | 50 |
|---|---|---|---|---|
| O.D.$_{450nm}$ | 0.828 | 1.226 | 1.506 | 2.257 |

Example 8

Alteration of Isotype of Fc Part for Improving Antibody Performance

Since the expression system of an antibody is transient transfection using a recombinant plasmid, rather than a hybridoma, among these recombinant plasmids, a plasmid having a heavy chain was co-transfected with a plasmid having a different isotype of heavy chain. That is, a plasmid having a gene encoding a different heavy chain, rather than pcDNA3-SSJ12-H of pcDNA3-SSJ12-L and pcDNA3-SSJ12-H used to express 9G7(AB1), was co-transfected.

Figure 7:
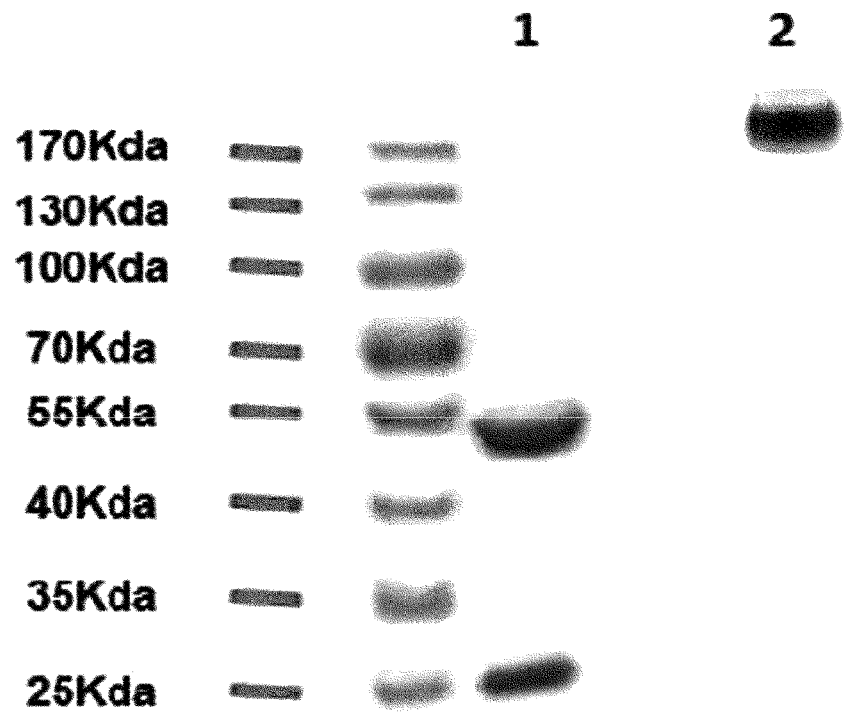
FIG. 7 shows results of identifying the reduced (+) and non-reduced (−) states of an antibody B266-1 using SDS-PAGE, in which the antibody B266-1 is prepared by modifying an Fc part of the antibody B266 to human IgG1.
Figure 8A:
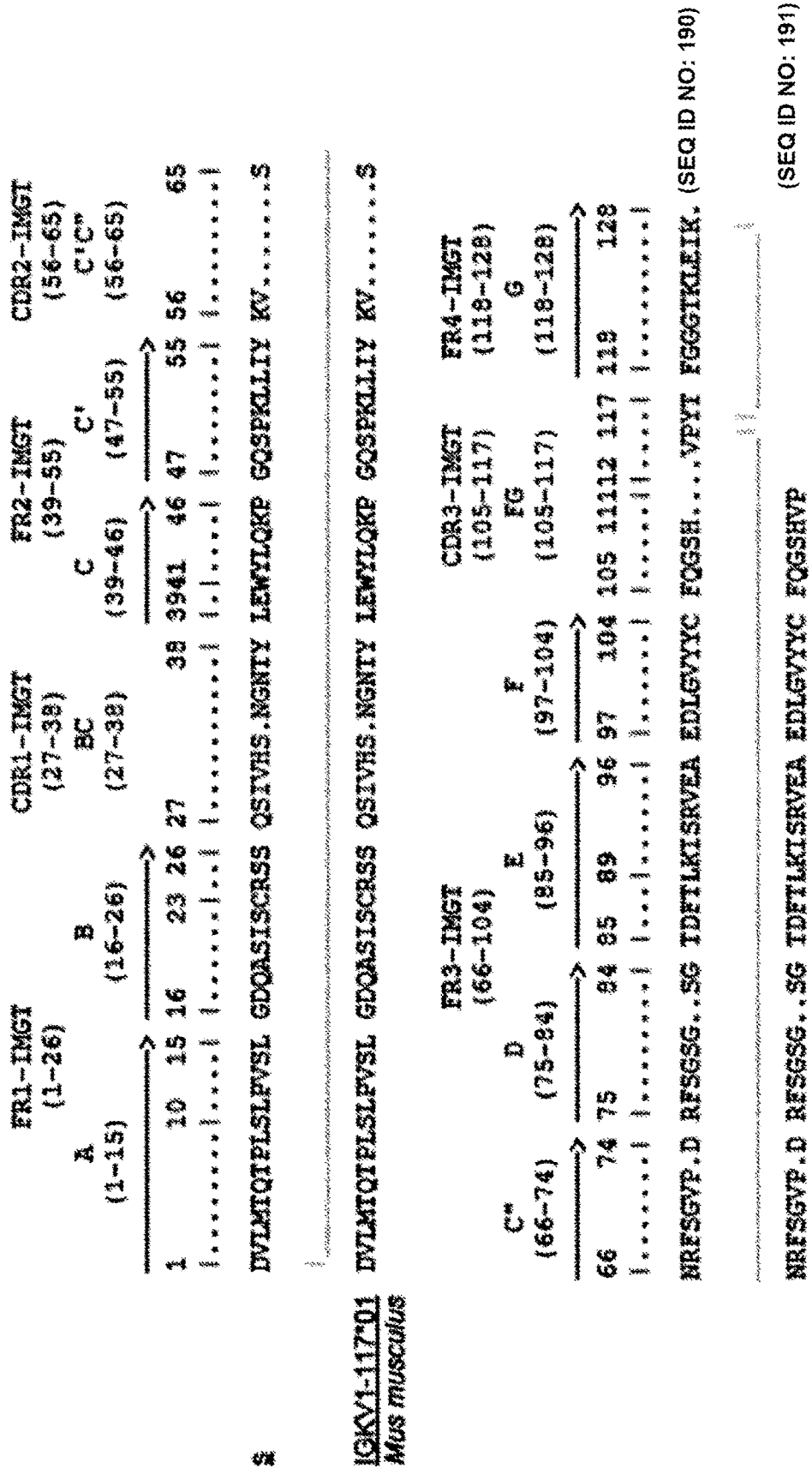
FIGS. 8A to 8D show results of IMTG gap alignment for a light chain and a heavy chain of antibody B266-1 and a light chain and a heavy chain of antibody B264 in order.
Figure 8B:
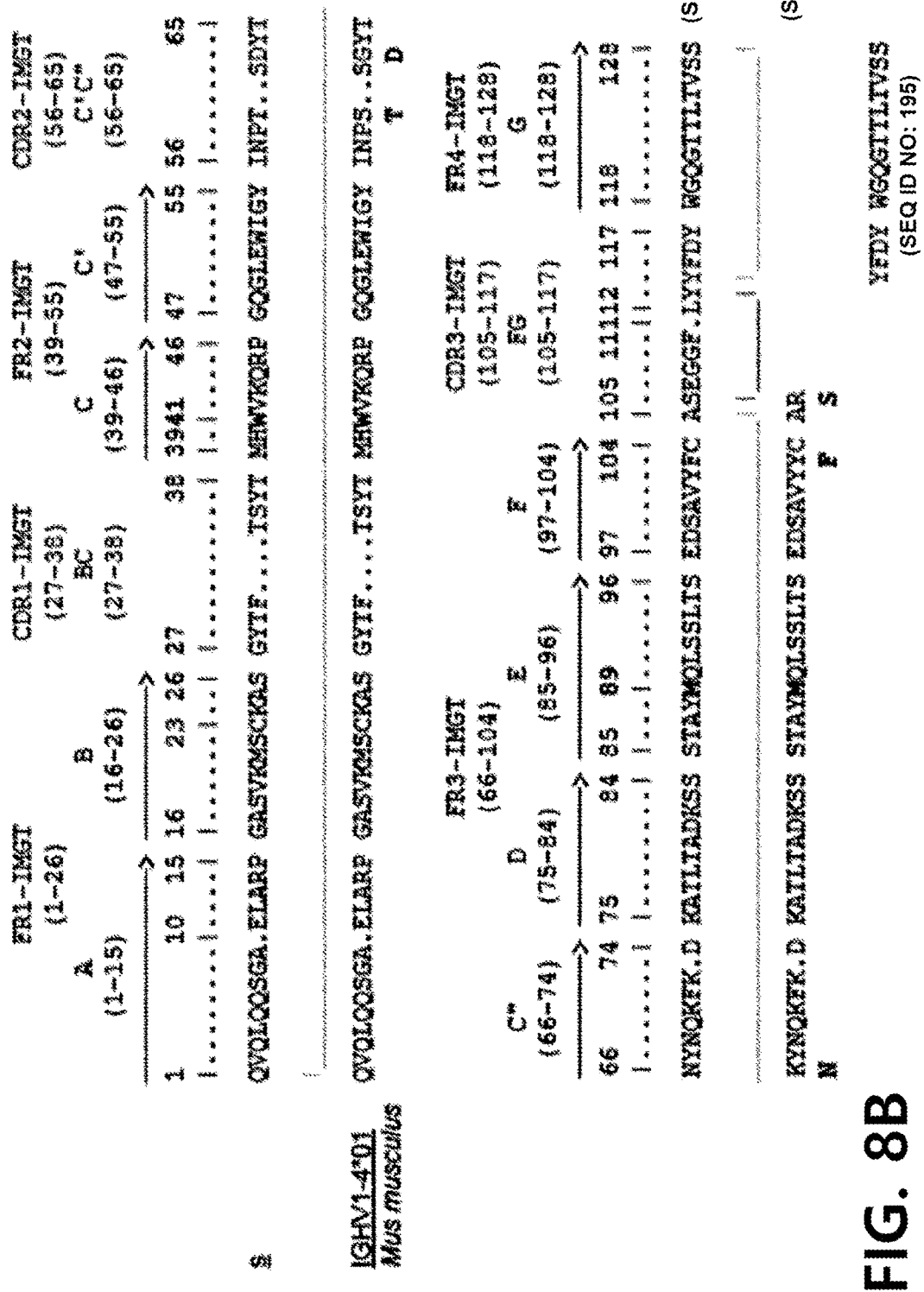
Figure 8C:
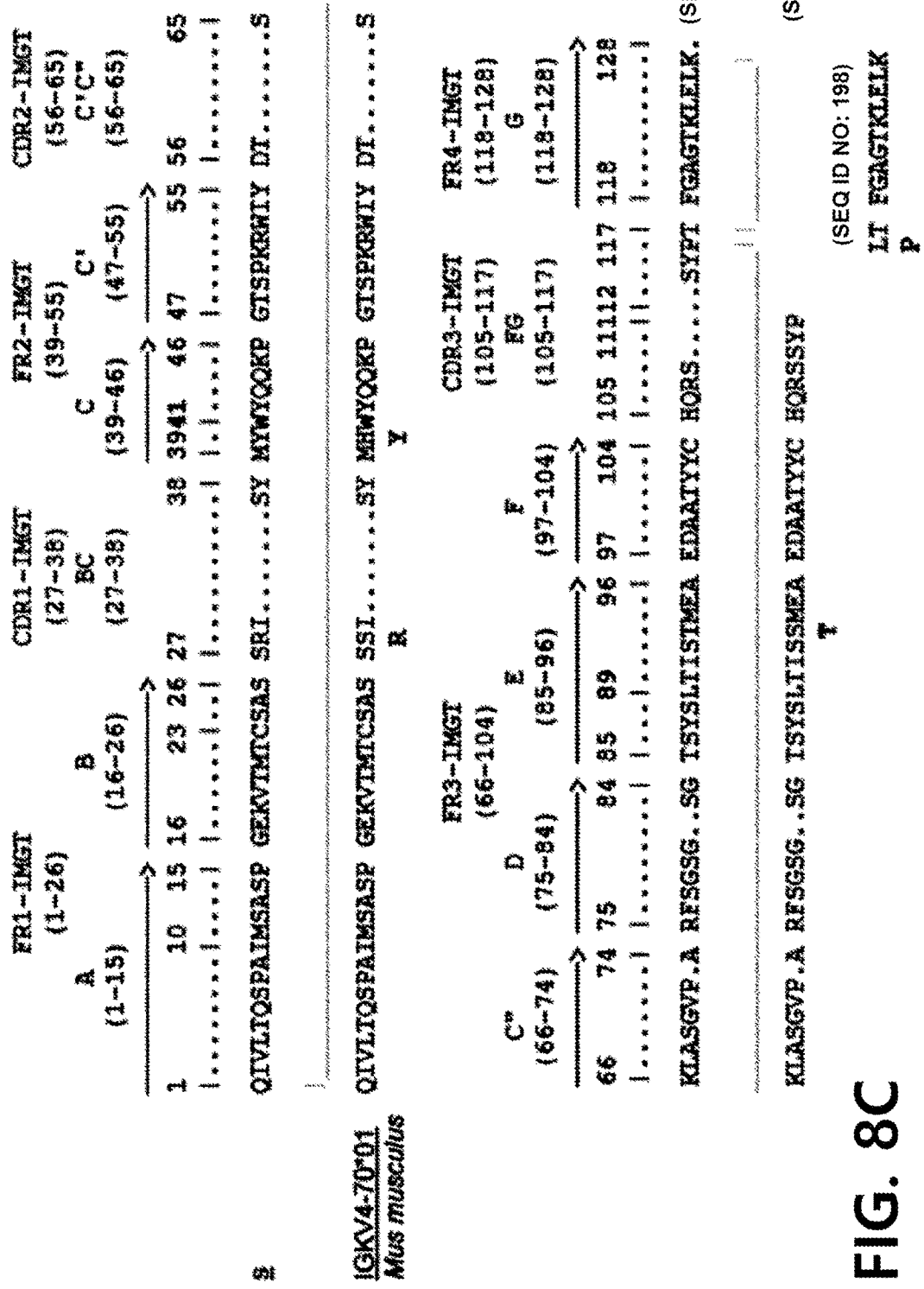
Figure 8D:
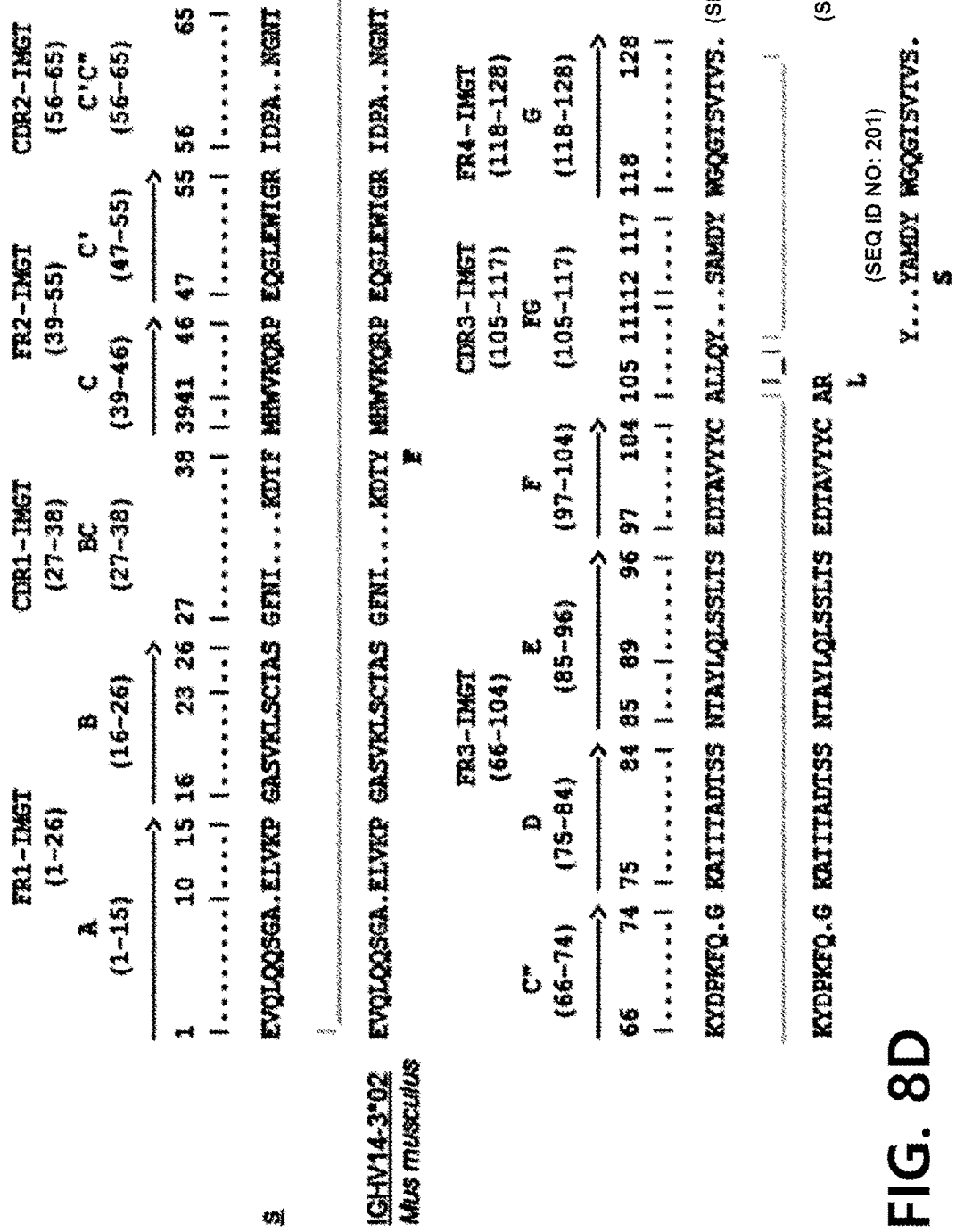

An antibody (B266-1) in which the Fc part of B266 is changed to human IgG1 was obtained by the above-described method. The characteristics of the antibody were determined through SDS-PAGE (FIG. 7).

CDR sequences of the finally selected monoclonal antibodies B264 and B266-1 were determined by fusion with an Fc region suitable for back translation and recombinant expression.

IMTG-gap alignment is IMTG database and "determined sequence" alignment, and the closest germline sequence and hypermutation were identified by a database search. The IMTG-gap alignment results for the light chain and heavy chain of each of the antibodies B266-1 and B264 are shown in FIG. 8A to 8D, amino acid sequences of light chains CDR1 to CDR3 and heavy chains CDR1 to CDR3 are shown in Table 9, and amino acid sequences of a light chain variable region and a heavy chain variable region are shown in Table 10. In addition, the amino acid sequences and gene sequences of the light chains and heavy chains of B266-1 are shown in Table 11.

TABLE 9

|  | Amino acid sequence |
|---|---|
| Light chain CDR1 of B264 | QSIVHSNGNTY (SEQ ID NO: 1) |
| Light chain CDR2 of B264 | KVS (SEQ ID NO: 2) |
| Light chain CDR3 of B264 | CFQGSHVPYT (SEQ ID NO: 3) |

TABLE 9-continued

| | Amino acid sequence |
|---|---|
| Heavy chain CDR1 of B264 | GYTFTSYT (SEQ ID NO: 4) |
| Heavy chain CDR2 of B264 | INPTSDYTN (SEQ ID NO: 5) |
| Heavy chain CDR3 of B264 | FCASEGGFLYYFDY (SEQ ID NO: 6) |
| Light chain CDR1 of B266-1 | SRISY (SEQ ID NO: 7) |
| Light chain CDR2 of B266-1 | DTS (SEQ ID NO: 8) |
| Light chain CDR3 of B266-1 | CHQRSSYPTF (SEQ ID NO: 9) |
| Heavy chain CDR1 of B266-1 | GFNIKDTF (SEQ ID NO: 10) |
| Heavy chain CDR2 of B266-1 | IDPANGNT (SEQ ID NO: 11) |
| Heavy chain CDR3 of B266-1 | CALLQYSAMDY (SEQ ID NO: 12) |

TABLE 10

| | Amino acid sequence |
|---|---|
| Light chain variable region of B264 | DVLMTQTPLSLPVSLGDQASISCRSSQSIVHSNGNT YLEWYLQKPGQSPKLLIYKVSNRFSGVPDRFSGSGS GTDFTLKISRVEAEDLGVYYCFQGSHVPYTFGGGTK LEIK (SEQ ID NO: 13) |
| Heavy chain variable region of B264 | QVQLQQSGAELARPGASVKMSCKASGYTFTSYTMHW VKQRPGQGLEWIGYINPTSDYTNYNQKFKDKATLTA DKSSSTAYMQLSSLTSEDSAVYFCASEGGFLYYFDY WGQGTTLTVSS (SEQ ID NO: 14) |
| Light chain variable region of B266-1 | QIVLTQSPAIMSASPGEKVTMTCSASSRISYMYWYQ QKPGTSPKRWIYDTSKLASGVPARFSGSGSGTSYSL TISTMEAEDAATYYCHQRSSYPTFGAGTKLELK (SEQ ID NO: 15) |
| Heavy chain variable region of B266-1 | EVQLQQSGAELVKPGASVKLSCTASGFNIKDTFMHW VKQRPEQGLEWIGRIDPANGNTKYDPKFQGKATITA DTSSNTAYLQLSSLTSEDTAVYYCALLQYSAMDYWG QGTSVTVSS (SEQ ID NO: 16) |

TABLE 11

| | Sequence |
|---|---|
| Amino acid sequence of B266-1 light chain | QIVLTQSPAIMSASPGEKVTMTCSASSRISYMYWYQQKP GTSPKRWIYDTSKLASGVPARFSGSGSGTSYSLTISTME AEDAATYYCHQRSSYPTFGAGTKLELKRADAAPTVSIFPP SDEQLKSGTASVVCLLNNFYPREAKVQWKVDNALQSGNS QESVTEQDSKDSTYSLSSTLTLSKADYEKHKVYACEVTH QGLSSPVTKSFNRGEC (SEQ ID NO: 25) |
| Amino acid sequence of B266-1 heavy chain | EVQLQQSGAELVKPGASVKLSCTASGFNIKDTFMHWVKQ RPEQGLEWIGRIDPANGNTKYDPKFQGKATITADTSSNT AYLQLSSLTSEDTAVYYCALLQYSAMDYWGQGTSVTVSS ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK (SEQ ID NO: 26) |
| Gene sequence of B266-1 light chain | CAGATCGTGCTCACACAGTCTCCAGCCATCATGAGCGCC TCTCCTGGCGAGAAGGTGACAATGACCTGCTCTGCCTCT AGCCGCATTTCTTACATGTACTGGTATCAGCAGAAGCCA GGCACCTCCCCTAAGAGGTGGATATACGACACATCCAAG CTGGCCTCCGGCGTGCCCGCCCGGTTCAGCGGCTCTGGC AGCGGCACAAGCTACTCCCTGACAATTAGCACGATGGAG GCCGAGGACGCCGCCACATACTACTGCCACCAGCGCTCG TCCTACCCAACATTCGGCGCCGGCACAAAATTGGAACTG AAGGTGGCTGCACCATCTGTCTTCATCTTCCCGCCATCT GATGAGCAGTTGAAATCTGGAACTGCCTCTGTTGTGTGC CTGCTGAATAACTTCTATCCCAGAGAGGCCAAAGTACAG TGGAAGGTGGATAACGCCCTCCAATCGGGTAACTCCCAG GAGAGTGTCACAGAGCAGGACAGCAAGGACAGCACCTAC AGCCTCAGCAGCACCCTGACGCTGAGCAAAGCAGACTAC GAGAAACACAAAGTCTACGCCTGCGAAGTCACCCATCAG GGCCTGAGCTCGCCCGTCACAAAGAGCTTCAACAGGGGA GAGTGTTAG (SEQ ID NO: 27) |
| Gene sequence of B266-1 heavy chain | GAGGTGCAGTTACAACAGTCCGGCGCCGAGCTAGTGAAG CCAGGCGCCAGCGTGAAGCTGTCTTGCACAGCCAGCGGC TTCAACATTAAGGACACCTTCATGCACTGGGTGAAGCAG AGACCTGAGCAGGGCTTAGAGTGGATTGGCCGGATCGAC CCCGCCAACGGCAACACAAAGTACGACCCAAAGTTCCAG GGCAAGGCCACAATTACCGCCGACACATCTTCCAACACA GCCTACCTCCAGCTGTCGTCTCTCACCAGCGAGGACACC GCCGTGTACTACTGCGCCCTGCTCCAGTACTCCGCGATG GACTACTGGGGCCAGGGCACATCTGTGACCGTGTCTAGA CCAAGGGCCCATCGGTCTTCCCCCTGGCACCCTCCTCCA AGAGCACCTCTGGGGGCACAGCGGCCCTGGGCTGCCTGG TCAAGGACTACTTCCCCGAACCGGTGACGGTGTCGTGGA ACTCAGGCGCCCTGACCAGCGGCGTGCACACCTTCCCGG CTGTCCTACAGTCCTCAGGACTCTACTCCCTCAGCAGCG TGGTGACCGTGCCCTCCAGCAGCTTGGGCACCCAGACCT ACATCTGCAACGTGAATCACAAGCCCAGCAACACCAAGG TGGACAAGAAAGTTGAGCCCAAATCTTGTGACAAAACTC ACACATGCCCACCGTGCCCAGCACCTGAACTCCTGGGGG GACCGTCAGTCTTCCTCTTTCCCCCAAAACCCAAGGACA CCCTCATGATCTCCCGGACCCCTGAGGTCACATGCGTGG TGGTGGACGTGAGCCACGAAGACCCTGAGGTCAAGTTCA ACTGGTACGTGGACGGCGTGGAGGTGCATAATGCCAAGA CAAAGCCGCGGGAGGAGCAGTACAACAGCACGTACCGTG TGGTCAGCGTCCTCACCGTCCTGCACCAGGACTGGCTGA ATGGCAAGGAGTACAAGTGCAAGGTCTCCAACAAAGCCC TCCCAGCCCCCATCGAGAAAACCATCTCCAAAGCCAAAG GGCAGCCCCGAGAACCACAGGTGTACACCCTGCCCCCAT CCCGGGAGGAGATGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACAAGA CCACGCCTCCCGTGCTGGACTCCGACGGCTCCTTCTTCC TCTACAGCAAGCTCACCGTGGACAAGAGCAGGTGGCAGC AGGGGAACGTCTTCTCATGCTCCGTGATGCATGAGGCTC TGCACAACCACTACACGCAGAAGAGCCTCTCCCTGTCTC CGGGTAAATGA (SEQ ID NO: 28) |

Example 9

Confirmation of Pairing of Monoclonal Antibodies B266-1 and B264 Obtained Through Sandwich ELISA 100 μl of a coating buffer and 100 ng of a coating antibody (B266-1) were mixed and dispensed to each well, and an O/N reaction was performed at 4° C. Washing was performed by dispensing 200 μl of a washing buffer. The above-described process was performed two times.

200 μl of PBSA was dispensed to each well and reacted at room temperature for 120 minutes, and then 20 μl of an antigen (25 or 0 ng) was dispensed, 80 μl of a detection antibody (B264-B) was dispensed, and a reaction was performed at 37° C. for 90 minutes. A reaction solution was removed, and then washing was performed by dispensing 200 µt of a washing buffer to each well. The above-described process was performed three times.

100 µt of streptavidin-HRP diluted 1:200 was treated in each well, a reaction was performed at 37° C. for 30 minutes, a reaction solution was removed, and then washing was performed by dispensing 200 µt of washing buffer to each well. The above-described process was performed three times.

100 µl of a TMB solution was dispensed to each well, a reaction was performed under a dark condition at room temperature for 10 minutes, 100 µl of a stop buffer was treated in each well, and the result was confirmed at 450 nm.

As a result, as shown in Table 12, it was confirmed that the antibodies are suitably reacted with antigens, and a blank value was decreased as compared with the antibodies used in Example 6.

TABLE 12

| Sandwich ELISA using B266-1 as coating antibody and B264 as detection antibody | | | | |
|---|---|---|---|---|
| Trx1 (ng/mL) | 0 | | 25 | |
| O.D.$_{450nm}$ | 0.425 | 0.415 | 1.571 | 1.426 |

Example 10

Analysis of Affinity of Monoclonal Antibody to Antigen

Two types of monoclonal antibodies specifically acting on the antigen Trx1 were expressed using a transient transfection system using a plasmid, and thus stably produced. To confirm the affinity to an antigen, analysis was performed through ELISA (FIG. 8(a)).

100 µl of a coating buffer and 100 ng of Trx1 were mixed and dispensed to each well, and then reacted at 4° C. for 16 hours or more. After the reaction solution was removed, 200 µl of PBSA was dispensed to each well and reacted at 37° C. for 120 minutes. After the reaction solution was removed, the produced antibody B266-1 or B264 was diluted 1/5 from 0.1 µM, and dispensed to each well at 100 µl, and then reacted at 37° C. for 120 minutes. After the reaction solution was removed, washing was performed by dispensing 200 µl of a washing buffer to each well. The above-described process was performed two times.

100 µl of human IgG-HRP (diluted to 1:4000) as the antibody B266-1 was reacted with 100 µl of mouse IgG-HRP (diluted to 1:4000) as the antibody B264 at 37° C. for 60 minutes. After the reaction solution was removed, washing was performed by dispensing 200 µl of a washing buffer to each well. The above-described process was performed three times.

100 µl of a TMB solution was dispensed to each well, a reaction was performed under a dark condition at room temperature for 10 minutes, 100 µl of a stop buffer was treated in each well, and the result was confirmed at 450 nm. The resulting values were analyzed using Prism (Graphpad) (FIG. 8(b)).

As a result of analyzing the affinity of the coating antibody B266-1 and the detection antibody B264, it was confirmed that a blank value is high due to the reactivity of B266-1, but B266-1 and B264 are increased in binding degree according to an increased concentration of an antigen. This shows that B266-1 and B264 are bound with an antigen. When an equilibrium dissociation constant ($K_D$) value is calculated through analysis using the Prism program, the $K_D$ of B266-1 was $1.1 \times 10^{-11}$, and the $K_D$ of B264 was $1.3 \times 10^{-10}$. When the $K_D$ value is between $10^{-10}$ and $10^{-12}$, it was evaluated that the antibody has a picomole (pM) level of sensitivity to an antigen, showing that B266-1 and B264 have a high level of sensitivity to an antigen.

Example 11

Sandwich ELISA of Serum of Breast Cancer Patient

Sandwich ELISA using a coating antibody (B266-1) was prepared in a process as follows.

A 1 µg/mL coating antibody solution was prepared by adding 100 mL of a coating buffer and 0.1 mL of 1 mg/mL B266-1. 100 µl of the prepared coating antibody solution was dispensed to each well of a 96-well plate, and reacted at 4° C. for 12 hours. The antibody solution was removed, and washing was performed by dispensing 200 µl of 0.05% PBST to each well. The washing was performed three times. 200 µl of PBSA was treated in each well, and a reaction (blocking process) was performed at 4° C. for 4 hours. The PBSA was removed, and then the 96-well plate was dried in a thermo-hygrostat (20° C., 30% R.H.) for 3 hours.

Afterward, the detection antibody (B264) was biotinylated with a process as follows.

Dimethyl sulfoxide (DMSO) is mixed with 20 mg/mL biotin-7-NHS, thereby preparing 2 mg/mL biotin-7-NHS. 15 µl (30 µg) of 2 mg/mL biotin-7-NHS was added to the 1 mg/mL B264 antibody, and reacted at 15 to 25° C. for 2 hours. A reaction solution was added to AMICON ultra-15 (Millipore), filled with a PBS solution to the final volume, and centrifuged at 3,600×g until it remained at 0.5 mL. The process was performed three times. The antibody solution (biotinylated B264; B264-B) remaining in the AMICON filter was transferred to a 1.5 mL tube, and filled with PBSA to the final concentration of 0.3 mg/mL.

Subsequently, human Trx1 antigen detection from the serum of a breast cancer patient was performed as follows.

A standard antigen solution was dispensed to the first column of a 96-well plate coated with a coating antibody. 20 µl of the serum obtained from a breast cancer was dispensed, and then 80 µl (0.3 mg/mL) of a B264-B solution was dispensed. Afterward, after a reaction at 37° C. for 60 minutes, an antigen-antibody reaction solution was removed, and then washing was performed by dispensing 200 µl of PBST to each well. The washing process was performed three times. 100 µl of a 1:400-dilution of streptavidin-HRP (R&D Systems) was dispensed, and a reaction was performed at 37° C. for 30 minutes. After the reaction, a reaction solution was removed, and washing was performed by dispensing 200 µl of PBST to each well. The washing process was performed three times. 100 µl of a TMB solution (Sure Blue) was treated, and a reaction was performed at room temperature for 15 minutes under a dark condition. 100 µl of a 2N $H_2SO_4$ solution was dispensed, and an absorbance was measured at 450 nm using a microplate reader.

Finally, ROC analysis was performed as follows.

Figure 9:
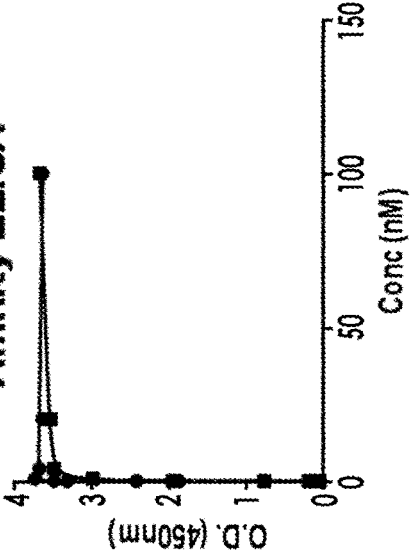
FIG. 9 shows results of analyzing the affinity of the antibodies B266-1 and B264, where (A) shows a reaction value according to an antibody concentration and a graph thereof, and (B) shows the result of analyzing the affinity of antibodies using a Prism program.

Sensitivity and specificity were calculated by analyzing a result of ELISA using monoclonal antibodies B266-1 and B264 against Trx1. When a cut-off value was 10.8 ng/mL, the sensitivity was 93.0%, and the sensitivity was 97.4% (FIG. 9).

Example 12

Comparative Analysis with Another ELISA Kit for Breast Cancer Diagnosis

In this example, to evaluate the performance of recombinant monoclonal antibodies B266-1 and B264, another ELISA kit for detecting another biomarker CA15-3 for breast cancer diagnosis was comparatively analyzed (Table 13).

As a result, as shown in Table 13, when a monoclonal antibody specifically binding to Trx1 is used, sensitivity and specificity were exceptionally higher than those of CA15-3.

TABLE 13

Comparison of kit of the present invention with AxSYM CA15-3 kit

|  | Trx1 | CA15-3 (AxSYM) |
|---|---|---|
| Sensitivity (%) | 93 | 54 |
| Specificity (%) | 97.4 | 94 |
| Test sample | Serum | Serum and plasma |

Example 13

Expression of *Chrysochloris asiatica* Trx1 Protein 13-1. Comparison of Sequences of Human Trx1 (hTrx1) and *Chrysochloris asiatica* Trx1 (CaTrx1)

Figure 10:
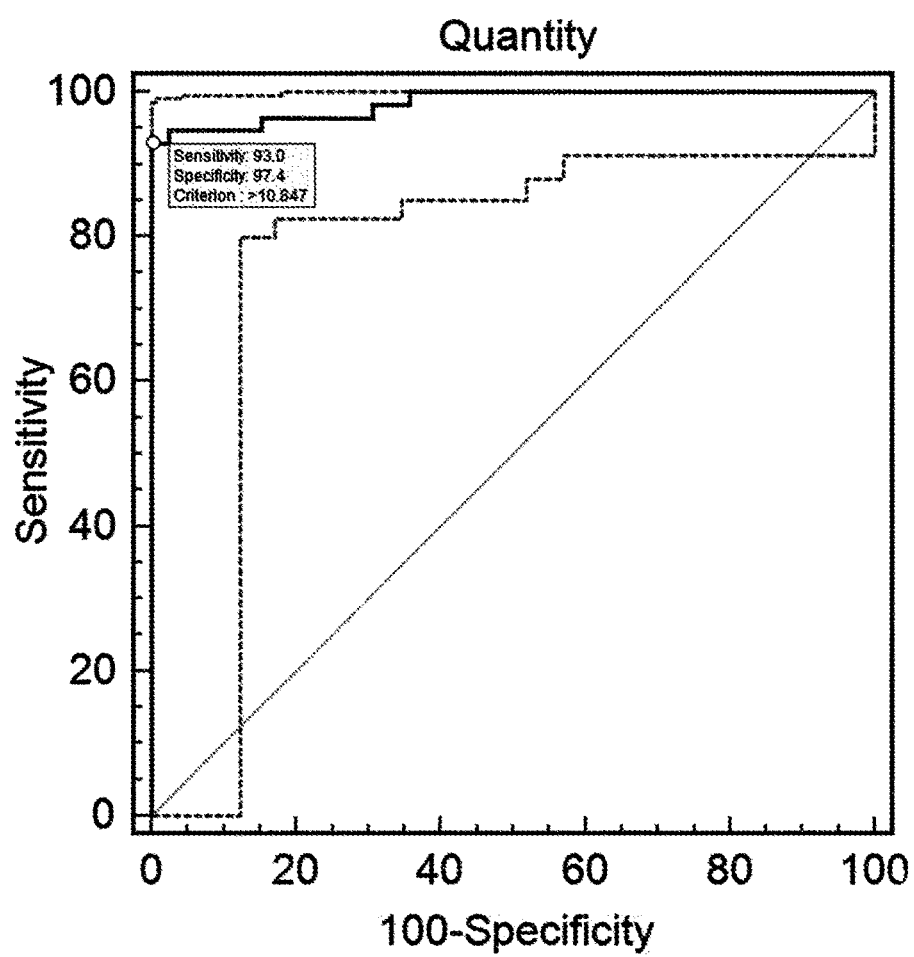
FIG. 10 is a graph showing sensitivity and specificity through ROC analysis of ELISA results using the antibodies B266-1 and B264.

As a result of the comparison of amino acid sequences between hTrx1 and *Chrysochloris asiatica* Trx1, which is structurally similar but has low amino acid sequence similarity to hTrx1, it was confirmed that they have a homology of 82% (FIG. 10).

Figure 12:
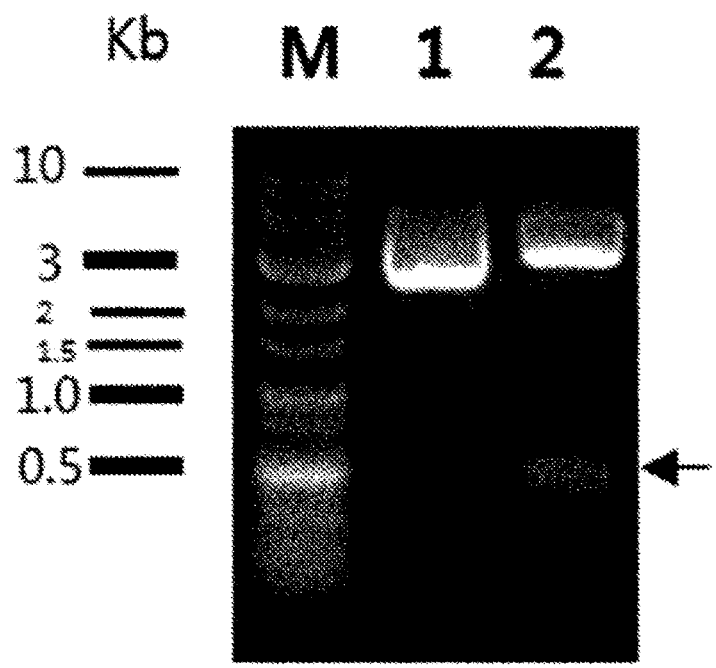
FIG. 12 shows the result of electrophoresis to confirm whether cloning succeeded through a CaTrx1-cloning plasmid and treatment with restriction enzymes (Sfi I and Xho I), where Lane 1 indicates a CaTrx1-cloning plasmid, and Lane 2 indicates a restriction enzyme-treated plasmid.

A gene was synthesized using a known base sequence of CaTrx1 (NCBI Accession Number XM_006863001.1), and to store the gene in *E. coli*, the gene was cloned into a pUCIDT-AMT plasmid. The gene-cloning plasmid was treated with restriction enzymes Sfi I and Xho I, followed by electrophoresis. As a result, as shown in FIG. 12, in the restriction enzyme-treated plasmid (lane 2), a 357-bp DNA fragment cleaved from the plasmid was identified, indicating that the CaTrx1 gene was synthesized (arrow of FIG. 12).

13-2. Expression of CaTrx1 Protein

Figure 13:
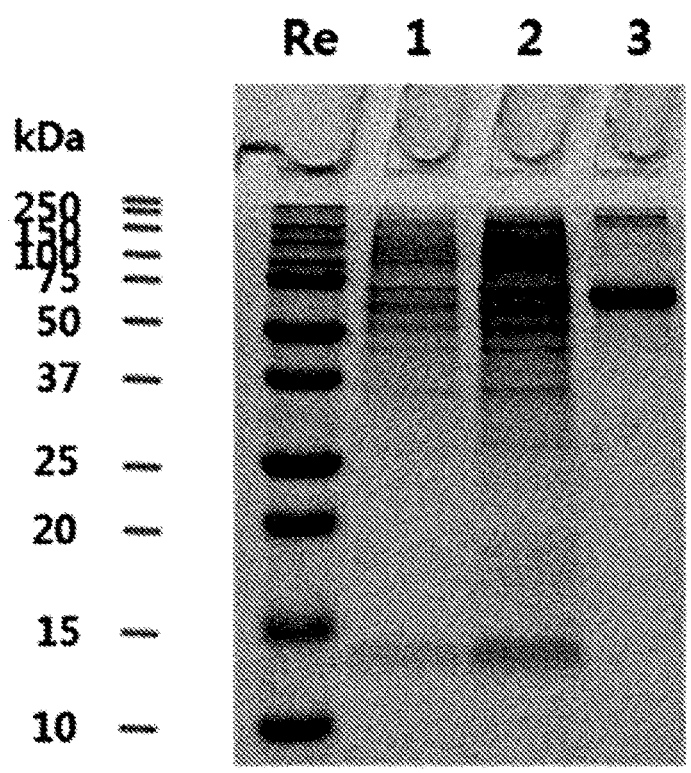
FIG. 13 shows the result of analyzing the extent of the expression of CaTrx1 protein secreted from a cell line by transfecting an animal cell with a CaTrx1 plasmid.

Following the transfection of an animal cell with the CaTrx1 plasmid prepared in Example 13-1, CaTrx1 secreted from the cell line was purified, and the protein was confirmed by 15% SDS-PAGE, and the result is shown in FIG. 13. In FIG. 13, in lanes 1 and 2, amounts of a total protein in a CaTrx1 transformant cell culture solution were 5 μg and 10 μg, respectively, in lane 3, an amount of a control protein (BSA; bovine serum albumin) was 3 μg, confirming that the productivity of the purified CaTrx1 protein was 28.75 mg/L.

Example 14

Confirmation of Affinity of Two Types of Antibodies for hTrx1 and CaTrx1

In this example, the CaTrx1 binding affinity of two types of antibodies B266-1 (Trx1-hIgG1) and B264 (Trx1-mIgG1) was examined.

To confirm the binding affinity of B266-1 (Trx1-hIgG1) and B264 (Trx1-mIgG1) for hTrx1 and CaTrx1, a 96-well ELISA plate was coated with each of 200 ng of hTrx1 and 10 μg of CaTrx1, 200 μL of a blocking buffer (4% Skim milk/1×PBS) was dispensed into each well, followed by a reaction for 1 hour at 37° C. After the removal of a reaction solution, 100 uL each of B266-1 (Trx1-hIgG1) and B264 (Trx1-mIgG1) was dispensed into each well coated with each antigen, and allowed to react at 37° C. for 2 hours. A reaction solution was removed, followed by washing five times with 200 μL of 1×PBST. 100 μL each of anti-human Fc-HRP and mouse-HRP, diluted 1:4,000, was dispensed into each of the B266-1 (Trx1-hIgG1)-treated wells and each of the B264 (Trx1-mIgG1)-treated wells, respectively, followed by a reaction at 37° C. for 2 hours. A reaction solution was removed, and washed five times with 200 μL of 1×PBST. 100 μL of a color reagent was dispensed into each well, and after a 10-minute reaction, 50 μL of 2.5M $H_2SO_4$ was dispensed into each well. After color development, the extent of the color development was assessed using an ELISA reader.

As a result of confirmation of the hTrx1 binding affinity of B266-1 (Trx1-hIgG1) and B264 (Trx1-mIgG1), as shown in Table 14 below, for 200 ng of the antigen, it was confirmed that KD=$2.1 \times 10^{-10}$ M for B266-1, and the affinity of was detected at KD=$1.7 \times 10^{-10}$ M for B264. In addition, referring to FIG. 14A, it was seen that, compared to B266-1, the reaction value (OD 490) by B264 binding is as low as approximately 50%.

Figure 14:
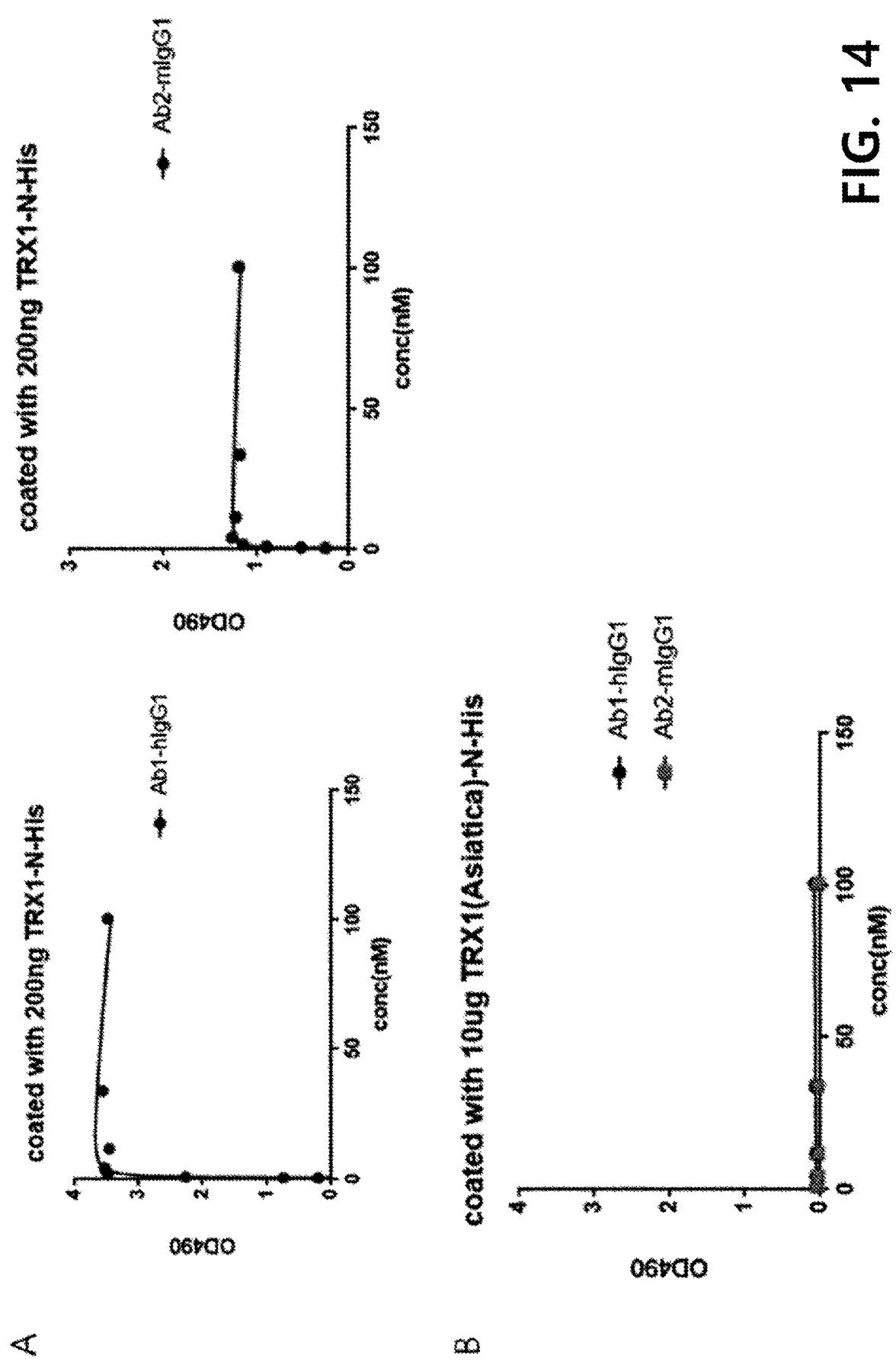
FIG. 14 shows results of analyzing the affinity of the antibodies B266-1 and B264 for hTrx1 and CaTrx1.

As a result of confirmation of the binding affinity of antibodies B266-1 and B264 for g of CaTrx1, as shown in FIG. 14B and Table 14, it was seen that none of the two types of antibodies bind to CaTrx1.

TABLE 14

|  | hTRX1 | | CaTRX1 | |
|---|---|---|---|---|
|  | $K_D$(M) | $R^2$ | $K_D$(M) | $R^2$ |
| B266-1 | $2.1 \times 10^{-10}$ | 0.99 | Not binding | Not binding |
| B264 | $1.7 \times 10^{-10}$ | 0.99 | Not binding | Not binding |

Example 15

Manufacture of Mutant Antigen for hTrx1

15-1. Positioning of Mutations Through Amino Acid Sequencing Between hTrx1 and CaTrx1

A known amino acid sequence of hTrx1 (NCBI Accession Number NP_003320.2) was compared with that of CaTrx1 (NCBI Accession Number XP_006863063.1). As shown in FIG. 15A, although the amino acid sequence homology between hTrx1 and CaTrx1 was 82%, the binding affinity of the antibodies for an antigen was significantly different, and thus there were 8 different parts in which hTrx1 and CaTrx1 have different amino acid sequences (FIG. 15B).

15-2. Fusion PCR and Cloning for Expressing Mutant Proteins

A) Fragment PCR

Figure 15D:
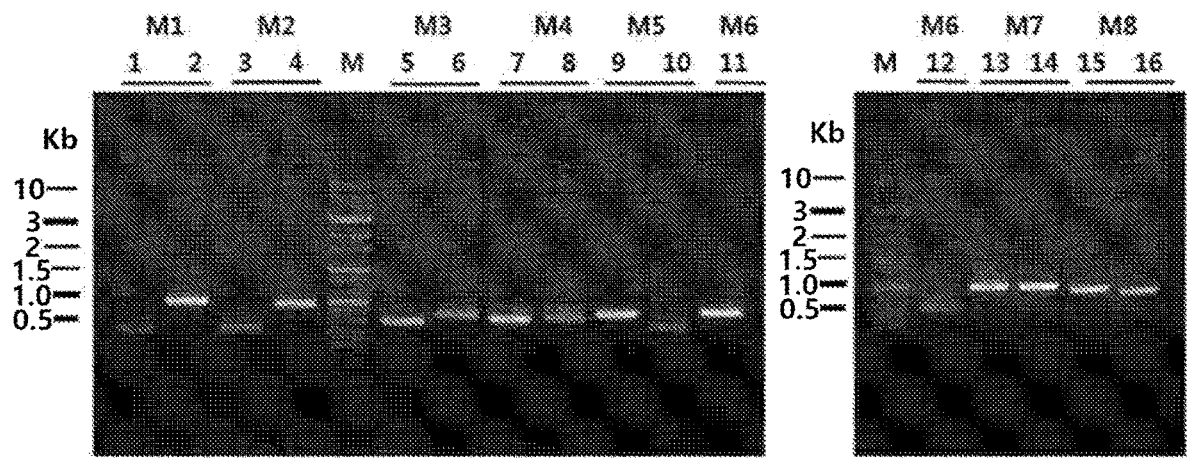
FIG. 15D shows the result of the amplification of DNA fragments for positioning of mutations.

In the 8 parts in which hTrx1 and CaTrx1 have different amino acid sequences, identified in Example 15-1, a hTrx1 sequence was substituted with a CaTrx1 sequence, and then a DNA fragment of a cassette for manufacturing a mutant was amplified (FIG. 15D).

Specifically, to manufacture a gene for expressing each mutant protein, two DNA fragments for fusion PCR have to be amplified. Therefore, two types of primers (F2 and R1; FIG. 15C and Table 15) containing a part requiring mutation of a base sequence were manufactured, and DNA fragments were amplified using two pairs of primers F1 and R1 and F2 and R2. To amplify the DNA fragments, template DNA (100-200 ng) and 1 μL each of forward and reverse primers (10 pmol each) were added to 25 μL of 2×EF-Taq PCR Smart mix (0.5× Band Doctor) (Solgent, SEF02-M50h), and the final volume was adjusted with sterile purified water, followed by stirring well and amplification using a PCR device (Thermal cycler, T100).

B) Fusion PCR for Fusing Two Types of DNA Fragments and Purification of PCR Product To fuse the amplified DNA fragments, PCR was carried out using two DNA fragments and primers F1 and R2 (FIG.

TABLE 15

| Purpose | Primer name | Sequence (5'->3') | Role of primer in FIG. 15C | SEQ ID NO: |
|---|---|---|---|---|
| Fragment amplification | Vector-F | GGCGTGTACGGTGGGAGGT | F1 | SEQ ID NO: 46 |
| | Vector-R | AGCAGCGTATCCACATAGCG | R2 | SEQ ID NO: 47 |
| TRX1-M1 mutation | TRX M1-F | CATCACGTCAAAGAGATCGAAGGCAAAGAAGATTTTCAAGAAGCCCTGGACGCCGCT | F2 | SEQ ID NO: 48 |
| | TRX M1-R | GGCTTCTTGAAAATCTTCTTTGCCTTCGATCTCTTTGACGTGATGATGATGATGATGAT | R1 | SEQ ID NO: 49 |
| TRX1-M2 mutation | TRX M2-F | AAAACCGCATTTCATGCTGCCCTGAGCAGTGCTGGTGACAAACTGGTCGTGG | F2 | SEQ ID NO: 50 |
| | TRX M2-R | TTTGTCACCAGCACTGCTCAGGGCAGCATGAAATGCGGTTTTTGATTCGATCTG | R1 | SEQ ID NO: 51 |
| TRX1-M3 mutation | TRX-M3-OV-F | ATTAAACCGTTTTATCATAGCCTGTCTGAAAATACAGTAACGTTATCTTTCTGGAAG | F2 | SEQ ID NO: 52 |
| | TRX-M3-OV-R | AGACAGGCTATGATAAAACGGTTTAATCATTTTACACGGGCCGCACCAGG | R1 | SEQ ID NO: 53 |
| TRX1-M4 mutation | TRX-M4-OV-F | CTGTCTGAAAAATTTGGCAACATGGTGTTCCTGGAAGTGGATGTTGATGACTGCCAGGACGTCGC | F2 | SEQ ID NO: 54 |
| | TRX-M4-OV-R | ATCCACTTCCAGGAACACCATGTTGCCAAATTTTTCAGACAGGCTATGGAAAAACGGTTTAATCATTTTACAC | R1 | SEQ ID NO: 55 |
| TRX1-M5 mutation | TRX-M5-OV-F | GTGAAATGTATGATAACGTTCCAGTTTTTCAAAAAAGGTCAAAAAGTCGGTGAAT | F2 | SEQ ID NO: 56 |
| | TRX-M5-OV-R | AAACTGGAACGTTATCATACATTTCACTTCGCATTCGCTCGCACGTCC | R1 | SEQ ID NO: 57 |
| TRX1-M6 mutation | TRX-M6-OV-F | ACGTTCCAGTTTTATAAAAAAAGGGAAAAAGTCGGTGAATTTAGCGGTGCCAACAAAGAAAAACT | F2 | SEQ ID NO: 58 |
| | TRX-M6-OV-R | TTCACCGACTTTTTCCCTTTTTTATAAAACTGGAACGTCGGCATACATTTCACTTCGCATTCG | R1 | SEQ ID NO: 59 |
| TRX1-M7 mutation | TRX-M7-Xho-R | GAATTCTCGAGCTATCACACCAGTTCGTTAATCGTGGCTTCCAGTTTTTCTTTGTTAACACCGCTAAATTCACCGACTTTTTGA | F2 | SEQ ID NO: 60 |
| TRX1-M8 mutation | TRX-M8-Xho-R | GAATTCTCGAGCTATCAACACAGTTCGTTAATGATGGCTTCCAGTTTTTCTTTGTTGGC | R1 | SEQ ID NO: 61 |
| Colony PCR | N293F-colo-F | GGCGTGTACGGTGGGAGGT | — | SEQ ID NO: 62 |
| | N293F-colo-R | AGCAGCGTATCCACATAGCG | — | SEQ ID NO: 63 |

PCR was carried out under conditions of 1 cycle of pre-denaturation at 95° C. for 2 min, 30 cycles of 3-step amplification at 95° C. for 20 sec; at 62° C. for 40 sec; and at 72° C. for 1 min, and 1 cycle of post-extension at 72° C. for 5 min, and then the reaction was terminated. The amplified DNA fragment was confirmed using a 1% agarose gel (FIG. 15D). Purification of a gene was carried out using a QIAquick Gel Extraction Kit (QIAGEN, 28704) according to the manufacturer's protocol.

Figure 15E:
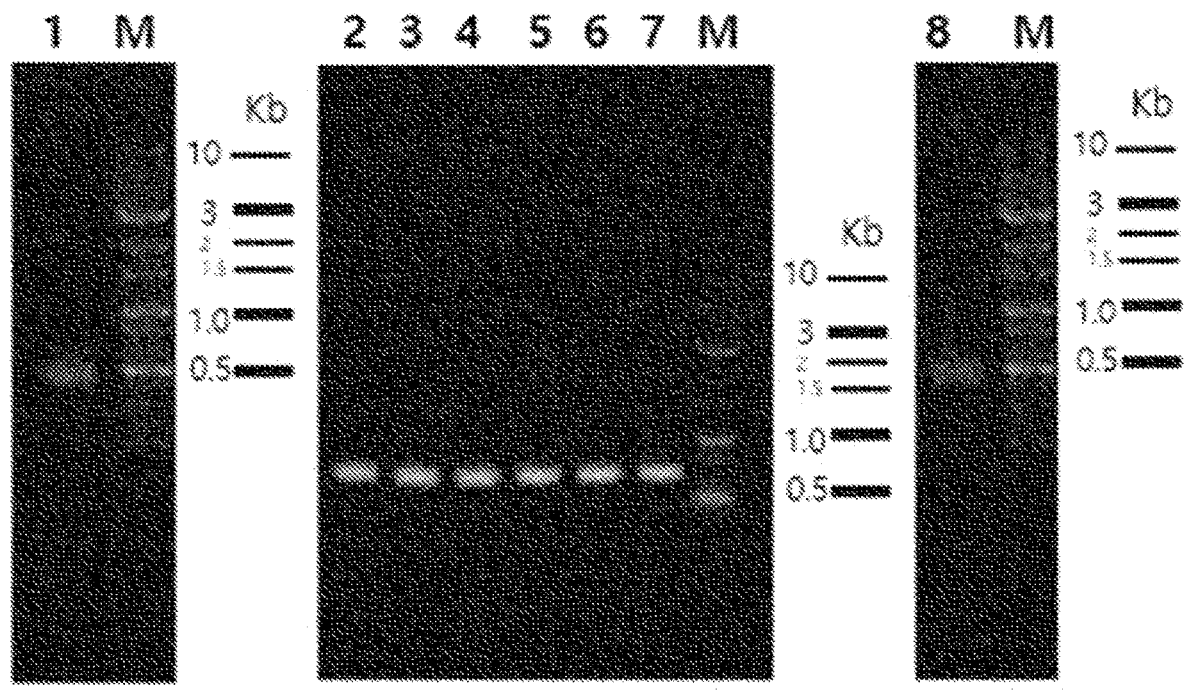
FIG. 15E shows the result of manufacturing cassettes through overlapping PCR using the manufactured DNA fragments.

15C). A PCR mixture for fusion PCR was prepared by adding 100 to 150 ng each of the two types of DNA fragments and 1 μL each of forward and reverse primers (10 pmol each) to 25 μL 2×EF-Taq PCR Smart mix (0.5× Band Doctor) (Solgent, SEF02-M50h), and the final volume was adjusted with sterile purified water, followed by stirring well and amplification with a PCR device. PCR was carried out under conditions of 1 cycle of pre-denaturation at 95° C. for 2 min, 30 cycles of 3-step amplification at 95° C. for 20 sec;

at 62° C. for 40 sec; and at 72° C. for 1 min, and 1 cycle of post-extension at 72° C. for 5 min, and then the reaction was terminated. After the termination of the reaction, a PCR product was confirmed using a 1% agarose gel (FIG. 15E).

After the termination of the fusion PCR, the produced PCR product was purified using ethanol precipitation. 3 M sodium acetate (pH 5.2) and 100% ethanol were respectively added to the amplified PCR product at 1/10-fold and 2-fold of the total volume of the PCR product, and well stirred, reacted in a −70° C. ultra-low temperature freezer for 10 minutes. Afterward, the resulting mixture was centrifuged at 13,000 rpm for 10 minutes, a supernatant was removed, 1 mL of 70% ethanol was added, and then the resulting mixture was stirred, followed by centrifugation at 13,000 rpm for 10 minutes. A supernatant was removed and residual ethanol was removed by a reaction in a 70° C. heat block for 3 minutes, and a DNA pellet was dissolved well in 50 µL of distilled water.

C) Cloning of PCR Product

To clone the purified PCR product into a N293F plasmid, a restriction enzyme was treated. Specifically, 50 µL of the PCR product and the N293F plasmid was treated with each of 7 µL of Kpn I and 8 µL of a 10× buffer, and a total volume was adjusted to 80 µL. After stirring well, the resulting mixture was reacted in a 37° C. water bath for 3 hours. After the termination of the reaction, the resulting mixture was purified by ethanol precipitation. Afterward, the purified mixture was treated with 7 µL of Xho I and 8 µL of a 10× buffer, and the total volume was adjusted to 80 µL. After stirring well, the resulting product was reacted in a 37° C. water bath for 3 hours. To purify the reaction-terminated DNA, an experiment was carried out using a QIAquick Gel Extraction Kit (QIAGEN, 28704) according to the manufacturer's protocol.

To clone the purified DNA fragment into N293F, 20 ng of N293F which was treated with a DNA fragment (100 ng; 1 Kb or less, 300 ng; 3 kb or less) and the restriction enzymes, was treated with 1 µL of a T4 DNA ligase (Thermo Scientific, EL0011) and 1 µL of a 10× buffer were added, and the total volume was adjusted to 10 µL with distilled water. The resulting mixture was reacted for 16 hours at 22° C. After termination of the reaction, DH5 competent cells were extracted to be transformed into E. coli, and dissolved on ice. 2 µL of a ligation product was well mixed with DH5α competent cells, and then reacted on ice for 30 minutes. Subsequently, the reaction product was reacted in a 42° C. water bath for 90 seconds, and further reacted on ice for 3 minutes. 500 µL of an SOC medium (20 g of Bacto Tryptone, 5 g of Bacto Yeast Extract, and 0.5 g of NaCl per liter) were added to the reaction product, and incubated in a 37° C. shaking incubator for 30 minutes. After incubation, 100 µL of the reaction product was sprayed and spread on a 100 µg/mL ampicillin-added LB medium (10 g of Bacto Tryptone, 5 g of Bacto Yeast Extract, and 10 g of NaCl per liter), and incubated in a 37° C. incubator for 12 to 16 hours.

D) Colony PCR and Sequencing to Confirm Transformation

To confirm the presence or absence of a cloning plasmid, colony PCR was performed. A PCR mixture for fusion PCR was prepared by adding 0.5 mL each of forward and reverse primers (10 pmol each) to 12.5 µL 2×EF-Taq PCR Smart mix (0.5× Band Doctor) (Solgent, SEF02-M50h), and the final volume was adjusted with sterile distilled water, followed by stirring well and amplification by PCR. PCR was performed under conditions of 1 cycle of pre-denaturation at 95° C. for 2 min, 25 cycles of 3-step amplification at 95° C. for 20 sec; at 62° C. for 40 sec; and at 72° C. for 1 min, and 1 cycle of post-extension at 72° C. for 5 min, and then the reaction was terminated.

Figure 15F:
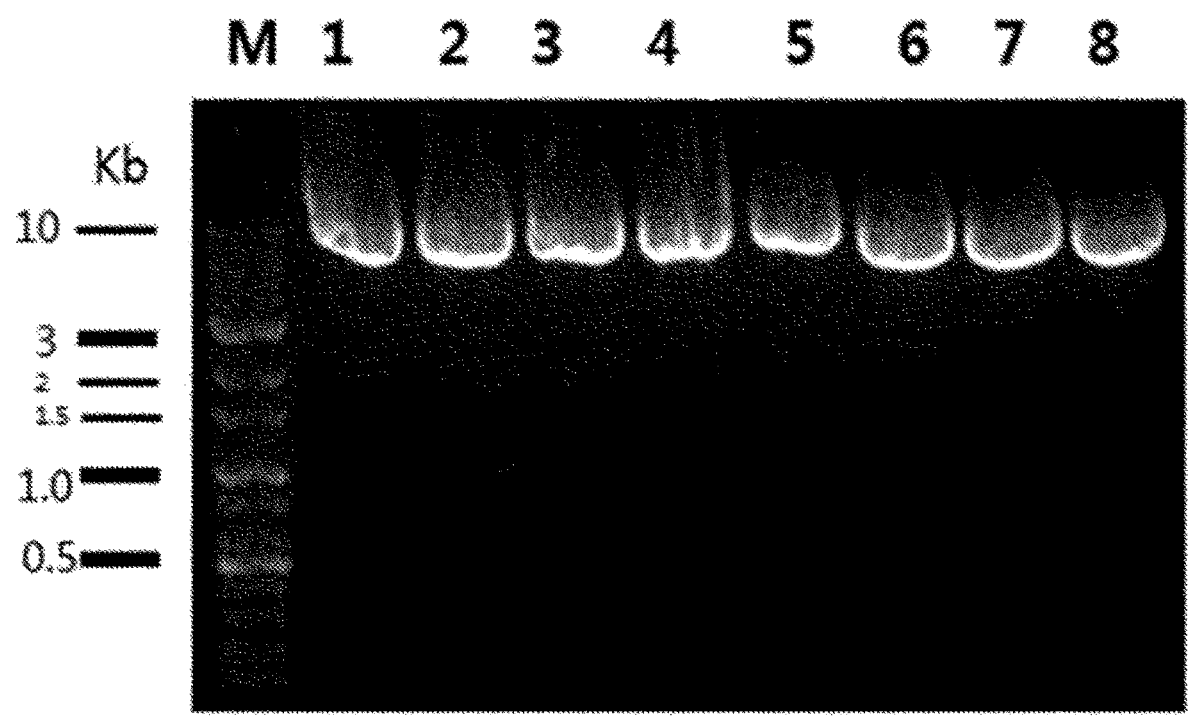
FIG. 15F shows the expression of 8 types of hTrx1 mutant genes by transforming 293F with plasmids cloning each hTrx1 mutant gene.

After the termination of the reaction, the amplified product was confirmed using a 1% agarose gel (FIG. 15F). The amplified product was purified, and Neoprobe Corp was commissioned to carry out sequencing. Sequencing data is shown in Table 16 below. Sequences underlined in bold type indicate sequences that have been mutated.

TABLE 16

| Name | Base sequence data | SEQ ID NO: |
|---|---|---|
| TRX-N-His-M1 | GTCAAAGAGATCGAAGGCAAAGAAGATTTTCAAGAAGCCCTGGACGCCGCTGGTGACAAACTGGTCGTGGTGGACTTTAGTGCTACCTGGTGCGGCCCGTGTAAAATGATTAAACCGTTTTTCCATAGCCTGTCTGAAAAATACAGTAACGTTATCTTTCTGGAAGTGGATGTTGATGACTGCCAGGACGTCGCGAGCGAATGCGAAGTGAAATGTATGCCGACGTTCCAGTTTTTCAAAAAAGGTCAAAAAGTCGGTGAATTTAGCGGTGCCAACAAAGAAAAACTGGAAGCCACGATTAACGAACTGGTG | SEQ ID NO: 38 |
| TRX-N-His-M2 | GTCAAACAGATCGAATCAAAAACCGCATTTCATGCTGCCCTGAGCAGTGCTGGTGACAAACTGGTCGTGGTGGACTTTAGTGCTACCTGGTGCGGCCCGTGTAAAATGATTAAACCGTTTTTCCATAGCCTGTCTGAAAAATACAGTAACGTTATCTTTCTGGAAGTGGATGTTGATGACTGCCAGGACGTCGCGAGCGAATGCGAAGTGAAATGTATGCCGACGTTCCAGTTTTTCAAAAAAGGTCAAAAAGTCGGTGAATTTAGCGGTGCCAACAAAGAAAAACTGGAAGCCACGATTAACGAACTGGTG | SEQ ID NO: 39 |
| TRX-N-His-M3 | GTCAAACAGATCGAATCAAAAACCGCATTTCAAGAAGCCCTGGACGCCGCTGGTGACAAACTGGTCGTGGTGGACTTTAGTGCTACCTGGTGCGGCCCGTGTAAAATGATTAAACCGTTTTATCATAGCCTGTCTGAAAAATACAGTAACGTTATCTTTCTGGAAGTGGATGTTGATGACTGCCAG | SEQ ID NO: 40 |

TABLE 16-continued

| Name | Base sequence data | SEQ ID NO: |
|---|---|---|
| | GACGTCGCGAGCGAATGCGAAGTGAAATGT ATGCCGACGTTCCAGTTTTTCAAAAAAGGTC AAAAAGTCGGTGAATTTAGCGGTGCCAACAA AGAAAAACTGGAAGCCACGATTAACGAACT GGTG | |
| TRX-N-His-M4 | GTCAAACAGATCGAATCAAAAACCGCATTTC AAGAAGCCCTGGACGCCGCTGGTGACAAACT GGTCGTGGTGGACTTTAGTGCTACCTGGTGC GGCCCGTGTAAAATGATTAAACCGTTTTTCC ATAGCCTGTCTGAAAAATTTGGCAACATGG TGTTCCTGGAAGTGGATGTTGATGACTGCCA GGACGTCGCGAGCGAATGCGAAGTGAAATG TATGCCGACGTTCCAGTTTTTCAAAAAGGT CAAAAAGTCGGTGAATTTAGCGGTGCCAACA AAGAAAAACTGGAAGCCACGATTAACGAAC TGGTG | SEQ ID NO: 41 |
| TRX-N-His-M5 | GTCAAACAGATCGAATCAAAAACCGCATTTC AAGAAGCCCTGGACGCCGCTGGTGACAAACT GGTCGTGGTGGACTTTAGTGCTACCTGGTGC GGCCCGTGTAAAATGATTAAACCGTTTTTCC ATAGCCTGTCTGAAAAATACAGTAACGTTAT CTTTCTGGAAGTGGATGTTGATGACTGCCAG GACGTCGCGAGCGAATGCGAAGTGAAATGT ATGATAACGTTCCAGTTTTTCAAAAAGGTC AAAAAGTCGGTGAATTTAGCGGTGCCAACAA AGAAAAACTGGAAGCCACGATTAACGAACT GGTG | SEQ ID NO: 42 |
| TRX-N-His-M6 | GTCAAACAGATCGAATCAAAAACCGCATTTC AAGAAGCCCTGGACGCCGCTGGTGACAAACT GGTCGTGGTGGACTTTAGTGCTACCTGGTGC GGCCCGTGTAAAATGATTAAACCGTTTTTCC ATAGCCTGTCTGAAAAATACAGTAACGTTAT CTTTCTGGAAGTGGATGTTGATGACTGCCAG GACGTCGCGAGCGAATGCGAAGTGAAATGT ATGCCGACGTTCCAGTTTTATAAAAAAAGGG AAAAAGTCGGTGAATTTAGCGGTGCCAACAA AGAAAAACTGGAAGCCACGATTAACGAACT GGTG | SEQ ID NO: 43 |
| TRX-N-His-M7 | GTCAAACAGATCGAATCAAAAACCGCATTTC AAGAAGCCCTGGACGCCGCTGGTGACAAACT GGTCGTGGTGGACTTTAGTGCTACCTGGTGC GGCCCGTGTAAAATGATTAAACCGTTTTTCC ATAGCCTGTCTGAAAAATACAGTAACGTTAT CTTTCTGGAAGTGGATGTTGATGACTGCCAG GACGTCGCGAGCGAATGCGAAGTGAAATGT ATGCCGACGTTCCAGTTTTTCAAAAAGGTC AAAAAGTCGGTGAATTTAGCGGTGTTAACAA AGAAAAACTGGAAGCCACGATTAACGAACT GGTG | SEQ ID NO: 44 |
| TRX-N-His-M8 | GTCAAACAGATCGAATCAAAAACCGCATTTC AAGAAGCCCTGGACGCCGCTGGTGACAAACT GGTCGTGGTGGACTTTAGTGCTACCTGGTGC GGCCCGTGTAAAATGATTAAACCGTTTTTCC ATAGCCTGTCTGAAAAATACAGTAACGTTAT CTTTCTGGAAGTGGATGTTGATGACTGCCAG GACGTCGCGAGCGAATGCGAAGTGAAATGT ATGCCGACGTTCCAGTTTTTCAAAAAGGTC AAAAAGTCGGTGAATTTAGCGGTGCCAACAA AGAAAAACTGGAAGCCATCATTAACGAACT GTGT | SEQ ID NO: 45 |

E) Plasmid Preparation (Midi-Preparation)

Colonies containing plasmids that have been sequenced were inoculated into 100 mL of a 2×YT medium (17 g of tryptone, 10 g of a yeast extract, and 5 g of NaCl per liter) containing 100 µg/mL of ampicillin, and incubated at 37° C. and 210 rpm for 16 hours. The incubated bacteria were obtained by centrifugation at 4,500 rpm for 8 minutes. To obtain a purified plasmid, NucleoBond® Xtra Midi (Macherey-Nagel, Cat. 740410.100) was used, and an experiment was carried out according to the manufacturer's protocol.

F) Animal Cell Culture 19.4 g of Freestyle™ 293 expression medium AGT™ powder (AG100009, Thermo Scientific) was dissolved in 1 L of deionized water and sterilized. 35 mL of the Freestyle™ 293 expression medium AGT™ media, which was heated in a 37° C. water bath for 30 minutes, was put into a 125 mL Erlenmeyer flask (CC-431143, Corning). After thawing a frozen cell line 293F (510029, Invitrogen) in a 37° C. water bath for approximately 1 to 2 minutes, the thawed cell line was mixed with 5 mL of Freestyle™ 293 expression medium AGT™ media, and dispensed into a 125 mL Erlenmeyer flask containing 35 mL of the medium, followed by incubation in an 8% $CO_2$ shaking incubator at 37° C. and 85 rpm. After 2 to 3 days of incubation, 10 μL of the cell line was mixed with 10 μL of trypan blue, and 10 μL of the resulting mixture was added to a Luna cell counting chip (L12002, Biosystems), and cell viability and a cell count were confirmed using a Luna™ automated cell counter (L10001, Biosystems). After 4 to $7 \times 10^5$ cells/mL of the cells were suspended in a 40 mL medium, the resulting suspension was centrifuged at 100×g for 5 minutes to remove a supernatant. After removal of the supernatant, the cell pellet was mixed with 10 mL of a medium to resuspend the pellet, and then 30 mL of the medium was inoculated into a 125 mL Erlenmeyer flask. The cells were incubated in an 8% $CO_2$ shaking incubator at 37° C. and 85 rpm, and the above-described process was performed two or more times.

G) Transfection into Animal Cells

A 40 mL aliquot of $5.5 \times 10^5$ cells/mL of cells were put into a tube, and centrifuged at 100×g for 5 minutes. After removal of a culture solution, a pellet was suspended using 10 mL of Freestyle™ 293 expression medium AGT™ media, and inoculated into a 125 mL Erlenmeyer flask. The cells were incubated in an 8% $CO_2$ shaking incubator at 37° C. and 85 rpm. The cell count and viability were confirmed to be $1 \times 10^6$ cells/mL and 90% or more, respectively, using a Luna™ automated cell counter. Based on 40 mL of the culture solution, each of 25 μg DNA for transfection and 100 μg PEI (23966, Polysciences) was stirred by vortexing, followed by centrifugation at 10,000 rpm for 1 second. DNA and PEI mixed in 800 μL of Freestyle™ 293 expression medium AGT™ were stirred, and allowed to react at room temperature for 20 minutes. The reacted DNA-PEI mixture was reacted in the 125 mL flask in which the cell line was incubated. After 24 hours, supplements were added to 5 g/L. Subsequently, the cells were further incubated for 5 days, and the culture solution was collected.

H) Experiment for Confirming Expression in Culture Medium

Figure 16:
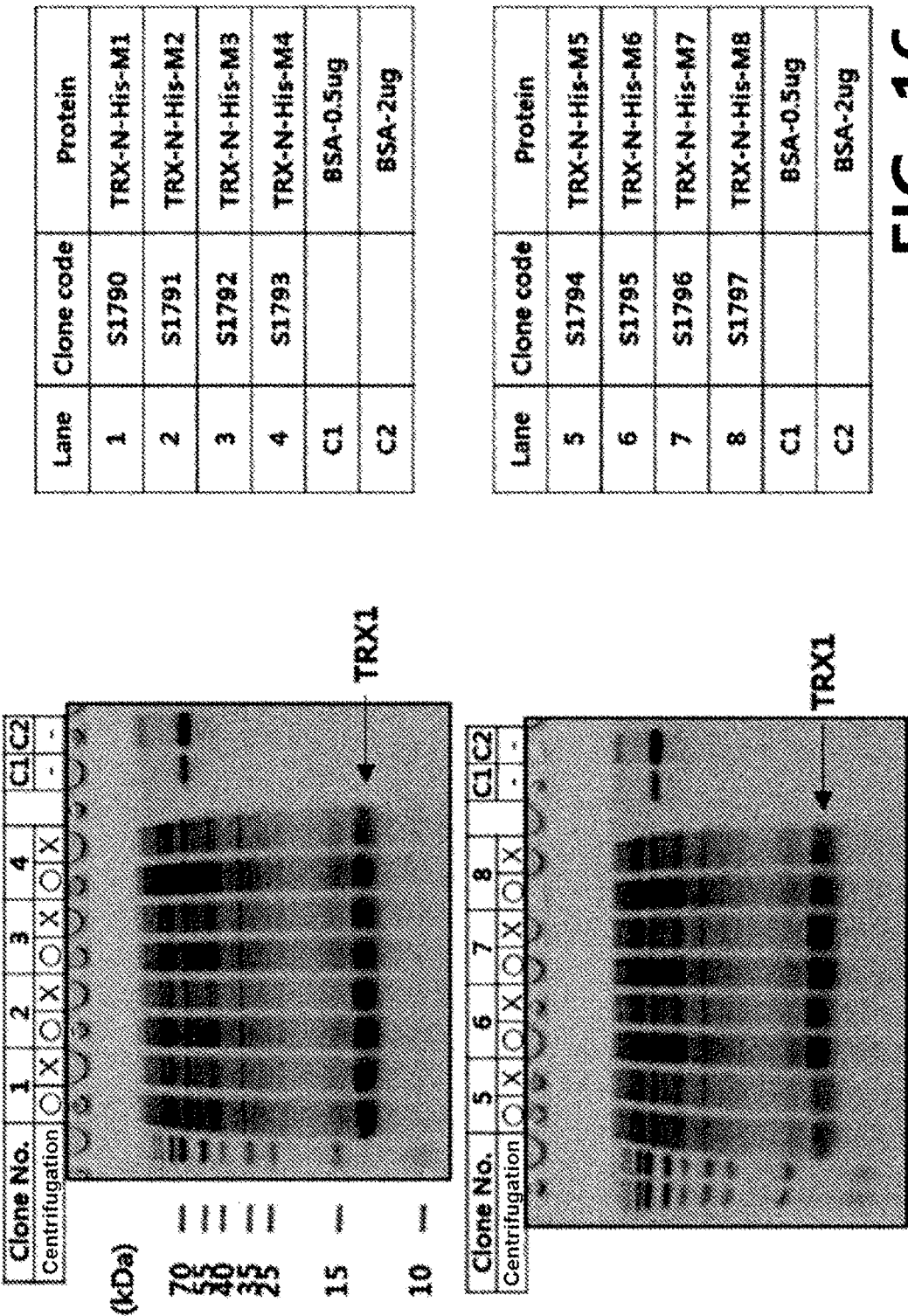
FIG. 16 shows proteins secreted in a culture solution after the genes obtained through transformation in FIG. 15 are transduced into HEK293 human cells and cultured, which are detected by SDS-PAGE. Since the size of Trx1 is approximately 12 kDa, a protein with the corresponding size is detected, confirming that the 8 types of transformed genes are expressed and secreted as proteins in a culture solution.

After 5-day culture, 500 μL of the collected culture solution was dispensed into tubes. One of the tubes was placed in a centrifuge tube rack for 20 minutes, a supernatant (sample that had not been centrifuged) was used, and the other tubes were centrifuged at 10,000 rpm for 2 minutes to remove the cells, and only a supernatant (sample that had been centrifuged) was used. 10 μL of a 5× reduction sample buffer was mixed with 40 μL of the supernatant, followed by boiling at 100° C. for 5 minutes. The prepared sample was confirmed by 15% SDS-PAGE using Mini-PROTEAN® Tetra Cell (BR165-8029, Bio-Rad) (FIG. 16).

I) Purification Using Affinity Chromatography (Ni-NTA)

Figure 17:
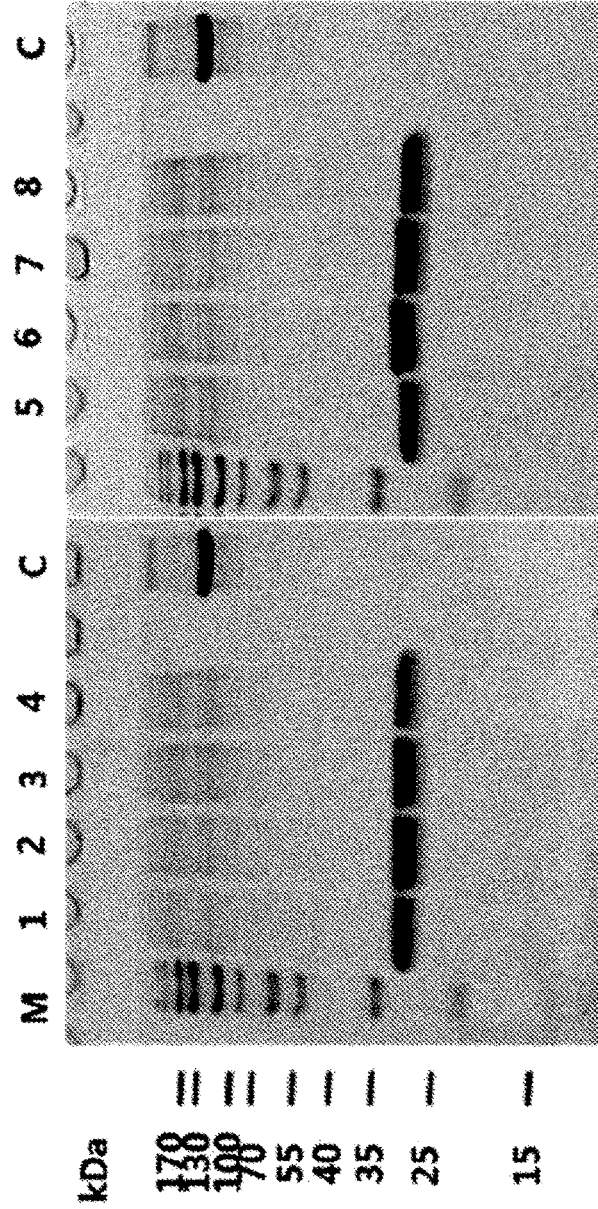
FIG. 17 shows a result of analyzing the extent of expression of 8 types of hTrx1 mutant proteins detected in FIG. 16 after purification.

A transformed cell line was incubated for 6 days, and centrifuged at 4,800 rpm for 30 minutes to remove a supernatant. A PolyPrep column (731-1553, Bio-Rad) was washed using a 10 mM imidazole washing buffer (pH 7.4), and packed with Ni-Sepharose™ 6 Fast Flow beads (17-5318-02, GE Healthcare). Afterward, the column was washed with a 10 mM imidazole washing buffer (pH 7.4) twice. When approximately 2 to 3 mL of a 10 mM imidazole washing buffer (pH 7.4) remained in the column, the column was washed again with 20 mL of a 10 mM imidazole washing buffer (pH 7.4). A medium was added to the washed column. The beads were washed with a 10 mM imidazole washing buffer (pH 7.4), and elusion was performed with a 500 mM imidazole elution buffer (pH 7.4). 10 μL of the sample was mixed with 200 μL of a Coomassie Plus™ protein detection reagent (1856210, Thermo Scientific) and eluted until the sample did not turn blue. A purification solution for the eluted protein was concentrated using an Amicon® ultracentrifuge (UFC901096, Millipore), and the buffer was exchanged by repeating reconcentration with a PBS solution at least twice. A protein concentration was measured using a Nano-drop, and diluted to be 0.3 to 0.5 mg/mL. 3 μg of each protein was confirmed by SDS-PAGE (FIG. 17).

In addition, the concentrations and productivity of the 8 types of hTrx1 mutant proteins were assessed, and the results are shown in Table 17 below. Referring to Table 17, it can be seen that the 8 types of the hTrx1 mutant proteins are expressed at concentrations ranging from 3.15 to 5.31 mg/mL.

TABLE 17

| ID | hTrx1 mutant protein | Concentration (mg/mL) | Protein (mg) | Productivity (mg/L) |
| --- | --- | --- | --- | --- |
| S1790 | TRX-N-His-M1 | 4.76 | 4.71 | 117.75 |
| S1791 | TRX-N-His-M2 | 4.12 | 4.28 | 107.0 |
| S1792 | TRX-N-His-M3 | 3.81 | 3.73 | 93.25 |
| S1793 | TRX-N-His-M4 | 3.99 | 3.63 | 90.75 |
| S1794 | TRX-N-His-M5 | 3.15 | 3.30 | 82.50 |
| S1795 | TRX-N-His-M6 | 3.98 | 4.33 | 108.25 |
| S1796 | TRX-N-His-M7 | 5.31 | 5.15 | 128.75 |
| S1797 | TRX-N-His-M8 | 3.07 | 3.07 | 76.75 |

Example 16

ELISA for Confirming Binding Affinity

In this example, the binding affinity of each of the B266-1 and B264 antibodies for the 8 types of hTrx1 mutant proteins prepared in Example 15 was confirmed.

The 8 types of hTrx1 mutant proteins prepared in Example 3 were dissolved in a coating buffer (DPBS; LB001-02, Welgene) at a concentration of 2 μg/mL, thereby preparing antigen solutions, each antigen solution was dispensed into a 96-well plate at 100 μL per well, and the plate was covered with a sealing tape, followed by a reaction at 4° C. for 16 hours. After removal of the antigen solution, 200 μL of a blocking buffer (1×PBS w/4% skim milk) was dispensed into each well, and the plate was covered with a sealing tape, followed by a reaction in a 37° C. incubator for 1 hour. After the completion of the reaction, the blocking buffer was removed, 100 μL of the antibody solution diluted to a certain concentration was dispensed into each well, and the plate was covered with a sealing tape, followed by a reaction in a 37° C. incubator for 2 hours. The antibody solution was removed, a process of treating and discarding 200 μL of a washing buffer (1×PBST) solution per well was repeated a total of 5 times. HRP-binding antibodies (anti-human Fc-HRP against B266, anti-mouse Fc-HRP against B264) were diluted 1:4000 in an antibody dilution solution (1×PBS w/1% Skim milk), 100 μL of the resulting dilution was dispensed into each well, and the plate was covered with a sealing tape, followed by a reaction in a 37° C. incubator for 2 hours. The antibody solution was removed, and a process of treating and discarding 200 μL of a washing buffer (1×PBST) solution was repeated a total of five times. 10 μL of $H_2O_2$ was added to a color reagent [one OPD tablet, 10 mL PC buffer (5.1 g of $C_6H_8O_7 \cdot H_2O$ and 7.3 g of $Na_2HPO_4$ per liter], and then 100 μL of the resulting mixture was dispensed into each well, followed by a reaction in a dark place for 10 minutes. 50 μL per well of a stop buffer (2.5 M H₂SO₄) was treated, and OD at 490 nm was measured.

As a result, as shown in FIGS. 18A to 18C, it was confirmed that the B266-1 (hTrx1-hIgG1) antibody was decreased in binding strength with a protein having a mutation at an M4 site (YSNVIFGNMV), and the B264 (hTrx1-mIgG1) antibody was decreased in binding strength with a protein having mutations at M1, M2 and M4 sites (M1: QIESKTAEIEGKED, M2: QEALDAHAALSS, and M3: YSNVIFGNMV).

Tables 18 and 19 below show original amino acid sequences and base sequences of the M1, M2 and M4 sites having mutations in hTrx1.

TABLE 18

| hTrx1 site | Amino acid sequence | SEQ ID NO: |
|---|---|---|
| M1 | QIEGSTA | SEQ ID NO: 32 |
| M2 | QEALDA | SEQ ID NO: 33 |
| M4 | YSNVI | SEQ ID NO: 34 |

TABLE 19

| hTrx1 site | Base sequence | SEQ ID NO: |
|---|---|---|
| M1 | CAGATCGAATCAAAAACCGCA | SEQ ID NO: 35 |
| M2 | CAAGAAGCCCTGGACGCC | SEQ ID NO: 36 |
| M4 | TACAGTAACGTTATC | SEQ ID NO: 37 |

From the above result, it was confirmed that the B266-1 antibody and the B264 antibody are likely to share the M4 part (YSNVI) of an antigen-binding site.

Example 17

Antibody Profiling Using Peptide Microarrays

Figure 19:
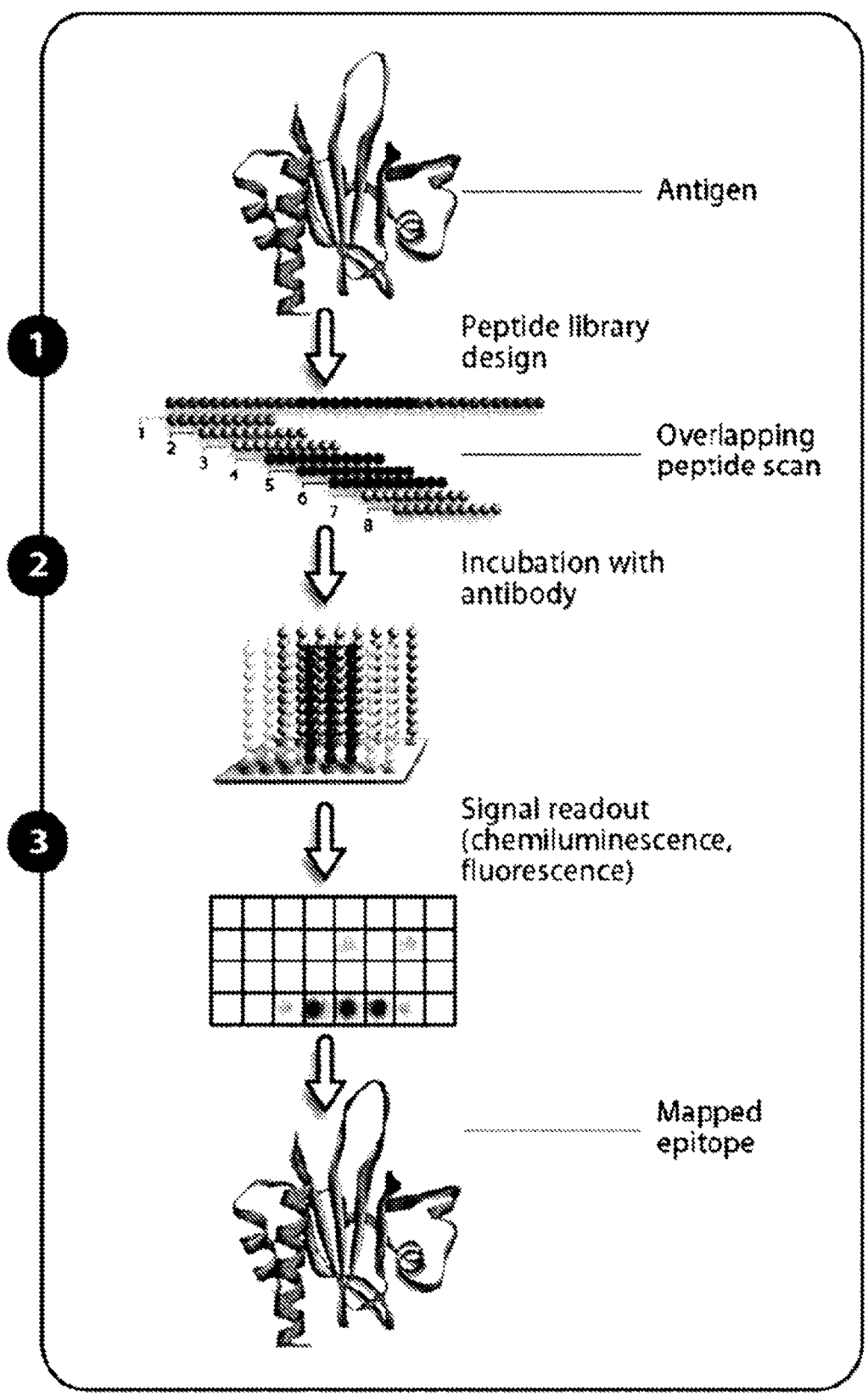
FIG. 19 is a schematic diagram illustrating the general principle of epitope detection using an overlapping peptide scan used in Example 17.

In this example, an accurate amino acid sequence was identified through Trx1 antigen epitope mapping analysis using antibodies B266-1 and B264. Specifically, PepStar™ peptide microarray technology (JPT Peptide Technologies (Germany)) was used, and as shown in FIG. 19, an epitope was detected using an overlapping peptide scan.

17-1. Sequences

Antibody profiling experiments were performed on a peptide library consisting of 108 peptides. The complete list of the peptides is shown in Tables 20 to 22 below. Here, SEQ ID NOs: 64 to 81 corresponding to Peptide_001 to Peptide_018 are not native forms, and include recombinant insert regions. For a known amino acid sequence of the hTrx1 protein, GenBank Accession No. AAF87085.1 was referenced.

TABLE 20

| Peptides immobilized on microarrays | | |
|---|---|---|
| SEQ ID NO: | Amino acid sequence | Name |
| 64 | VATAADVHSQHHHHH | Peptide_001 |
| 65 | ATAADVHSQHHHHHH | Peptide_002 |

TABLE 20-continued

| Peptides immobilized on microarrays | | |
|---|---|---|
| SEQ ID NO: | Amino acid sequence | Name |
| 66 | TAADVHSQHHHHHHH | Peptide_003 |
| 67 | AADVHSQHHHHHHHH | Peptide_004 |
| 68 | ADVHSQHHHHHHHHV | Peptide_005 |
| 69 | DVHSQHHHHHHHVK | Peptide_006 |
| 70 | VHSQHHHHHHHVKQ | Peptide_007 |
| 71 | HSQHHHHHHHVKQI | Peptide_008 |
| 72 | SQHHHHHHHVKQIE | Peptide_009 |
| 73 | QHHHHHHHVKQIES | Peptide_010 |
| 74 | HHHHHHHHVKQIESK | Peptide_011 |
| 75 | HHHHHHHVKQIESKT | Peptide_012 |
| 76 | HHHHHHVKQIESKTA | Peptide_013 |
| 77 | HHHHHVKQIESKTAF | Peptide_014 |
| 78 | HHHHVKQIESKTAFQ | Peptide_015 |
| 79 | HHHVKQIESKTAFQE | Peptide_016 |
| 80 | HHVKQIESKTAFQEA | Peptide_017 |
| 81 | HVKQIESKTAFQEAL | Peptide_018 |
| 82 | VKQIESKTAFQEALD | Peptide_019 |
| 83 | KQIESKTAFQEALDA | Peptide_020 |
| 84 | QIESKTAFQEALDAA | Peptide_021 |
| 85 | IESKTAFQEALDAAG | Peptide_022 |
| 86 | ESKTAFQEALDAAGD | Peptide_023 |
| 87 | SKTAFQEALDAAGDK | Peptide_024 |
| 88 | KTAFQEALDAAGDKL | Peptide_025 |
| 89 | TAFQEALDAAGDKLV | Peptide_026 |
| 90 | AFQEALDAAGDKLVV | Peptide_027 |
| 91 | FQEALDAAGDKLVVV | Peptide_028 |
| 92 | QEALDAAGDKLVVVD | Peptide_029 |
| 93 | EALDAAGDKLVVVDF | Peptide_030 |
| 94 | ALDAAGDKLVVVDFS | Peptide_031 |
| 95 | LDAAGDKLVVVDFSA | Peptide_032 |
| 96 | DAAGDKLVVVDFSAT | Peptide_033 |
| 97 | AAGDKLVVVDFSATW | Peptide_034 |
| 98 | AGDKLVVVDFSATWC | Peptide_035 |
| 99 | GDKLVVVDFSATWCG | Peptide_036 |
| 100 | DKLVVVDFSATWCGP | Peptide_037 |
| 101 | KLVVVDFSATWCGPC | Peptide_038 |

TABLE 21

Peptides immobilized on microarrays

| SEQ ID NO: | Amino acid sequence | Name |
|---|---|---|
| 102 | LVVVDFSATWCGPCK | Peptide_039 |
| 103 | VVVDFSATWCGPCKM | Peptide_040 |
| 104 | VVDFSATWCGPCKMI | Peptide_041 |
| 105 | VDFSATWCGPCKMIK | Peptide_042 |
| 106 | DFSATWCGPCKMIKP | Peptide_043 |
| 107 | FSATWCGPCKMIKPF | Peptide_044 |
| 108 | SATWCGPCKMIKPFF | Peptide_045 |
| 109 | ATWCGPCKMIKPFFH | Peptide_046 |
| 110 | TWCGPCKMIKPFFHS | Peptide_047 |
| 111 | WCGPCKMIKPFFHSL | Peptide_048 |
| 112 | CGPCKMIKPFFHSLS | Peptide_049 |
| 113 | GPCKMIKPFFHSLSE | Peptide_050 |
| 114 | PCKMIKPFFHSLSEK | Peptide_051 |
| 115 | CKMIKPFFHSLSEKY | Peptide_052 |
| 116 | KMIKPFFHSLSEKYS | Peptide_053 |
| 117 | MIKPFFHSLSEKYSN | Peptide_054 |
| 118 | IKPFFHSLSEKYSNV | Peptide_055 |
| 119 | KPFFHSLSEKYSNVI | Peptide_056 |
| 120 | PFFHSLSEKYSNVIF | Peptide_057 |
| 121 | FFHSLSEKYSNVIFL | Peptide_058 |
| 122 | FHSLSEKYSNVIFLE | Peptide_059 |
| 123 | HSLSEKYSNVIFLEV | Peptide_060 |
| 124 | SLSEKYSNVIFLEVD | Peptide_061 |
| 125 | LSEKYSNVIFLEVDV | Peptide_062 |
| 126 | SEKYSNVIFLEVDVD | Peptide_063 |
| 127 | EKYSNVIFLEVDVDD | Peptide_064 |
| 128 | KYSNVIFLEVDVDDC | Peptide_065 |
| 129 | YSNVIFLEVDVDDCQ | Peptide_066 |
| 130 | SNVIFLEVDVDDCQD | Peptide_067 |
| 131 | NVIFLEVDVDDCQDV | Peptide_068 |
| 132 | VIFLEVDVDDCQDVA | Peptide_069 |
| 133 | IFLEVDVDDCQDVAS | Peptide_070 |
| 134 | FLEVDVDDCQDVASE | Peptide_071 |
| 135 | LEVDVDDCQDVASEC | Peptide_072 |
| 136 | EVDVDDCQDVASECE | Peptide_073 |
| 137 | VDVDDCQDVASECEV | Peptide_074 |
| 138 | DVDDCQDVASECEVK | Peptide_075 |
| 139 | VDDCQDVASECEVKC | Peptide_076 |

TABLE 22

Peptides immobilized on microarrays

| SEQ ID NO: | Amino acid sequence | Name |
|---|---|---|
| 140 | DDCQDVASECEVKCM | Peptide_077 |
| 141 | DCQDVASECEVKCMP | Peptide_078 |
| 142 | CQDVASECEVKCMPT | Peptide_079 |
| 143 | QDVASECEVKCMPTF | Peptide_080 |
| 144 | DVASECEVKCMPTFQ | Peptide_081 |
| 145 | VASECEVKCMPTFQF | Peptide_082 |
| 146 | ASECEVKCMPTFQFF | Peptide_083 |
| 147 | SECEVKCMPTFQFFK | Peptide_084 |
| 148 | ECEVKCMPTFQFFKK | Peptide_085 |
| 149 | CEVKCMPTFQFFKKG | Peptide_086 |
| 150 | EVKCMPTFQFFKKGQ | Peptide_087 |
| 151 | VKCMPTFQFFKKGQK | Peptide_088 |
| 152 | KCMPTFQFFKKGQKV | Peptide_089 |
| 153 | CMPTFQFFKKGQKVG | Peptide_090 |
| 154 | MPTFQFFKKGQKVGE | Peptide_091 |
| 155 | PTFQFFKKGQKVGEF | Peptide_092 |
| 156 | TFQFFKKGQKVGEFS | Peptide_093 |
| 157 | FQFFKKGQKVGEFSG | Peptide_094 |
| 158 | QFFKKGQKVGEFSGA | Peptide_095 |
| 159 | FFKKGQKVGEFSGAN | Peptide_096 |
| 160 | FKKGQKVGEFSGANK | Peptide_097 |
| 161 | KKGQKVGEFSGANKE | Peptide_098 |
| 162 | KGQKVGEFSGANKEK | Peptide_099 |
| 163 | GQKVGEFSGANKEKL | Peptide_100 |
| 164 | QKVGEFSGANKEKLE | Peptide_101 |
| 165 | KVGEFSGANKEKLEA | Peptide_102 |
| 166 | VGEFSGANKEKLEAT | Peptide_103 |
| 167 | GEFSGANKEKLEATI | Peptide_104 |
| 168 | EFSGANKEKLEATIN | Peptide_105 |
| 169 | FSGANKEKLEATINE | Peptide_106 |

TABLE 22-continued

Peptides immobilized on microarrays

| SEQ ID NO: | Amino acid sequence | Name |
|---|---|---|
| 170 | SGANKEKLEATINEL | Peptide_107 |
| 171 | GANKEKLEATINELV | Peptide_108 |

Full-length mouse IgG was co-immobilized on a microarray slide as an assay control, and an additional sequence was included in the peptide library by JPT as an inner process control.

17-2. Assay Conditions

Profiling experiments were performed using a total of two antibody samples (B266-1 and B264) diluted in a blocking buffer (Pierce International, Superblock TBS T20, order #37536). 5, 1, 0.2, 0.04, 0.008 and 0.0016 µg/mL serial dilutions were incubated on a single multi-well microarray slide at 30° C. for 1 hour. The slide includes 21 individual mini-arrays (one mini-array per sample dilution).

After sample incubation, 1 µg/ml of a fluorescence-labeled secondary anti-mouse-IgG antibody (anti-mouse IgG(H+L) (Thermo 84545)) was added to a corresponding well, followed by a reaction for 1 hour. DyLight 650 was used as a label. False-positive binding to a peptide was evaluated by performing one additional control incubation in which only a secondary antibody was applied on the same microarray slide. Before performing each step, the microarrays were washed with a washing buffer.

After washing and drying, the slide was scanned using a 635-nm high-resolution laser scanner (Axon GenePix Scanner 4300 SL50) to obtain fluorescence intensity profiles, and the obtained image was quantified using spot-recognition software, GenePix, to calculate the average pixel value for each peptide. For each spot, the average signal intensity was extracted (light units between 0 and 65535).

17-3. Image of Processed Arrays

Figure 20:
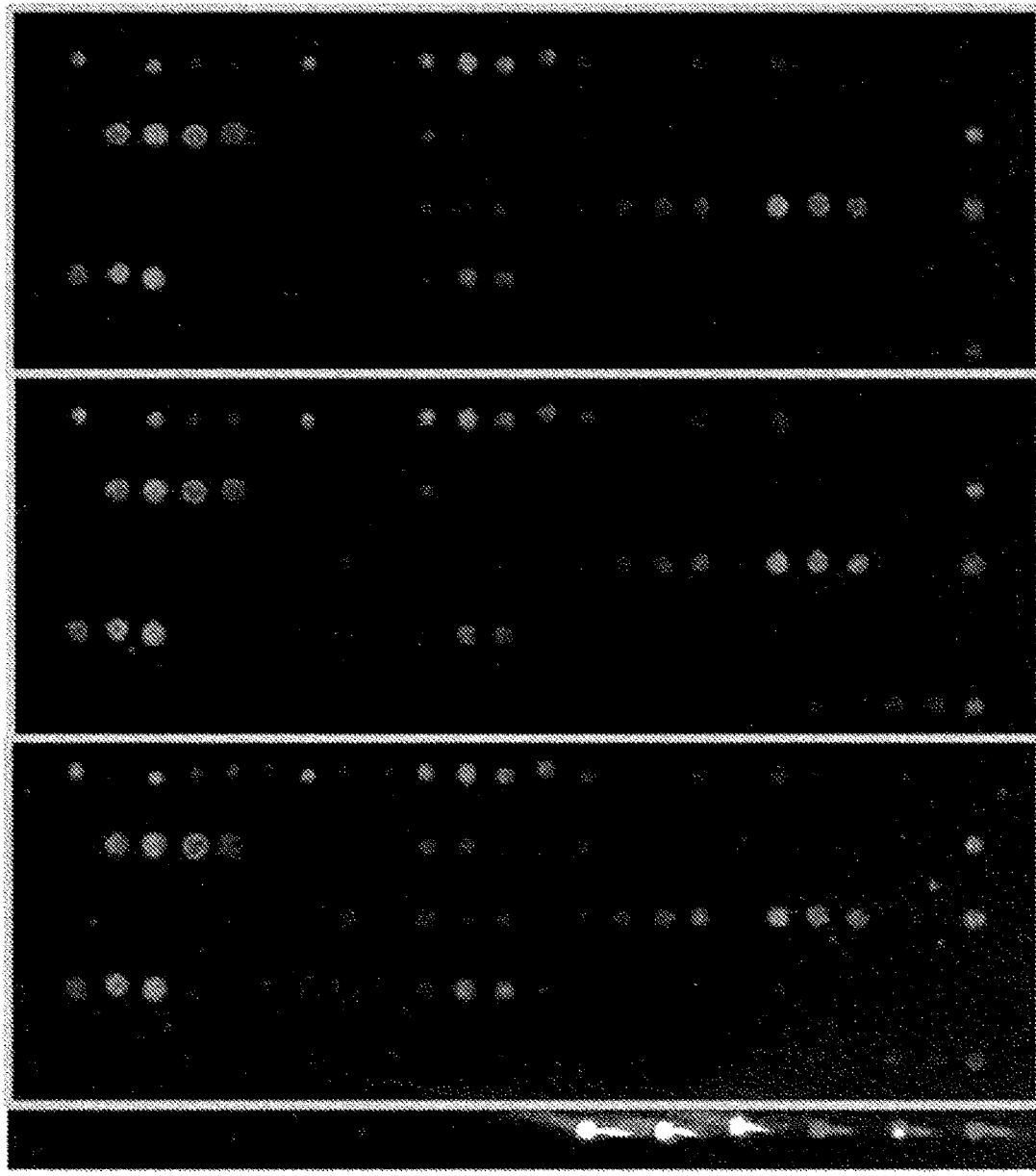
FIG. 20 is an image of mini-arrays cultured with one of the antibody samples described in Example 17.
Figure 21A:
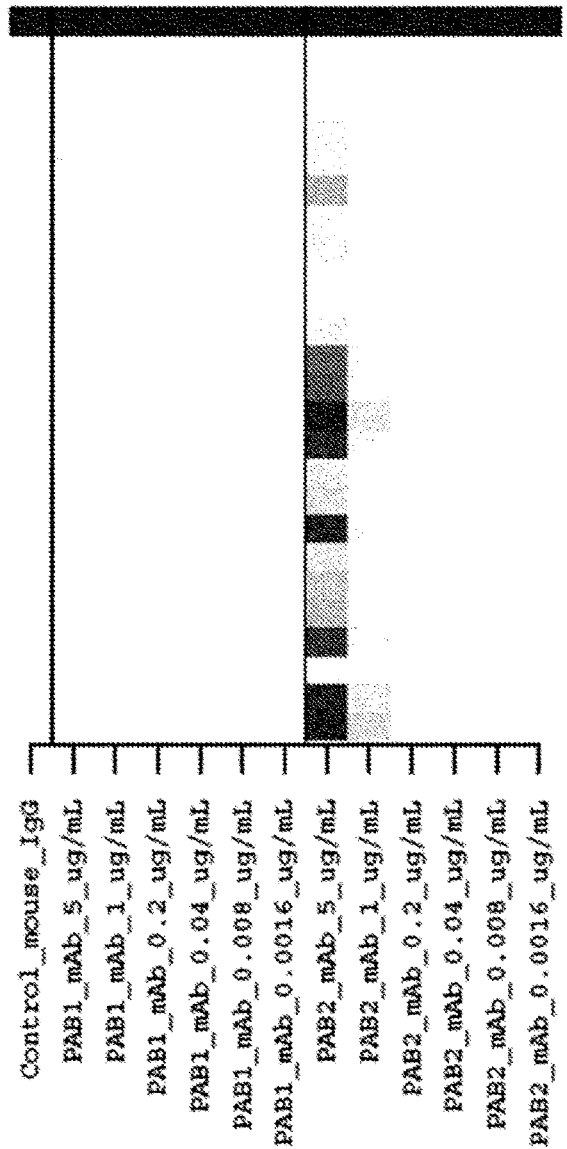
Figure 21D:
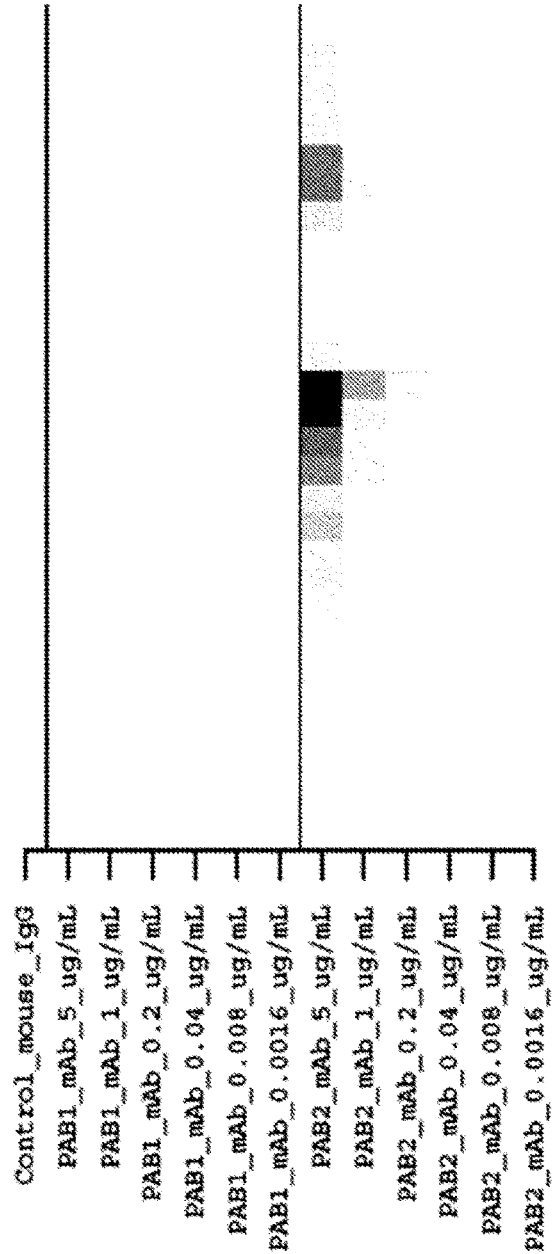

An exemplary fluorescence readout image of a mini-array cultured with one of the antibody samples is shown in FIG. 20. Low background levels were observed in all samples. Black indicates no signal, red shadow indicates an increase in detected signal intensity, white indicates detector saturation, and each individual subarray is outlined in green.

17-4. Heatmap Evaluation

To visualize the obtained results and compare binding regions across individual cultures, as shown in FIGS. 21A to 21D, heatmap diagrams were calculated. In FIGS. 21A to 21D, the fluorescence intensity is expressed in a color-coded manner, white indicates no binding, and red indicates strong binding. For all evaluations, the MMC2-value of the average pixel fluorescence for each peptide was calculated.

MMC2 is the same as the average value of all three cases on a microarray except when the coefficient of variation (CV), which is the standard deviation divided by the average value, is larger than 0.5. In this case, the average of the two closest values (MC2) is assigned to MMC2. The thick black line in the heatmap indicates the culture of a control only using a secondary anti-mouse IgG antibody. The culture of individual antibody samples is indicated by a thin blue line.

In the case of the antibody B266-1, as shown in Table 23, the highest signal, approximately 8-fold the average background level, was detected for Peptide_004 and Peptide_005 (SEQ ID NOs: 67 and 68). However, since Peptide_004 and Peptide_005 are not native forms, these peptides were excluded from an epitope candidate group.

TABLE 23

B266-1 (Ab1)

| Description | ID | NAME | Control IgG | 5 ug | 1 ug | 0.2 ug | 0.04 ug | 0.08 ug | 0.0016 ug |
|---|---|---|---|---|---|---|---|---|---|
| Negative control | AA | blank-control | 1 | 1 | 1 | 1 | 1 | 1 | 1 |
| Positive Control | Human_IgG | Control-Spot | 46.60 | 35.79 | 52.82 | 49.65 | 49.71 | 47.85 | 35.43 |
|  | Mouse_IgG | Control-Spot | 54.60 | 46.96 | 65.38 | 71.40 | 79.65 | 74.60 | 84.79 |
| It is not native form but recombinant insert region. | AADVHSQHHHHHHHH | Peptide_004 | 0.87 | 6.78 | 2.71 | 1.41 | 1.14 | 1.00 | 0.99 |
|  | ADVHSQHHHHHHHV | Peptide_005 | 1.07 | 7.63 | 3.58 | 1.78 | 1.60 | 1.28 | 1.60 |
|  | ATWCGPCKMIKPFFH | Peptide_046 | 1.56 | 6.41 | 3.18 | 2.00 | 1.96 | 1.64 | 1.79 |
|  | TWCGPCKMIKPFFHS | Peptide_047 | 1.11 | 5.58 | 2.25 | 1.58 | 1.50 | 1.11 | 1.18 |
|  | WCGPCKMIKPFFHSL | Peptide_048 | 4.63 | 6.10 | 6.00 | 5.99 | 6.57 | 7.25 | 7.61 |
|  | CGPCKMIKPFFHSLS | Peptide_049 | 1.25 | 2.89 | 1.96 | 1.45 | 1.51 | 1.31 | 1.37 |
|  | GPCKMIKPFFHSLSE | Peptide_050 | 0.42 | 2.19 | 1.09 | 0.65 | 0.68 | 0.52 | 0.62 |
|  | PCKMIKPFFHSLSEK | Peptide_051 | 0.47 | 1.24 | 0.81 | 0.61 | 0.62 | 0.60 | 0.83 |
|  | CKMIKPFFHSLSEKY | Peptide_052 | 1.18 | 3.84 | 2.38 | 1.38 | 1.23 | 1.12 | 1.37 |
|  | KMIKPFFHSLSEKYS | Peptide_053 | 1.16 | 2.45 | 2.13 | 1.66 | 1.35 | 1.44 | 1.42 |
|  | MIKPFFHSLSEKYSN | Peptide_054 | 0.64 | 2.36 | 1.15 | 0.84 | 0.71 | 0.71 | 0.73 |
|  | IKPFFHSLSEKYSNV | Peptide_055 | 0.83 | 2.08 | 1.38 | 1.04 | 1.41 | 0.85 | 1.05 |
|  | KPFFHSLSEKYSNVI | Peptide_056 | 1.09 | 2.89 | 1.84 | 1.24 | 1.11 | 1.07 | 1.18 |
|  | PFFHSLESKYSNVIF | Peptide_057 | 1.83 | 2.39 | 2.07 | 1.94 | 1.87 | 2.09 | 1.93 |
|  | PTFQFFKKGQKVGEF | Peptide_092 | 2.28 | 3.50 | 2.62 | 1.86 | 1.62 | 1.33 | 1.75 |

The antibody B264 showed a concentration-dependent signal profile, and considerably strong interactions with some peptides. The most significant binding was obtained with peptides listed in Table 24 below, particularly at two highest culture sample concentrations.

As shown in Table 24, the highest signal, approximately 7-fold the average background level, was measured for Peptide_012 and Peptide_018 (SEQ ID NOs: 75 and 81).

However, since the Peptide_012 and Peptide_018 are not native forms, they were excluded from an epitope candidate group.

Subsequently, the peptides of SEQ ID NOs: 82 to 88, corresponding to Peptide_019 to Peptide_025 for which the strongest signal was measured were expected to be antibody B264-binding sites, and "VKQIESK-TAFQEALDAAGDKL" (SEQ ID NO: 174) was finally determined as an epitope of the antibody B264.

Afterward, the peptides of SEQ ID NO: 109 to SEQ ID NO: 120, corresponding to Peptide_046 to Peptide-057 for which the strongest signal was measured were expected to be antibody B264-binding sites, which has the same epitope as a B266-1-binding site.

TABLE 24

B264 (Ab2)

| Description | ID | NAME | Control IgG | 5 ug | 1 ug | 0.2 ug | 0.04 ug | 0.08 ug | 0.0016 ug |
|---|---|---|---|---|---|---|---|---|---|
| Negative control | AA | blank-control | 1 | 1 | 1 | 1 | 1 | 1 | 1 |
| Positive Control | Human_IgG | Control Spot | 46.60 | 6.70 | 20.77 | 36.30 | 48.06 | 52.63 | 45.73 |
|  | Mouse_IgG | Control-Spot | 54.60 | 7.16 | 24.51 | 46.01 | 69.54 | 76.34 | 74.50 |
| It is not native form but recombinant insert region. | HHHHHHHVKQIESKT | Peptide_012 | 0.74 | 4.49 | 3.65 | 1.72 | 1.15 | 0.88 | 0.81 |
|  | HHHHHHVKQIESKTA | Peptide_013 | 0.88 | 4.87 | 4.05 | 1.85 | 1.40 | 0.95 | 0.75 |
|  | HHHHHVKQIESKTAF | Peptide_014 | 0.83 | 6.90 | 6.71 | 3.16 | 1.49 | 1.14 | 0.69 |
|  | HHHHVKQIESKTAFQ | Peptide_015 | 0.54 | 5.96 | 5.11 | 2.50 | 1.69 | 0.79 | 0.58 |
|  | HVKQIESKTAFQEAL | Peptide_018 | 0.74 | 6.15 | 5.52 | 3.49 | 1.64 | 0.85 | 0.68 |
|  | VKQIESKTAFQEALD | Peptide_019 | 0.96 | 1.98 | 1.67 | 1.48 | 1.20 | 1.02 | 0.85 |
|  | KQIESKTAFQEALDA | Peptide_020 | 0.82 | 2.41 | 2.30 | 1.84 | 1.33 | 0.80 | 0.71 |
|  | QIESKTAFQEALDAA | Peptide_021 | 0.80 | 2.69 | 2.48 | 2.08 | 1.35 | 0.84 | 0.73 |
|  | IESKTAFQEALDAAG | Peptide_022 | 0.76 | 5.54 | 5.88 | 4.20 | 2.89 | 1.00 | 0.72 |
|  | ESKTAFQEALDAAGD | Peptide_023 | 1.02 | 1.26 | 1.19 | 1.12 | 1.15 | 0.91 | 0.78 |
|  | SKTAFQEALDAAGDK | Peptide_024 | 0.87 | 6.09 | 6.50 | 4.00 | 2.38 | 1.00 | 0.72 |
|  | KTAFQEALDAAGDKL | Peptide_025 | 1.00 | 6.49 | 7.24 | 4.90 | 2.39 | 1.03 | 0.88 |
|  | FSATQCGPCKMIKPF | Peptide_044 | 1.73 | 3.33 | 2.93 | 2.30 | 2.12 | 1.87 | 1.60 |
|  | SATWCGPCKMIKPFF | Peptide_045 | 4.14 | 4.90 | 5.11 | 4.58 | 4.59 | 5.89 | 4.08 |
|  | ATWCGPCKMIKPFFH | Peptide_046 | 1.56 | 6.20 | 5.62 | 3.44 | 2.87 | 2.11 | 1.69 |
|  | TWCGPCKMIKPFFHS | Peptide_047 | 1.11 | 4.89 | 4.07 | 2.52 | 1.97 | 1.52 | 1.15 |
|  | WCGPCKMIKPFFHSL | Peptide_048 | 4.63 | 2.15 | 3.91 | 4.61 | 6.34 | 7.68 | 7.46 |
|  | CGPCKMIKPFFHSLS | Peptide_049 | 1.25 | 1.11 | 1.20 | 1.34 | 1.48 | 1.43 | 1.18 |
|  | GPCKMIKPFFHSLSE | Peptide_050 | 0.42 | 0.54 | 0.47 | 0.46 | 0.64 | 0.65 | 0.51 |
|  | PCKMIKPFFHSLSEK | Peptide_051 | 0.47 | 4.28 | 3.91 | 2/32 | 1.41 | 0.70 | 0.58 |
|  | CKMIKPFFHSLSEKY | Peptide_052 | 1.18 | 5.14 | 4.43 | 2.56 | 2.02 | 1.23 | 1.15 |
|  | KMIKPFFHSLSEKYS | Peptide_053 | 1.16 | 6.49 | 8.52 | 4.75 | 2.54 | 1.76 | 1.41 |
|  | MIKPFFHSLSEKYSN | Peptide_054 | 0.64 | 1.46 | 1.43 | 0.89 | 0.99 | 0.63 | 0.55 |
|  | IKPFFHSLSEKYSNV | Peptide_055 | 0.83 | 3.57 | 3.26 | 2.21 | 1.51 | 0.99 | 0.81 |
|  | KPFFHSLSEKYSNVI | Peptide_056 | 1.09 | 2.86 | 2.58 | 1.72 | 1.35 | 1.11 | 0.99 |
|  | PFFHSLSEKYSNVIF | Peptide_057 | 1.83 | 2.44 | 2.19 | 2.08 | 2.15 | 2.27 | 1.73 |
|  | SECEVKCMPTFQFFK | Peptide_084 | 0.99 | 3.79 | 3.26 | 2.36 | 1.83 | 1.33 | 0.97 |
|  | ECEVKCMPTFQFFKK | Peptide_085 | 0.64 | 3.87 | 3.56 | 2.23 | 1.48 | 0.90 | 0.65 |
|  | CEVKCMPTFQFFKKG | Peptide_086 | 0.79 | 1.90 | 1.56 | 1.16 | 1.14 | 1.02 | 0.82 |
|  | PTFQFFKKGQKVGEF | Peptide_092 | 2.28 | 6.78 | 9.76 | 6.81 | 5.18 | 3.07 | 1.86 |
|  | TFQFFKKGQKVGEFS | Peptide_093 | 1.21 | 6.18 | 5.33 | 3.72 | 2.46 | 1.53 | 1.12 |
|  | FQFFKKGQKVGEFSG | Peptide_094 | 0.63 | 4.13 | 3.26 | 2.11 | 1.49 | 1.00 | 0.62 |
|  | QFFKKGQKVGEFSGA | Peptide_095 | 1.44 | 3.44 | 3.52 | 2.13 | 1.66 | 1.15 | 1.07 |
|  | FFKKGQKVGEFSGAN | Peptide_096 | 1.18 | 1.90 | 2.04 | 1.37 | 1.44 | 0.94 | 0.82 |
|  | FKKGQKVGEFSGANK | Peptide_097 | 1.34 | 2.26 | 2.18 | 1.68 | 1.31 | 1.08 | 0.91 |

No significant binding was detected in culture of a secondary antibody control. Strong signals up to the saturation level were obtained at a spot of the control containing full-length mouse IgG during all cultures, indicating excellent analysis performance.

The epitope regions obtained through the above-described procedures are shown in Table 25 below, and as a result of confirming tertiary (33) structures by 3D filing by downloading the NMR sequence of hTrx1 certified through a protein database (PDB), as shown in FIGS. 22A to 22F, when native forms, their sequences are present at the outside thereof, confirming that the peptides can serve as epitopes.

TABLE 25

Figure 22A:
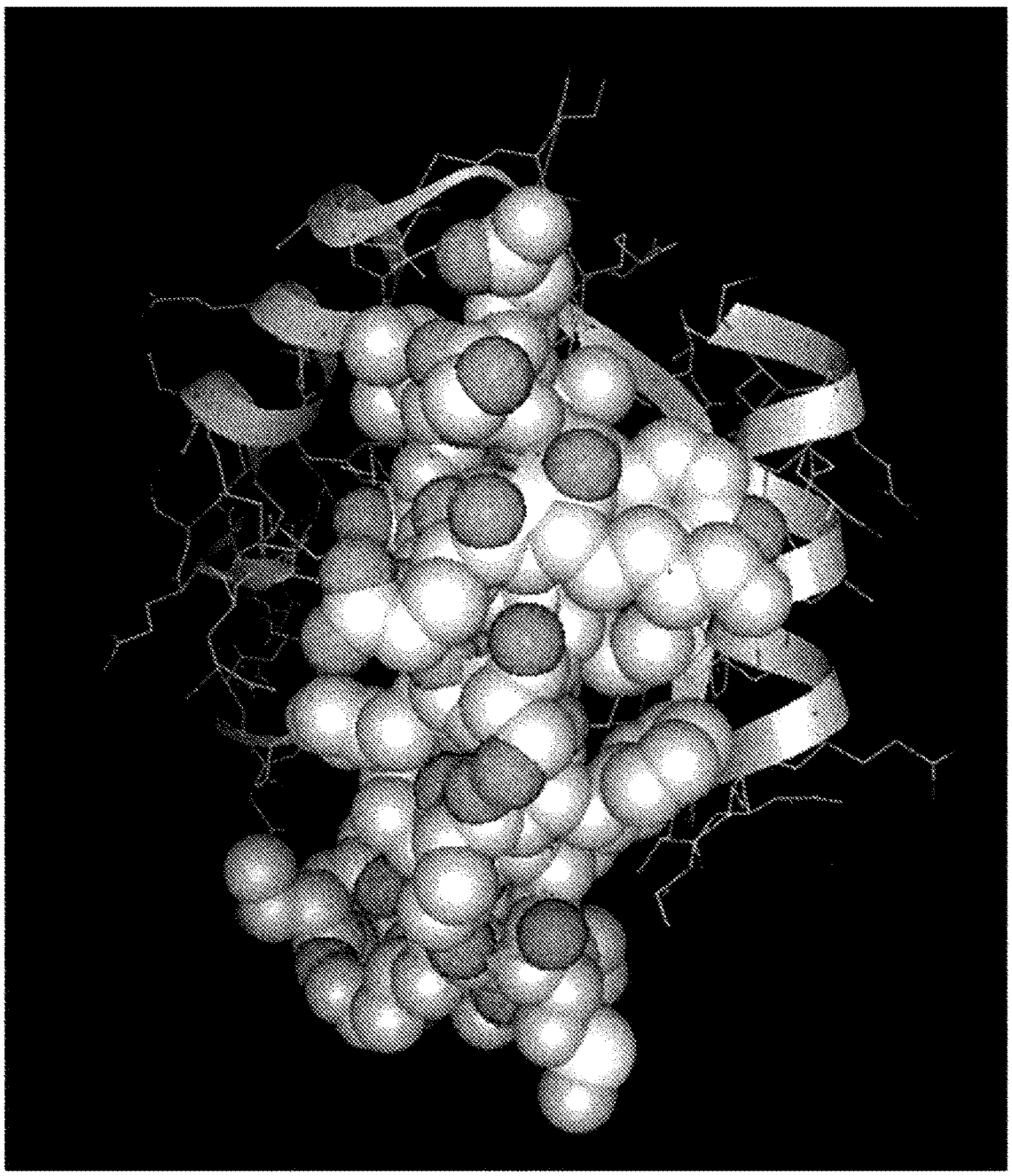
FIGS. 22A to 22F are images of confirming the position of an epitope in the three-dimensional structure of a hTrx1 protein.
Figure 22B:
Figure 22C:
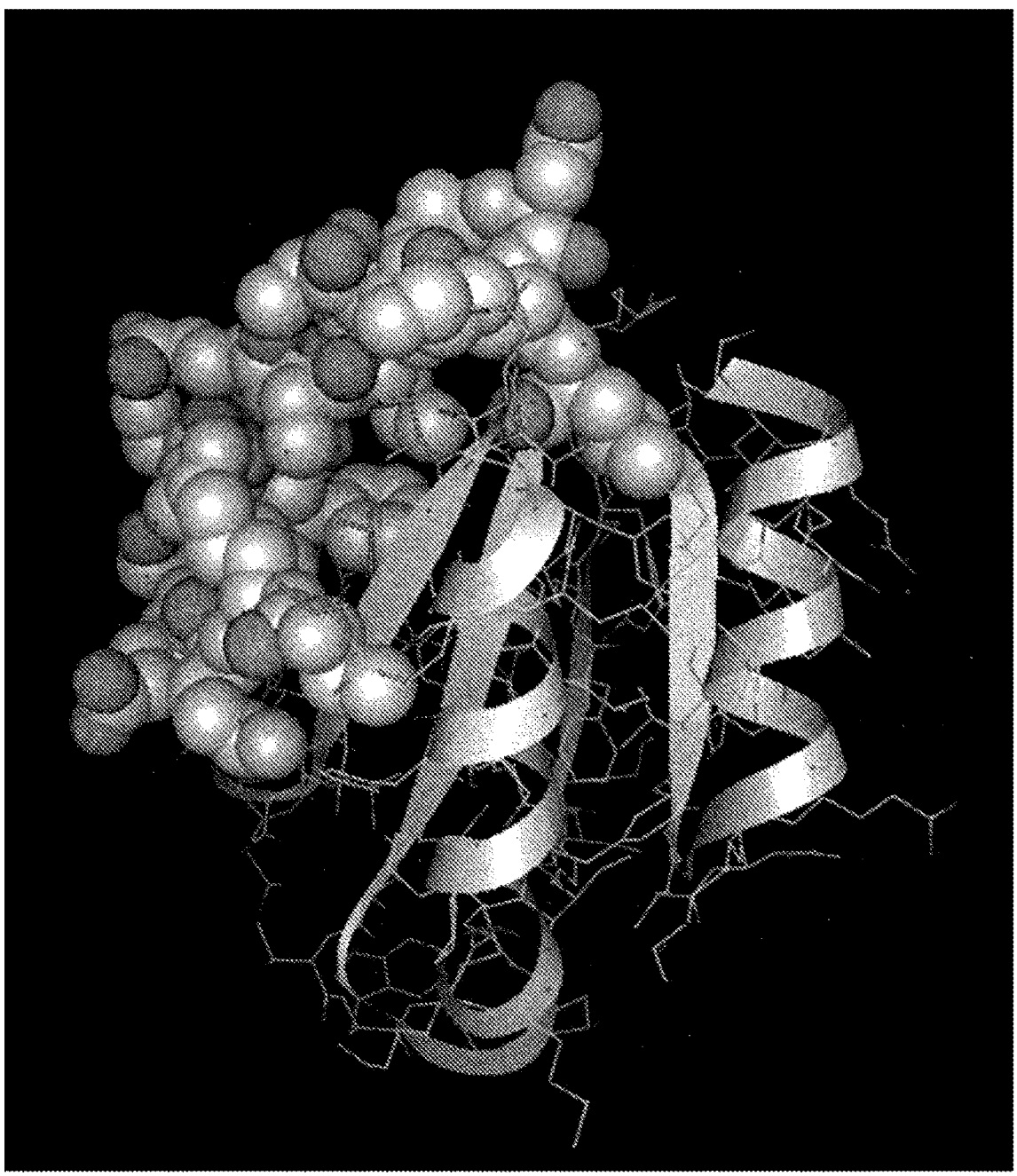
Figure 22D:
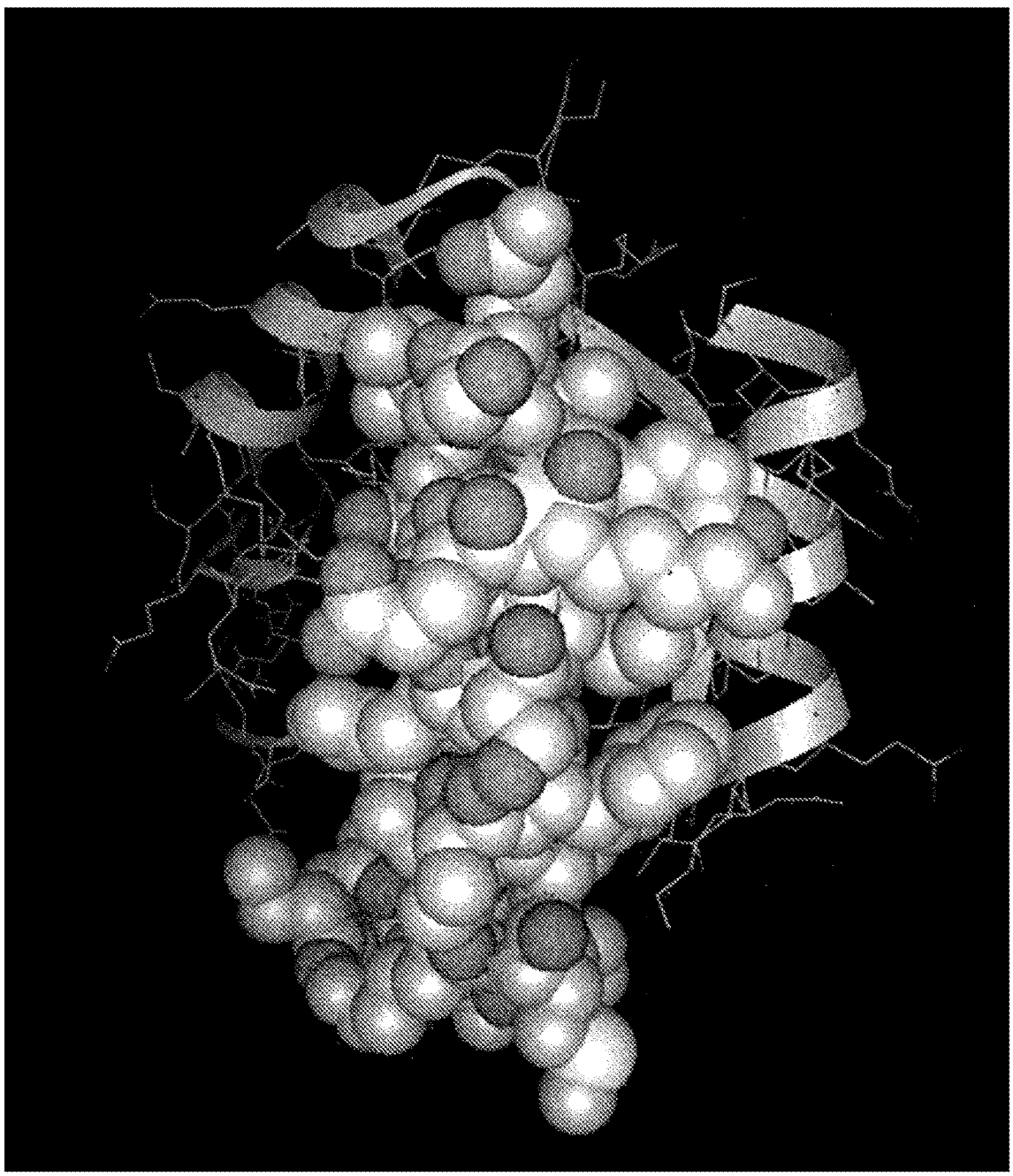
Figure 22E:
Figure 22F:

| Tertiary (3D) structure | Amino acid sequence | Gene sequence | Comparison with Example 13 | Description |
|---|---|---|---|---|
| FIGS. 22A, 22D | ATWCGPCKMIKPFFHS LSEKYSNVIF (SEQ ID NO: 172) | gctacctggtgcggcccgtgta aaatgattaaaccgttttccata gcctgtctgaaaaatacagtaa cgttatcttt (SEQ ID NO: 177) | Including M4 region | Epitopes of antibodies B264 and B266-1 |
| FIG. 22B | PTFQFFKKGQKVGEF (SEQ ID NO: 173) | ccgacgttccagtttttcaaaaa aggtcaaaaagtcggtgaattt (SEQ ID NO: 178) | Including M6 region | Epitope of antibody B266-1 |
| FIG. 22C | VKQIESKTAFQEALD AAGDKL (SEQ ID NO: 174) | gtcaaacagatcgaatcaaaa accgcatttcaagaagccctgg acgccgctggtgacaaactg (SEQ ID NO: 179) | Integration of M1 and M2 regions | Epitope of antibody B264 |
| FIG. 22E | SECEVKCMPTFQFFKKG (SEQ ID NO: 175) | agcgaatgcgaagtgaaatgt atgccgacgttccagtttttcaa aaaaggt (SEQ ID NO: 180) | Including M6 region | Epitope of antibody B264 |
| FIG. 22F | PTFQFFKKGQKVGEFS GANK (SEQ ID NO: 176) | ccgacgttccagtttttcaaaaa aggtcaaaaagtcggtgaattt agcggtgccaacaaa (SEQ ID NO: 181) | Including M6 region | Epitope of antibody B264 |

The monoclonal antibody of the present invention can very specifically bind to Trx1 due to excellent binding affinity therefor, and can be effectively used in screening of breast cancer patients due to very high sensitivity and specificity. Further, the accuracy and reliability of breast cancer diagnosis can significantly increase because exceptionally high sensitivity and specificity are exhibited by detecting the monoclonal antibody of the present invention, which specifically binds to Trx1, rather than detecting CA15-3, another conventional breast cancer diagnostic biomarker. An epitope region of a human Trx1 antigen to which the antibody of the present invention binds can be effectively used in development of an improved antibody to enhance the binding affinity of an anti-Trx1 antibody.

The invention claimed is:

1. An epitope recognized by a monoclonal antibody specifically binding to thioredoxin-1 (Trx1) or an antigen-binding fragment thereof, wherein the monoclonal antibody comprises: a light chain variable region, which includes a light chain CDR1 consisting of the amino acid sequence of SEQ ID NO: 1, a light chain CDR2 consisting of the amino acid sequence of SEQ ID NO: 2 and a light chain CDR3 consisting of the amino acid sequence of SEQ ID NO: 3; and a heavy chain variable region, which includes a heavy chain CDR1 consisting of the amino acid sequence of SEQ ID NO: 4, a heavy chain CDR2 consisting of the amino acid sequence of SEQ ID NO: 5 and a heavy chain CDR3 consisting of the amino acid sequence of SEQ ID NO: 6; or a light chain variable region which includes a light chain CDR1 consisting of the amino acid sequence of SEQ ID NO: 7, a light chain CDR2 consisting of the amino acid sequence of SEQ ID NO: 8 and a light chain CDR3 consisting of the amino acid sequence of SEQ ID NO: 9; and a heavy chain variable region, which includes a heavy chain CDR1 consisting of the amino acid sequence of SEQ ID NO: 10, a heavy chain CDR2 consisting of the amino acid sequence of SEQ ID NO: 11 and a heavy chain CDR3 consisting of the amino acid sequence of SEQ ID NO: 12, wherein the epitope consists of any one amino acid sequence selected from SEQ ID Nos: 32 to 34 or 172, 174 and 175.

2. The epitope according to claim 1, wherein the antibody comprises:
a light chain variable region consisting of the amino acid sequence of SEQ ID NO: 13 and a heavy chain variable region consisting of the amino acid sequence of SEQ ID NO: 14; or
a light chain variable region consisting of the amino acid sequence of SEQ ID NO: 15 and a heavy chain variable region consisting of the amino acid sequence of SEQ ID NO: 16.

3. The epitope according to claim 1, wherein the antibody comprises:
a light chain consisting of the amino acid sequence of SEQ ID NO: 17 and a heavy chain consisting of the amino acid sequence of SEQ ID NO: 18;
a light chain consisting of the amino acid sequence of SEQ ID NO: 19 and a heavy chain consisting of the amino acid sequence of SEQ ID NO: 20; or
a light chain consisting of the amino acid sequence of SEQ ID NO: 25 and a heavy chain consisting of the amino acid sequence of SEQ ID NO: 26.

4. The epitope according to claim 1, wherein the thioredoxin-1 (Trx1) is a human thioredoxin-1.

5. A nucleic acid molecule encoding the epitope of claim 1.

6. The nucleic acid molecule of claim 5, which consists of any one nucleotide sequence selected from the group consisting of SEQ ID NOs: 35 to 37 and 177, 179 and 180.

7. A recombinant vector comprising the nucleic acid molecule of claim 5.

8. A method of binding a monoclonal antibody specifically binding to thioredoxin-1 (Trx1) or an antigen-binding fragment thereof to an epitope consisting of an amino acid sequence of SEQ ID NO: 173 or 176, wherein the monoclonal antibody comprises:

a light chain variable region, which includes a light chain CDR1 consisting of the amino acid sequence of SEQ ID NO: 1, a light chain CDR2 consisting of the amino acid sequence of SEQ ID NO: 2 and a light chain CDR3 consisting of the amino acid sequence of SEQ ID NO: 3; and a heavy chain variable region, which includes a heavy chain CDR1 consisting of the amino acid sequence of SEQ ID NO: 4, a heavy chain CDR2 consisting of the amino acid sequence of SEQ ID NO: 5 and a heavy chain CDR3 consisting of the amino acid sequence of SEQ ID NO: 6; or a light chain variable region which includes a light chain CDR1 consisting of the amino acid sequence of SEQ ID NO: 7, a light chain CDR2 consisting of the amino acid sequence of SEQ ID NO: 8 and a light chain CDR3 consisting of the amino acid sequence of SEQ ID NO: 9; and a heavy chain variable region, which includes a heavy chain CDR1 consisting of the amino acid sequence of SEQ ID NO: 10, a heavy chain CDR2 consisting of the amino acid sequence of SEQ ID NO: 11 and a heavy chain CDR3 consisting of the amino acid sequence of SEQ ID NO: 12.

9. The method according to claim 8, wherein the antibody comprises:
a light chain variable region consisting of the amino acid sequence of SEQ ID NO: 13 and a heavy chain variable region consisting of the amino acid sequence of SEQ ID NO: 14; or
a light chain variable region consisting of the amino acid sequence of SEQ ID NO: 15 and a heavy chain variable region consisting of the amino acid sequence of SEQ ID NO: 16.

10. The method according to claim 8, wherein the antibody comprises:
a light chain consisting of the amino acid sequence of SEQ ID NO: 17 and a heavy chain consisting of the amino acid sequence of SEQ ID NO: 18;
a light chain consisting of the amino acid sequence of SEQ ID NO: 19 and a heavy chain consisting of the amino acid sequence of SEQ ID NO: 20; or
a light chain consisting of the amino acid sequence of SEQ ID NO: 25 and a heavy chain consisting of the amino acid sequence of SEQ ID NO: 26.

11. The method according to claim 8, wherein the thioredoxin-1 (Trx1) is a human thioredoxin-1.

* * * * *

SEQUENCE LISTING

<160> NUMBER OF SEQ ID NOS: 215

<210> SEQ ID NO 1
<211> LENGTH: 11
<212> TYPE: PRT
<213> ORGANISM: Artificial Sequence
<220> FEATURE:
<223> OTHER INFORMATION: B264 light chain CDR1

<400> SEQUENCE: 1

Gln Ser Ile Val His Ser Asn Gly Asn Thr Tyr
1               5                   10

<210> SEQ ID NO 2
<211> LENGTH: 3
<212> TYPE: PRT

```
<213> ORGANISM: Artificial Sequence
<220> FEATURE:
<223> OTHER INFORMATION: B264 light chain CDR2

<400> SEQUENCE: 2

Lys Val Ser
1

<210> SEQ ID NO 3
<211> LENGTH: 10
<212> TYPE: PRT
<213> ORGANISM: Artificial Sequence
<220> FEATURE:
<223> OTHER INFORMATION: B264 light chain CDR3

<400> SEQUENCE: 3

Cys Phe Gln Gly Ser His Val Pro Tyr Thr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: B264 heavy chain CDR1

<400> SEQUENCE: 4

Gly Tyr Thr Phe Thr Ser Tyr Thr
1               5

<210> SEQ ID NO 5
<211> LENGTH: 9
<212> TYPE: PRT
<213> ORGANISM: Artificial Sequence
<220> FEATURE:
<223> OTHER INFORMATION: B264 heavy chain CDR2

<400> SEQUENCE: 5

Ile Asn Pro Thr Ser Asp Tyr Thr Asn
1               5

<210> SEQ ID NO 6
<211> LENGTH: 14
<212> TYPE: PRT
<213> ORGANISM: Artificial Sequence
<220> FEATURE:
<223> OTHER INFORMATION: B264 heavy chain CDR3

<400> SEQUENCE: 6

Phe Cys Ala Ser Glu Gly Gly Phe Leu Tyr Tyr Phe Asp Tyr
1               5                   10

<210> SEQ ID NO 7
<211> LENGTH: 5
<212> TYPE: PRT
<213> ORGANISM: Artificial Sequence
<220> FEATURE:
<223> OTHER INFORMATION: B266-1 light chain CDR1

<400> SEQUENCE: 7

Ser Arg Ile Ser Tyr
1               5

<210> SEQ ID NO 8
<211> LENGTH: 3
<212> TYPE: PRT
<213> ORGANISM: Artificial Sequence
```

```
<220> FEATURE:
<223> OTHER INFORMATION: B266-1 light chain CDR2

<400> SEQUENCE: 8

Asp Thr Ser
1

<210> SEQ ID NO 9
<211> LENGTH: 10
<212> TYPE: PRT
<213> ORGANISM: Artificial Sequence
<220> FEATURE:
<223> OTHER INFORMATION: B266-1 light chain CDR3

<400> SEQUENCE: 9

Cys His Gln Arg Ser Ser Tyr Pro Thr Phe
1               5                   10

<210> SEQ ID NO 10
<211> LENGTH: 8
<212> TYPE: PRT
<213> ORGANISM: Artificial Sequence
<220> FEATURE:
<223> OTHER INFORMATION: B266-1 heavy chain CDR1

<400> SEQUENCE: 10

Gly Phe Asn Ile Lys Asp Thr Phe
1               5

<210> SEQ ID NO 11
<211> LENGTH: 8
<212> TYPE: PRT
<213> ORGANISM: Artificial Sequence
<220> FEATURE:
<223> OTHER INFORMATION: B266-1 heavy chain CDR2

<400> SEQUENCE: 11

Ile Asp Pro Ala Asn Gly Asn Thr
1               5

<210> SEQ ID NO 12
<211> LENGTH: 11
<212> TYPE: PRT
<213> ORGANISM: Artificial Sequence
<220> FEATURE:
<223> OTHER INFORMATION: B266-1 heavy chain CDR3

<400> SEQUENCE: 12

Cys Ala Leu Leu Gln Tyr Ser Ala Met Asp Tyr
1               5                   10

<210> SEQ ID NO 13
<211> LENGTH: 112
<212> TYPE: PRT
<213> ORGANISM: Artificial Sequence
<220> FEATURE:
<223> OTHER INFORMATION: B264 light chain variable region

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 14
<211> LENGTH: 119
<212> TYPE: PRT
<213> ORGANISM: Artificial Sequence
<220> FEATURE:
<223> OTHER INFORMATION: B264 heavy chain variable region

<400> SEQUENCE: 14

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Thr Ser Asp Tyr Thr Asn Tyr Asn Gln Lys Phe
    50                  55                  60

Lys Asp Lys Ala Thr Leu Thr Ala Asp Lys Ser Ser Ser Thr Ala Tyr
65              70                  75                  80

Met Gln Leu Ser Ser Leu Thr Ser Glu Asp Ser Ala Val Tyr Phe Cys
                85                  90                  95

Ala Ser Glu Gly Gly Phe Leu Tyr Tyr Phe Asp Tyr Trp Gly Gln Gly
            100                 105                 110

Thr Thr Leu Thr Val Ser Ser
        115

<210> SEQ ID NO 15
<211> LENGTH: 105
<212> TYPE: PRT
<213> ORGANISM: Artificial Sequence
<220> FEATURE:
<223> OTHER INFORMATION: B266-1 light chain variable region

<400> SEQUENCE: 15

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Ile Ser Tyr Met
                20                  25                  30

Tyr Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Thr Met Glu Ala Glu
65              70                  75                  80

Asp Ala Ala Thr Tyr Tyr Cys His Gln Arg Ser Ser Tyr Pro Thr Phe
                85                  90                  95

Gly Ala Gly Thr Lys Leu Glu Leu Lys
            100                 105

<210> SEQ ID NO 16
```

```
<211> LENGTH: 117
<212> TYPE: PRT
<213> ORGANISM: Artificial Sequence
<220> FEATURE:
<223> OTHER INFORMATION: B266-1 heavy chain variable region

<400> SEQUENCE: 16

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Leu Gln Tyr Ser Ala Met Asp Tyr Trp Gly Gln Gly Thr Ser
            100                 105                 110

Val Thr Val Ser Ser
        115

<210> SEQ ID NO 17
<211> LENGTH: 219
<212> TYPE: PRT
<213> ORGANISM: Artificial Sequence
<220> FEATURE:
<223> OTHER INFORMATION: B264 light chain

<400> SEQUENCE: 17

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
```

-continued

```
                195                 200                 205
        Pro Ile Val Lys Ser Phe Asn Arg Asn Glu Cys
            210                 215

<210> SEQ ID NO 18
<211> LENGTH: 443
<212> TYPE: PRT
<213> ORGANISM: Artificial Sequence
<220> FEATURE:
<223> OTHER INFORMATION: B264 heavy chain

<400> SEQUENCE: 18

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Thr Ser Asp Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Glu Gly Gly Phe Leu Tyr Tyr Phe Asp Tyr Trp Gly Gln Gly
            100                 105                 110

Thr Thr Leu Thr Val Ser Ser Ala Ser Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
```

```
            340                 345                 350
Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440
```

<210> SEQ ID NO 19
<211> LENGTH: 212
<212> TYPE: PRT
<213> ORGANISM: Artificial Sequence
<220> FEATURE:
<223> OTHER INFORMATION: B266 light chain

<400> SEQUENCE: 19

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Ile Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro Thr Phe
                85                  90                  95

Gly Ala Gly Thr Lys Leu Glu Leu Lys Arg Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210
```

<210> SEQ ID NO 20
<211> LENGTH: 452
<212> TYPE: PRT
<213> ORGANISM: Artificial Sequence
<220> FEATURE:
<223> OTHER INFORMATION: B266 heavy chain

<400> SEQUENCE: 20

| | | | | | | | | | | | | | | |
|---|---|---|---|---|---|---|---|---|---|---|---|---|---|---|
|Glu|Val|Gln|Leu|Gln|Gln|Ser|Gly|Ala|Glu|Leu|Val|Lys|Pro|Gly|Ala|
|1| | | |5| | | | |10| | | | |15|

Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Leu Gln Tyr Ser Ala Met Asp Tyr Trp Gly Gln Gly Thr Ser
                100                 105                 110

Val Thr Val Ser Ser Ala Lys Thr Thr Pro Pro Ser Val Tyr Pro Leu
            115                 120                 125

Ala Pro Gly Cys Gly Asp Thr Thr Gly Ser Ser Val Thr Leu Gly Cys
130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
            340                 345                 350

Gln Val Tyr Ile Leu Pro Pro Ala Glu Gln Leu Ser Arg Lys Asp
        355                 360                 365

Val Ser Leu Thr Cys Leu Val Val Gly Phe Asn Pro Gly Asp Ile Ser
370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu

```
                    405                 410                 415
Asn Met Lys Thr Ser Lys Trp Glu Lys Thr Asp Ser Phe Ser Cys Asn
            420                 425                 430

Val Arg His Glu Gly Leu Lys Asn Tyr Tyr Leu Lys Lys Thr Ile Ser
            435                 440                 445

Arg Ser Pro Gly
        450

<210> SEQ ID NO 21
<211> LENGTH: 660
<212> TYPE: DNA
<213> ORGANISM: Artificial Sequence
<220> FEATURE:
<223> OTHER INFORMATION: B264 light chain

<400> SEQUENCE: 21
gacgtgctga tgacacagac accactcagc ctccctgtga gcctgggcga ccaggcctct      60
atttcttgcc ggtctagcca gagcatcgtg cactccaacg caacacata cttggagtgg     120 tatctacaga agcccggcca gtcccctaag ctgctgatat acaaggtgtc taaccgcttc     180
tccggcgtgc ccgacaggtt ctctggcagc ggctctggca ccgacttcac cctcaaaata     240
tctagggtgg aggccgagga cctgggcgtg tactactgct ccagggctc ccacgttcca      300 tacacattcg gcggcggcac aaagttggaa attaagcgcg ctgacgcagc ccaacagtg      360 agcatctttc ctccatcctc tgaacaactt acctctggag gagcctctgt ggtgtgtttc     420
ctgaacaact tctacccaaa ggacatcaat gtgaagtgga gattgatgg ctctgagaga     480 cagaatggag tgctgaactc ctggacagac caggacagca aggacagcac ctacagtatg     540
agtagcaccc tgaccctgac caaggatgaa atgagagac acaactccta cacttgtgag      600
gctacccaca gaccagcac cagcccaatt gtcaaatcct tcaacaggaa tgagtgttaa      660

<210> SEQ ID NO 22
<211> LENGTH: 1332
<212> TYPE: DNA
<213> ORGANISM: Artificial Sequence
<220> FEATURE:
<223> OTHER INFORMATION: B264 heavy chain

<400> SEQUENCE: 22
caggtgcagc tccagcagtc cggcgccgaa ctggccagac tggcgccag cgtgaagatg       60 agctgcaagg cctccggcta cacattcaca tcttacacca tgcactgggt gaagcagaga     120
cccggccagg gctggagtg gattggctac attaacccaa catccgacta cacaaactac     180
aaccagaagt tcaaggacaa ggccacactc accgccgaca gtcttctag cacagcctac     240 atgcagctgt ctagcctgac aagcgaggac tctgccgtgt acttctgcgc ctctgagggc     300
ggcttcctgt actacttcga ctactggggc cagggcacca cctgaccgt gtcctctgcc      360 aaaacgacac cccatctgt ctatccactg gcccctggat ctgctgccca aactaactcc      420
atggtgaccc tgggatgcct ggtcaagggc tatttccctg agccagtgac agtgacctgg     480
aactctggat ccctgtccag cggtgtgcac accttcccag ctgtcctgca gtctgacctc     540
tacactctga gcagctcagt gactgtcccc tccagcacct ggcccagcga gaccgtcacc     600
tgcaacgttg cccacccggc cagcagcacc aaggtggaca agaaaattgt gcccagggat     660
tgtggttgta agccttgcat atgtacagtc ccagaagtat catctgtctt catcttcccc     720
ccaaagccca aggatgtgct caccattact ctgactccta aggtcacgtg tgttgtggta     780
```

```
gacatcagca aggatgatcc cgaggtccag ttcagctggt tgtagatga tgtggaggtg     840 cacacagctc agacgcaacc ccgggaggag cagttcaaca gcactttccg ctcagtcagt     900
gaacttccca tcatgcacca ggactggctc aatggcaagg agttcaaatg cagggtcaac     960
agtgcagctt ccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaga cttcttccct gaagacatta ctgtggagtg cagtggaat    1140 gggcagccag cggagaacta caagaacact cagcccatca tggacacaga tggctcttac    1200
ttcgtctaca gcaagctcaa tgtgcagaag agcaactggg aggcaggaaa tactttcacc    1260
tgctctgtgt tacatgaggg cctgcacaac caccatactg agaagagcct ctcccactct    1320
cctggtaaat aa                                                        1332

<210> SEQ ID NO 23
<211> LENGTH: 639
<212> TYPE: DNA
<213> ORGANISM: Artificial Sequence
<220> FEATURE:
<223> OTHER INFORMATION: B266 light chain

<400> SEQUENCE: 23
cagatcgtgc tcacacagtc tccagccatc atgagcgcct ctcctggcga gaaggtgaca      60
atgacctgct ctgcctctag ccgcatttct tacatgtact ggtatcagca gaagccaggc     120
acctccccta gaggtggat atacgacaca tccaagctgg cctccggcgt gcccgcccgg     180
ttcagcggct ctggcagcgg cacaagctac tccctgacaa ttagcacgat ggaggccgag     240
gacgccgcca catactactg ccaccagcgc tcgtcctacc caacattcgg cgccggcaca     300
aaattggaac tgaagagagc tgacgcagcc caacagtga gcatctttcc tccatcctct     360
gaacaactta cctctggagg agcctctgtg gtgtgtttcc tgaacaactt ctacccaaag     420
gacatcaatg tgaagtggaa gattgatggc tctgagagac agaatggagt gctgaactcc     480
tggacagacc aggacagcaa ggacagcacc tacagtatga gtagcaccct gaccctgacc     540
aaggatgaat atgagagaca caactcctac acttgtgagg ctaccacaa gaccagcacc     600 agcccaattg tcaaatcctt caacaggaat gagtgttaa                           639

<210> SEQ ID NO 24
<211> LENGTH: 1359
<212> TYPE: DNA
<213> ORGANISM: Artificial Sequence
<220> FEATURE:
<223> OTHER INFORMATION: B266 heavy chain

<400> SEQUENCE: 24
gaggtgcagt acaacagtc cggcgccgag ctagtgaagc aggcgccag cgtgaagctg      60 tcttgcacag ccagcggctt caacattaag gacaccttca tgcactgggt gaagcagaga     120
cctgagcagg gcttagagtg gattggccgg atcgaccccg ccaacggcaa cacaaagtac     180
gacccaaagt tccagggcaa ggccacaatt accgccgaca tcttccaa cacagcctac     240 ctccagctgt cgtctctcac cagcgaggac accgccgtgt actactgcgc cctgctccag     300
tactccgcga tggactactg gggccagggc acatctgtga ccgtgtctag cgccaagacc     360 acccccaccat ccgtgtaccc actcgccca ggctgcggcg acaccacagg ctctagcgtg     420
acactgggct gcctggtgaa gggctacttc cccgagtctg tgacagtgac ctggaactct     480
ggctctctgt ctagctctgt gcacaccttc cccgccctgc tgcaatccgg cctgtacaca     540
```

```
atgtcttctt ctgtgacagt gcctagctct acatggccat ctcagacagt gacatgctct      600
gtggcccacc ccgcctctag cacaaccgtg gacaagaagc tggagccatc cggccctatt      660
tctacaatta acccttgccc tccttgcaaa gaatgccaca agtgccccgc cccaaacctg      720
gagggcggcc cttctgtgtt cattttccct cctaacatta aggacgtgct gatgatcagc      780
ctcaccccaa aggtgacatg cgtggtggtg gacgtgtccg aggacgaccc tgacgtgcag      840
atttcttggt tcgtgaacaa cgtggaggtg cacaccgccc agacccagac ccaccgggag      900
gactacaact ccaccattcg ggtggtgtct acactgccta ttcagcacca ggactggatg      960
agcggcaaag agttcaagtg caaggtgaac aacaaggacc tgccatctcc tattgagaga     1020
acaatttcta agattaaggg cctggtgcgc gcccctcagg tgtacattct gcctcctccc     1080
gccgagcagc tgagccggaa ggacgtgtcc ctcacatgcc tcgtggtggg cttcaaccct     1140
ggcgacatta gcgtggagtg gacatctaac ggccacacag aagaaaacta caaggacaca     1200
gcccctgtgc tcgactccga cggctcttac ttcatatact ctaagctgaa catgaaaaca     1260
tctaagtggg aaaagaccga ctctttctct tgcaacgtgc ggcacgaggg cctgaagaac     1320
tactacctca agaaaaccat tagcagaagt ccaggctaa                             1359
```

<210> SEQ ID NO 25
<211> LENGTH: 211
<212> TYPE: PRT
<213> ORGANISM: Artificial Sequence
<220> FEATURE:
<223> OTHER INFORMATION: B266-1 light chain

<400> SEQUENCE: 25

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Ile Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro Thr Phe
                85                  90                  95

Gly Ala Gly Thr Lys Leu Glu Leu Lys Ser Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
```

-continued

```
                      210

<210> SEQ ID NO 26
<211> LENGTH: 447
<212> TYPE: PRT
<213> ORGANISM: Artificial Sequence
<220> FEATURE:
<223> OTHER INFORMATION: B266-1 heavy chain

<400> SEQUENCE: 26

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Leu Gln Tyr Ser Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
```

|  |  | 355 |  |  |  | 360 |  |  |  | 365 |  |
|---|---|---|---|---|---|---|---|---|---|---|---|

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 27
<211> LENGTH: 633
<212> TYPE: DNA
<213> ORGANISM: Artificial Sequence
<220> FEATURE:
<223> OTHER INFORMATION: B266-1 light chain

<400> SEQUENCE: 27

```
cagatcgtgc tcacacagtc tccagccatc atgagcgcct ctcctggcga gaaggtgaca      60
atgacctgct ctgcctctag ccgcatttct tacatgtact ggtatcagca gaagccaggc     120
acctcccta  agaggtggat atacgacaca tccaagctgg cctccggcgt gcccgcccgg     180
ttcagcggct ctggcagcgg cacaagctac tccctgacaa ttagcacgat ggaggccgag     240
gacgccgcca catactactg ccaccagcgc tcgtcctacc caacattcgg cgccggcaca     300
aaattggaac tgaaggtggc tgcaccatct gtcttcatct tcccgccatc tgatgagcag     360
ttgaaatctg gaactgcctc tgttgtgtgc ctgctgaata acttctatcc cagagaggcc     420
aaagtacagt ggaaggtgga taacgccctc caatcgggta actcccagga gagtgtcaca     480
gagcaggaca gcaaggacag cacctacagc ctcagcagca ccctgacgct gagcaaagca     540
gactacgaga aacacaaagt ctacgcctgc gaagtcaccc atcagggcct gagctcgccc     600
gtcacaaaga gcttcaacag gggagagtgt tag                                  633
```

<210> SEQ ID NO 28
<211> LENGTH: 1337
<212> TYPE: DNA
<213> ORGANISM: Artificial Sequence
<220> FEATURE:
<223> OTHER INFORMATION: B266-1 heavy chain

<400> SEQUENCE: 28

```
gaggtgcagt acaacagtc  cggcgccgag ctagtgaagc aggcgccag  cgtgaagctg      60
tcttgcacag ccagcggctt caacattaag gacaccttca tgcactgggt gaagcagaga     120
cctgagcagg gcttagagtg gattggccgg atcgaccccg ccaacggcaa cacaaagtac     180
gacccaaagt tccagggcaa ggccacaatt accgccgaca tcttccaaac acagcctac      240
ctccagctgt cgtctctcac cagcgaggac accgccgtgt actactgcgc cctgctccag     300
tactccgcga tggactactg gggccagggc acatctgtga ccgtgtctag accaagggcc     360
catcggtctt ccccctggca ccctcctcca agagcacctc tgggggcaca gcggccctgg     420
gctgcctggt caaggactac ttccccgaac cggtgacggt gtcgtggaac tcaggcgccc     480
tgaccagcgg cgtgcacacc ttcccggctg tcctacagtc ctcaggactc tactccctca     540
gcagcgtggt gaccgtgccc tccagcagct tgggcaccca gacctacatc tgcaacgtga     600
```

| | |
|---|---|
| atcacaagcc cagcaacacc aaggtggaca agaaagttga gcccaaatct tgtgacaaaa | 660 |
| ctcacacatg cccaccgtgc ccagcacctg aactcctggg gggaccgtca gtcttcctct | 720 |
| ttcccccaaa acccaaggac accctcatga tctcccggac ccctgaggtc acatgcgtgg | 780 |
| tggtggacgt gagccacgaa gaccctgagg tcaagttcaa ctggtacgtg gacggcgtgg | 840 |
| aggtgcataa tgccaagaca aagccgcggg aggagcagta caacagcacg taccgtgtgg | 900 |
| tcagcgtcct caccgtcctg caccaggact ggctgaatgg caaggagtac aagtgcaagg | 960 |
| tctccaacaa agccctccca gcccccatcg agaaaaccat ctccaaagcc aagggcagc | 1020 |
| cccgagaacc acaggtgtac accctgcccc catcccggga ggagatgacc aagaaccagg | 1080 |
| tcagcctgac ctgcctggtc aaaggcttct atcccagcga catcgccgtg gagtgggaga | 1140 |
| gcaatgggca gccggagaac aactacaaga ccacgcctcc cgtgctggac tccgacggct | 1200 |
| ccttcttcct ctacagcaag ctcaccgtgg acaagagcag gtggcagcag gggaacgtct | 1260 |
| tctcatgctc cgtgatgcat gaggctctgc acaaccacta cacgcagaag agcctctccc | 1320 |
| tgtctccggg taaatga | 1337 |

<210> SEQ ID NO 29
<211> LENGTH: 315
<212> TYPE: DNA
<213> ORGANISM: Artificial Sequence
<220> FEATURE:
<223> OTHER INFORMATION: Trx1 gene

<400> SEQUENCE: 29

| | |
|---|---|
| atggtcaaac agatcgaatc aaaaaccgca tttcaagaag ccctggacgc cgctggtgac | 60 |
| aaactggtcg tggtggactt tagtgctacc tggtgcggcc cgtgtaaaat gattaaaccg | 120 |
| ttttccata gcctgtctga aaatacagt aacgttatct ttctggaagt ggatgttgat | 180 |
| gactgccagg acgtcgcgag cgaatgcgaa gtgaaatgta tgccgacgtt ccagtttttc | 240 |
| aaaaaaggtc aaaaagtcgg tgaatttagc ggtgccaaca agaaaaaact ggaagccacg | 300 |
| attaacgaac tggtg | 315 |

<210> SEQ ID NO 30
<211> LENGTH: 22
<212> TYPE: DNA
<213> ORGANISM: Artificial Sequence
<220> FEATURE:
<223> OTHER INFORMATION: hTrx1-For primer

<400> SEQUENCE: 30

| | |
|---|---|
| taatggtcaa acagatcgaa tc | 22 |

<210> SEQ ID NO 31
<211> LENGTH: 31
<212> TYPE: DNA
<213> ORGANISM: Artificial Sequence
<220> FEATURE:
<223> OTHER INFORMATION: hTrx1-Rev primer

<400> SEQUENCE: 31

| | |
|---|---|
| caccagttcg ttaatcgtgg taatgaaagc t | 31 |

<210> SEQ ID NO 32
<211> LENGTH: 7
<212> TYPE: PRT
<213> ORGANISM: Artificial Sequence
<220> FEATURE:
<223> OTHER INFORMATION: hTrx1 M1

<400> SEQUENCE: 32

Gln Ile Glu Gly Ser Thr Ala
1               5

<210> SEQ ID NO 33
<211> LENGTH: 6
<212> TYPE: PRT
<213> ORGANISM: Artificial Sequence
<220> FEATURE:
<223> OTHER INFORMATION: hTrx1 M2

<400> SEQUENCE: 33

Gln Glu Ala Leu Asp Ala
1               5

<210> SEQ ID NO 34
<211> LENGTH: 5
<212> TYPE: PRT
<213> ORGANISM: Artificial Sequence
<220> FEATURE:
<223> OTHER INFORMATION: hTrx1 M4

<400> SEQUENCE: 34

Tyr Ser Asn Val Ile
1               5

<210> SEQ ID NO 35
<211> LENGTH: 21
<212> TYPE: DNA
<213> ORGANISM: Artificial Sequence
<220> FEATURE:
<223> OTHER INFORMATION: hTrx1 M1

<400> SEQUENCE: 35
cagatcgaat caaaaaccgc a                                         21

<210> SEQ ID NO 36
<211> LENGTH: 18
<212> TYPE: DNA
<213> ORGANISM: Artificial Sequence
<220> FEATURE:
<223> OTHER INFORMATION: hTrx1 M2

<400> SEQUENCE: 36
caagaagccc tggacgcc                                             18

<210> SEQ ID NO 37
<211> LENGTH: 15
<212> TYPE: DNA
<213> ORGANISM: Artificial Sequence
<220> FEATURE:
<223> OTHER INFORMATION: hTrx1 M4

<400> SEQUENCE: 37
tacagtaacg ttatc                                                15

<210> SEQ ID NO 38
<211> LENGTH: 312
<212> TYPE: DNA
<213> ORGANISM: Artificial Sequence
<220> FEATURE:
<223> OTHER INFORMATION: TRX-N-His-M1

<400> SEQUENCE: 38
gtcaaagaga tcgaaggcaa agaagatttt caagaagccc tggacgccgc tggtgacaaa    60

```
ctggtcgtgg tggactttag tgctacctgg tgcggcccgt gtaaaatgat taaaccgttt    120
ttccatagcc tgtctgaaaa atacagtaac gttatctttc tggaagtgga tgttgatgac    180
tgccaggacg tcgcgagcga atgcgaagtg aaatgtatgc cgacgttcca gttttttcaaa   240 aaaggtcaaa aagtcggtga atttagcggt gccaacaaag aaaaactgga agccacgatt    300
aacgaactgg tg                                                        312

<210> SEQ ID NO 39
<211> LENGTH: 312
<212> TYPE: DNA
<213> ORGANISM: Artificial Sequence
<220> FEATURE:
<223> OTHER INFORMATION: TRX-N-His-M2

<400> SEQUENCE: 39
gtcaaacaga tcgaatcaaa aaccgcattt catgctgccc tgagcagtgc tggtgacaaa     60
ctggtcgtgg tggactttag tgctacctgg tgcggcccgt gtaaaatgat taaaccgttt    120
ttccatagcc tgtctgaaaa atacagtaac gttatctttc tggaagtgga tgttgatgac    180
tgccaggacg tcgcgagcga atgcgaagtg aaatgtatgc cgacgttcca gttttttcaaa   240 aaaggtcaaa aagtcggtga atttagcggt gccaacaaag aaaaactgga agccacgatt    300
aacgaactgg tg                                                        312

<210> SEQ ID NO 40
<211> LENGTH: 312
<212> TYPE: DNA
<213> ORGANISM: Artificial Sequence
<220> FEATURE:
<223> OTHER INFORMATION: TRX-N-His-M3

<400> SEQUENCE: 40
gtcaaacaga tcgaatcaaa aaccgcattt caagaagccc tggacgccgc tggtgacaaa     60
ctggtcgtgg tggactttag tgctacctgg tgcggcccgt gtaaaatgat taaaccgttt    120
tatcatagcc tgtctgaaaa atacagtaac gttatctttc tggaagtgga tgttgatgac    180
tgccaggacg tcgcgagcga atgcgaagtg aaatgtatgc cgacgttcca gttttttcaaa   240 aaaggtcaaa aagtcggtga atttagcggt gccaacaaag aaaaactgga agccacgatt    300
aacgaactgg tg                                                        312

<210> SEQ ID NO 41
<211> LENGTH: 312
<212> TYPE: DNA
<213> ORGANISM: Artificial Sequence
<220> FEATURE:
<223> OTHER INFORMATION: TRX-N-His-M4

<400> SEQUENCE: 41
gtcaaacaga tcgaatcaaa aaccgcattt caagaagccc tggacgccgc tggtgacaaa     60
ctggtcgtgg tggactttag tgctacctgg tgcggcccgt gtaaaatgat taaaccgttt    120
ttccatagcc tgtctgaaaa atttggcaac atggtgttcc tggaagtgga tgttgatgac    180
tgccaggacg tcgcgagcga atgcgaagtg aaatgtatgc cgacgttcca gttttttcaaa   240 aaaggtcaaa aagtcggtga atttagcggt gccaacaaag aaaaactgga agccacgatt    300
aacgaactgg tg                                                        312

<210> SEQ ID NO 42
```

<211> LENGTH: 312
<212> TYPE: DNA
<213> ORGANISM: Artificial Sequence
<220> FEATURE:
<223> OTHER INFORMATION: TRX-N-His-M5

<400> SEQUENCE: 42

| | | |
|---|---|---|
| gtcaaacaga tcgaatcaaa aaccgcattt caagaagccc tggacgccgc tggtgacaaa | 60 |
| ctggtcgtgg tggactttag tgctacctgg tgcggcccgt gtaaaatgat taaaccgttt | 120 |
| ttccatagcc tgtctgaaaa atacagtaac gttatctttc tggaagtgga tgttgatgac | 180 |
| tgccaggacg tcgcgagcga atgcgaagtg aaatgtatga taacgttcca gttttttcaaa | 240 |
| aaaggtcaaa aagtcggtga atttagcggt gccaacaaag aaaaactgga agccacgatt | 300 |
| aacgaactgg tg | 312 |

<210> SEQ ID NO 43
<211> LENGTH: 312
<212> TYPE: DNA
<213> ORGANISM: Artificial Sequence
<220> FEATURE:
<223> OTHER INFORMATION: TRX-N-His-M6

<400> SEQUENCE: 43

| | | |
|---|---|---|
| gtcaaacaga tcgaatcaaa aaccgcattt caagaagccc tggacgccgc tggtgacaaa | 60 |
| ctggtcgtgg tggactttag tgctacctgg tgcggcccgt gtaaaatgat taaaccgttt | 120 |
| ttccatagcc tgtctgaaaa atacagtaac gttatctttc tggaagtgga tgttgatgac | 180 |
| tgccaggacg tcgcgagcga atgcgaagtg aaatgtatgc cgacgttcca gttttataaa | 240 |
| aaaagggaaa aagtcggtga atttagcggt gccaacaaag aaaaactgga agccacgatt | 300 |
| aacgaactgg tg | 312 |

<210> SEQ ID NO 44
<211> LENGTH: 312
<212> TYPE: DNA
<213> ORGANISM: Artificial Sequence
<220> FEATURE:
<223> OTHER INFORMATION: TRX-N-His-M7

<400> SEQUENCE: 44

| | | |
|---|---|---|
| gtcaaacaga tcgaatcaaa aaccgcattt caagaagccc tggacgccgc tggtgacaaa | 60 |
| ctggtcgtgg tggactttag tgctacctgg tgcggcccgt gtaaaatgat taaaccgttt | 120 |
| ttccatagcc tgtctgaaaa atacagtaac gttatctttc tggaagtgga tgttgatgac | 180 |
| tgccaggacg tcgcgagcga atgcgaagtg aaatgtatgc cgacgttcca gttttttcaaa | 240 |
| aaaggtcaaa aagtcggtga atttagcggt gttaacaaag aaaaactgga agccacgatt | 300 |
| aacgaactgg tg | 312 |

<210> SEQ ID NO 45
<211> LENGTH: 312
<212> TYPE: DNA
<213> ORGANISM: Artificial Sequence
<220> FEATURE:
<223> OTHER INFORMATION: TRX-N-His-M8

<400> SEQUENCE: 45

| | | |
|---|---|---|
| gtcaaacaga tcgaatcaaa aaccgcattt caagaagccc tggacgccgc tggtgacaaa | 60 |
| ctggtcgtgg tggactttag tgctacctgg tgcggcccgt gtaaaatgat taaaccgttt | 120 |
| ttccatagcc tgtctgaaaa atacagtaac gttatctttc tggaagtgga tgttgatgac | 180 | tgccaggacg tcgcgagcga atgcgaagtg aaatgtatgc cgacgttcca gttttcaaa        240 aaaggtcaaa aagtcggtga atttagcggt gccaacaaag aaaaactgga agccatcatt        300 aacgaactgt gt                                                            312

<210> SEQ ID NO 46
<211> LENGTH: 19
<212> TYPE: DNA
<213> ORGANISM: Artificial Sequence
<220> FEATURE:
<223> OTHER INFORMATION: Vector-F primer

<400> SEQUENCE: 46
ggcgtgtacg gtgggaggt                                                     19

<210> SEQ ID NO 47
<211> LENGTH: 20
<212> TYPE: DNA
<213> ORGANISM: Artificial Sequence
<220> FEATURE:
<223> OTHER INFORMATION: Vector-R primer

<400> SEQUENCE: 47
agcagcgtat ccacatagcg                                                    20

<210> SEQ ID NO 48
<211> LENGTH: 57
<212> TYPE: DNA
<213> ORGANISM: Artificial Sequence
<220> FEATURE:
<223> OTHER INFORMATION: TRX M1-F primer

<400> SEQUENCE: 48
catcacgtca aagagatcga aggcaaagaa gattttcaag aagccctgga cgccgct           57

<210> SEQ ID NO 49
<211> LENGTH: 58
<212> TYPE: DNA
<213> ORGANISM: Artificial Sequence
<220> FEATURE:
<223> OTHER INFORMATION: TRX M1-R primer

<400> SEQUENCE: 49
ggcttcttga aaatcttctt tgccttcgat ctctttgacg tgatgatgat gatgatga          58

<210> SEQ ID NO 50
<211> LENGTH: 52
<212> TYPE: DNA
<213> ORGANISM: Artificial Sequence
<220> FEATURE:
<223> OTHER INFORMATION: TRX M2-F primer

<400> SEQUENCE: 50
aaaaccgcat ttcatgctgc cctgagcagt gctggtgaca aactggtcgt gg                52

<210> SEQ ID NO 51
<211> LENGTH: 54
<212> TYPE: DNA
<213> ORGANISM: Artificial Sequence
<220> FEATURE:
<223> OTHER INFORMATION: TRX M2-R primer

<400> SEQUENCE: 51
tttgtcacca gcactgctca gggcagcatg aaatgcggtt tttgattcga tctg              54

<210> SEQ ID NO 52
<211> LENGTH: 58
<212> TYPE: DNA
<213> ORGANISM: Artificial Sequence
<220> FEATURE:
<223> OTHER INFORMATION: TRX-M3-OV-F primer

<400> SEQUENCE: 52
attaaaccgt tttatcatag cctgtctgaa aaatacagta acgttatctt tctggaag        58

<210> SEQ ID NO 53
<211> LENGTH: 50
<212> TYPE: DNA
<213> ORGANISM: Artificial Sequence
<220> FEATURE:
<223> OTHER INFORMATION: TRX-M3-OV-R primer

<400> SEQUENCE: 53
agacaggcta tgataaaacg gtttaatcat tttacacggg ccgcaccagg                  50

<210> SEQ ID NO 54
<211> LENGTH: 65
<212> TYPE: DNA
<213> ORGANISM: Artificial Sequence
<220> FEATURE:
<223> OTHER INFORMATION: TRX-M4-OV-F primer

<400> SEQUENCE: 54
ctgtctgaaa aatttggcaa catggtgttc ctggaagtgg atgttgatga ctgccaggac       60
gtcgc                                                                   65

<210> SEQ ID NO 55
<211> LENGTH: 73
<212> TYPE: DNA
<213> ORGANISM: Artificial Sequence
<220> FEATURE:
<223> OTHER INFORMATION: TRX-M4-OV-R primer

<400> SEQUENCE: 55
atccacttcc aggaacacca tgttgccaaa tttttcagac aggctatgga aaaacggttt       60
aatcatttta cac                                                          73

<210> SEQ ID NO 56
<211> LENGTH: 55
<212> TYPE: DNA
<213> ORGANISM: Artificial Sequence
<220> FEATURE:
<223> OTHER INFORMATION: TRX-M5-OV-F primer

<400> SEQUENCE: 56
gtgaaatgta tgataacgtt ccagtttttc aaaaaaggtc aaaaagtcgg tgaat            55

<210> SEQ ID NO 57
<211> LENGTH: 49
<212> TYPE: DNA
<213> ORGANISM: Artificial Sequence
<220> FEATURE:
<223> OTHER INFORMATION: TRX-M5-OV-R primer

<400> SEQUENCE: 57
aaactggaac gttatcatac atttcacttc gcattcgctc gcgacgtcc                   49

<210> SEQ ID NO 58
<211> LENGTH: 65

<212> TYPE: DNA
<213> ORGANISM: Artificial Sequence
<220> FEATURE:
<223> OTHER INFORMATION: TRX-M6-OV-F primer

<400> SEQUENCE: 58
acgttccagt tttataaaaa aagggaaaaa gtcggtgaat ttagcggtgc aacaaagaa     60 aaact                                                                65

<210> SEQ ID NO 59
<211> LENGTH: 64
<212> TYPE: DNA
<213> ORGANISM: Artificial Sequence
<220> FEATURE:
<223> OTHER INFORMATION: TRX-M6-OV-R primer

<400> SEQUENCE: 59
ttcaccgact ttttcccttt ttttataaaa ctggaacgtc ggcatacatt tcacttcgca     60
ttcg                                                                 64

<210> SEQ ID NO 60
<211> LENGTH: 84
<212> TYPE: DNA
<213> ORGANISM: Artificial Sequence
<220> FEATURE:
<223> OTHER INFORMATION: TRX-M7-Xho-R primer

<400> SEQUENCE: 60
gaattctcga gctatcacac cagttcgtta atcgtggctt ccagttttc tttgttaaca      60 ccgctaaatt caccgacttt ttga                                            84

<210> SEQ ID NO 61
<211> LENGTH: 59
<212> TYPE: DNA
<213> ORGANISM: Artificial Sequence
<220> FEATURE:
<223> OTHER INFORMATION: TRX-M8-Xho-R primer

<400> SEQUENCE: 61
gaattctcga gctatcaaca cagttcgtta atgatggctt ccagttttc tttgttggc       59

<210> SEQ ID NO 62
<211> LENGTH: 19
<212> TYPE: DNA
<213> ORGANISM: Artificial Sequence
<220> FEATURE:
<223> OTHER INFORMATION: N293F-colo-F primer

<400> SEQUENCE: 62
ggcgtgtacg gtgggaggt                                                 19

<210> SEQ ID NO 63
<211> LENGTH: 20
<212> TYPE: DNA
<213> ORGANISM: Artificial Sequence
<220> FEATURE:
<223> OTHER INFORMATION: N293F-colo-R primer

<400> SEQUENCE: 63
agcagcgtat ccacatagcg                                                20

<210> SEQ ID NO 64
<211> LENGTH: 15
<212> TYPE: PRT

```
<213> ORGANISM: Artificial Sequence
<220> FEATURE:
<223> OTHER INFORMATION: Peptide_001

<400> SEQUENCE: 64

Val Ala Thr Ala Ala Asp Val His Ser Gln His His His His His
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Peptide_002

<400> SEQUENCE: 65

Ala Thr Ala Ala Asp Val His Ser Gln His His His His His His
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Peptide_003

<400> SEQUENCE: 66

Thr Ala Ala Asp Val His Ser Gln His His His His His His His
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Peptide_004

<400> SEQUENCE: 67

Ala Ala Asp Val His Ser Gln His His His His His His His His
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Peptide_005

<400> SEQUENCE: 68

Ala Asp Val His Ser Gln His His His His His His His His Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Peptide_006

<400> SEQUENCE: 69

Asp Val His Ser Gln His His His His His His His His Val Lys
1               5                   10                  15

<210> SEQ ID NO 70
<211> LENGTH: 15
<212> TYPE: PRT
<213> ORGANISM: Artificial Sequence
```

```
<220> FEATURE:
<223> OTHER INFORMATION: Peptide_007

<400> SEQUENCE: 70

Val His Ser Gln His His His His His His His Val Lys Gln
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Peptide_008

<400> SEQUENCE: 71

His Ser Gln His His His His His His His Val Lys Gln Ile
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Peptide_009

<400> SEQUENCE: 72

Ser Gln His His His His His His His Val Lys Gln Ile Glu
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Peptide_010

<400> SEQUENCE: 73

Gln His His His His His His His Val Lys Gln Ile Glu Ser
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Peptide_011

<400> SEQUENCE: 74

His His His His His His His Val Lys Gln Ile Glu Ser Lys
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Peptide_012

<400> SEQUENCE: 75

His His His His His His His Val Lys Gln Ile Glu Ser Lys Thr
1               5                   10                  15

<210> SEQ ID NO 76
<211> LENGTH: 15
<212> TYPE: PRT
<213> ORGANISM: Artificial Sequence
<220> FEATURE:
```

<223> OTHER INFORMATION: Peptide_013

<400> SEQUENCE: 76

His His His His His His Val Lys Gln Ile Glu Ser Lys Thr Ala
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Peptide_014

<400> SEQUENCE: 77

His His His His His Val Lys Gln Ile Glu Ser Lys Thr Ala Phe
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Peptide_015

<400> SEQUENCE: 78

His His His His Val Lys Gln Ile Glu Ser Lys Thr Ala Phe Gln
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Peptide_016

<400> SEQUENCE: 79

His His His Val Lys Gln Ile Glu Ser Lys Thr Ala Phe Gln Glu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Peptide_017

<400> SEQUENCE: 80

His His Val Lys Gln Ile Glu Ser Lys Thr Ala Phe Gln Glu Ala
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Peptide_018

<400> SEQUENCE: 81

His Val Lys Gln Ile Glu Ser Lys Thr Ala Phe Gln Glu Ala Leu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Peptide_019

```
<400> SEQUENCE: 82

Val Lys Gln Ile Glu Ser Lys Thr Ala Phe Gln Glu Ala Leu Asp
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Peptide_020

<400> SEQUENCE: 83

Lys Gln Ile Glu Ser Lys Thr Ala Phe Gln Glu Ala Leu Asp Ala
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Peptide_021

<400> SEQUENCE: 84

Gln Ile Glu Ser Lys Thr Ala Phe Gln Glu Ala Leu Asp Ala Ala
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Peptide_022

<400> SEQUENCE: 85

Ile Glu Ser Lys Thr Ala Phe Gln Glu Ala Leu Asp Ala Ala Gly
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Peptide_023

<400> SEQUENCE: 86

Glu Ser Lys Thr Ala Phe Gln Glu Ala Leu Asp Ala Ala Gly Asp
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Peptide_024

<400> SEQUENCE: 87

Ser Lys Thr Ala Phe Gln Glu Ala Leu Asp Ala Ala Gly Asp Lys
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Peptide_025
```

<400> SEQUENCE: 88

Lys Thr Ala Phe Gln Glu Ala Leu Asp Ala Ala Gly Asp Lys Leu
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Peptide_026

<400> SEQUENCE: 89

Thr Ala Phe Gln Glu Ala Leu Asp Ala Ala Gly Asp Lys Leu Val
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Peptide_027

<400> SEQUENCE: 90

Ala Phe Gln Glu Ala Leu Asp Ala Ala Gly Asp Lys Leu Val Val
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Peptide_028

<400> SEQUENCE: 91

Phe Gln Glu Ala Leu Asp Ala Ala Gly Asp Lys Leu Val Val Val
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Peptide_029

<400> SEQUENCE: 92

Gln Glu Ala Leu Asp Ala Ala Gly Asp Lys Leu Val Val Val Asp
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Peptide_030

<400> SEQUENCE: 93

Glu Ala Leu Asp Ala Ala Gly Asp Lys Leu Val Val Val Asp Phe
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Peptide_031

<400> SEQUENCE: 94

Ala Leu Asp Ala Ala Gly Asp Lys Leu Val Val Val Asp Phe Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Peptide_032

<400> SEQUENCE: 95

Leu Asp Ala Ala Gly Asp Lys Leu Val Val Val Asp Phe Ser Ala
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Peptide_033

<400> SEQUENCE: 96

Asp Ala Ala Gly Asp Lys Leu Val Val Val Asp Phe Ser Ala Thr
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Peptide_034

<400> SEQUENCE: 97

Ala Ala Gly Asp Lys Leu Val Val Val Asp Phe Ser Ala Thr Trp
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Peptide_035

<400> SEQUENCE: 98

Ala Gly Asp Lys Leu Val Val Val Asp Phe Ser Ala Thr Trp Cys
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Peptide_036

<400> SEQUENCE: 99

Gly Asp Lys Leu Val Val Val Asp Phe Ser Ala Thr Trp Cys Gly
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Peptide_037

<400> SEQUENCE: 100

```
Asp Lys Leu Val Val Asp Phe Ser Ala Thr Trp Cys Gly Pro
1               5                   10                  15
```

<210> SEQ ID NO 101
<211> LENGTH: 15
<212> TYPE: PRT
<213> ORGANISM: Artificial Sequence
<220> FEATURE:
<223> OTHER INFORMATION: Peptide_038

<400> SEQUENCE: 101

```
Lys Leu Val Val Val Asp Phe Ser Ala Thr Trp Cys Gly Pro Cys
1               5                   10                  15
```

<210> SEQ ID NO 102
<211> LENGTH: 15
<212> TYPE: PRT
<213> ORGANISM: Artificial Sequence
<220> FEATURE:
<223> OTHER INFORMATION: Peptide_039

<400> SEQUENCE: 102

```
Leu Val Val Val Asp Phe Ser Ala Thr Trp Cys Gly Pro Cys Lys
1               5                   10                  15
```

<210> SEQ ID NO 103
<211> LENGTH: 15
<212> TYPE: PRT
<213> ORGANISM: Artificial Sequence
<220> FEATURE:
<223> OTHER INFORMATION: Peptide_040

<400> SEQUENCE: 103

```
Val Val Val Asp Phe Ser Ala Thr Trp Cys Gly Pro Cys Lys Met
1               5                   10                  15
```

<210> SEQ ID NO 104
<211> LENGTH: 15
<212> TYPE: PRT
<213> ORGANISM: Artificial Sequence
<220> FEATURE:
<223> OTHER INFORMATION: Peptide_041

<400> SEQUENCE: 104

```
Val Val Asp Phe Ser Ala Thr Trp Cys Gly Pro Cys Lys Met Ile
1               5                   10                  15
```

<210> SEQ ID NO 105
<211> LENGTH: 15
<212> TYPE: PRT
<213> ORGANISM: Artificial Sequence
<220> FEATURE:
<223> OTHER INFORMATION: Peptide_042

<400> SEQUENCE: 105

```
Val Asp Phe Ser Ala Thr Trp Cys Gly Pro Cys Lys Met Ile Lys
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Peptide_043

<400> SEQUENCE: 106

```
Asp Phe Ser Ala Thr Trp Cys Gly Pro Cys Lys Met Ile Lys Pro
```

```
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Peptide_044

<400> SEQUENCE: 107

Phe Ser Ala Thr Trp Cys Gly Pro Cys Lys Met Ile Lys Pro Phe
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Peptide_045

<400> SEQUENCE: 108

Ser Ala Thr Trp Cys Gly Pro Cys Lys Met Ile Lys Pro Phe Phe
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Peptide_046

<400> SEQUENCE: 109

Ala Thr Trp Cys Gly Pro Cys Lys Met Ile Lys Pro Phe Phe His
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Peptide_047

<400> SEQUENCE: 110

Thr Trp Cys Gly Pro Cys Lys Met Ile Lys Pro Phe Phe His Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Peptide_048

<400> SEQUENCE: 111

Trp Cys Gly Pro Cys Lys Met Ile Lys Pro Phe Phe His Ser Leu
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Peptide_049

<400> SEQUENCE: 112

Cys Gly Pro Cys Lys Met Ile Lys Pro Phe Phe His Ser Leu Ser
1               5                   10                  15
```

```
<210> SEQ ID NO 113
<211> LENGTH: 15
<212> TYPE: PRT
<213> ORGANISM: Artificial Sequence
<220> FEATURE:
<223> OTHER INFORMATION: Peptide_050

<400> SEQUENCE: 113

Gly Pro Cys Lys Met Ile Lys Pro Phe Phe His Ser Leu Ser Glu
1               5                  10                  15

<210> SEQ ID NO 114
<211> LENGTH: 15
<212> TYPE: PRT
<213> ORGANISM: Artificial Sequence
<220> FEATURE:
<223> OTHER INFORMATION: Peptide_051

<400> SEQUENCE: 114

Pro Cys Lys Met Ile Lys Pro Phe Phe His Ser Leu Ser Glu Lys
1               5                  10                  15

<210> SEQ ID NO 115
<211> LENGTH: 15
<212> TYPE: PRT
<213> ORGANISM: Artificial Sequence
<220> FEATURE:
<223> OTHER INFORMATION: Peptide_052

<400> SEQUENCE: 115

Cys Lys Met Ile Lys Pro Phe Phe His Ser Leu Ser Glu Lys Tyr
1               5                  10                  15

<210> SEQ ID NO 116
<211> LENGTH: 15
<212> TYPE: PRT
<213> ORGANISM: Artificial Sequence
<220> FEATURE:
<223> OTHER INFORMATION: Peptide_053

<400> SEQUENCE: 116

Lys Met Ile Lys Pro Phe Phe His Ser Leu Ser Glu Lys Tyr Ser
1               5                  10                  15

<210> SEQ ID NO 117
<211> LENGTH: 15
<212> TYPE: PRT
<213> ORGANISM: Artificial Sequence
<220> FEATURE:
<223> OTHER INFORMATION: Peptide_054

<400> SEQUENCE: 117

Met Ile Lys Pro Phe Phe His Ser Leu Ser Glu Lys Tyr Ser Asn
1               5                  10                  15

<210> SEQ ID NO 118
<211> LENGTH: 15
<212> TYPE: PRT
<213> ORGANISM: Artificial Sequence
<220> FEATURE:
<223> OTHER INFORMATION: Peptide_055

<400> SEQUENCE: 118

Ile Lys Pro Phe Phe His Ser Leu Ser Glu Lys Tyr Ser Asn Val
1               5                  10                  15
```

<210> SEQ ID NO 119
<211> LENGTH: 15
<212> TYPE: PRT
<213> ORGANISM: Artificial Sequence
<220> FEATURE:
<223> OTHER INFORMATION: Peptide_056

<400> SEQUENCE: 119

```
Lys Pro Phe Phe His Ser Leu Ser Glu Lys Tyr Ser Asn Val Ile
1               5                   10                  15
```

<210> SEQ ID NO 120
<211> LENGTH: 15
<212> TYPE: PRT
<213> ORGANISM: Artificial Sequence
<220> FEATURE:
<223> OTHER INFORMATION: Peptide_057

<400> SEQUENCE: 120

```
Pro Phe Phe His Ser Leu Ser Glu Lys Tyr Ser Asn Val Ile Phe
1               5                   10                  15
```

<210> SEQ ID NO 121
<211> LENGTH: 15
<212> TYPE: PRT
<213> ORGANISM: Artificial Sequence
<220> FEATURE:
<223> OTHER INFORMATION: Peptide_058

<400> SEQUENCE: 121

```
Phe Phe His Ser Leu Ser Glu Lys Tyr Ser Asn Val Ile Phe Leu
1               5                   10                  15
```

<210> SEQ ID NO 122
<211> LENGTH: 15
<212> TYPE: PRT
<213> ORGANISM: Artificial Sequence
<220> FEATURE:
<223> OTHER INFORMATION: Peptide_059

<400> SEQUENCE: 122

```
Phe His Ser Leu Ser Glu Lys Tyr Ser Asn Val Ile Phe Leu Glu
1               5                   10                  15
```

<210> SEQ ID NO 123
<211> LENGTH: 15
<212> TYPE: PRT
<213> ORGANISM: Artificial Sequence
<220> FEATURE:
<223> OTHER INFORMATION: Peptide_060

<400> SEQUENCE: 123

```
His Ser Leu Ser Glu Lys Tyr Ser Asn Val Ile Phe Leu Glu Val
1               5                   10                  15
```

<210> SEQ ID NO 124
<211> LENGTH: 15
<212> TYPE: PRT
<213> ORGANISM: Artificial Sequence
<220> FEATURE:
<223> OTHER INFORMATION: Peptide_061

<400> SEQUENCE: 124

```
Ser Leu Ser Glu Lys Tyr Ser Asn Val Ile Phe Leu Glu Val Asp
1               5                   10                  15
```

```
<210> SEQ ID NO 125
<211> LENGTH: 15
<212> TYPE: PRT
<213> ORGANISM: Artificial Sequence
<220> FEATURE:
<223> OTHER INFORMATION: Peptide_062

<400> SEQUENCE: 125

Leu Ser Glu Lys Tyr Ser Asn Val Ile Phe Leu Glu Val Asp Val
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Peptide_063

<400> SEQUENCE: 126

Ser Glu Lys Tyr Ser Asn Val Ile Phe Leu Glu Val Asp Val Asp
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Peptide_064

<400> SEQUENCE: 127

Glu Lys Tyr Ser Asn Val Ile Phe Leu Glu Val Asp Val Asp Asp
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Peptide_065

<400> SEQUENCE: 128

Lys Tyr Ser Asn Val Ile Phe Leu Glu Val Asp Val Asp Asp Cys
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Peptide_066

<400> SEQUENCE: 129

Tyr Ser Asn Val Ile Phe Leu Glu Val Asp Val Asp Asp Cys Gln
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Peptide_067

<400> SEQUENCE: 130

Ser Asn Val Ile Phe Leu Glu Val Asp Val Asp Asp Cys Gln Asp
1               5                   10                  15

<210> SEQ ID NO 131
```

<211> LENGTH: 15
<212> TYPE: PRT
<213> ORGANISM: Artificial Sequence
<220> FEATURE:
<223> OTHER INFORMATION: Peptide_068

<400> SEQUENCE: 131

Asn Val Ile Phe Leu Glu Val Asp Val Asp Asp Cys Gln Asp Val
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Peptide_069

<400> SEQUENCE: 132

Val Ile Phe Leu Glu Val Asp Val Asp Asp Cys Gln Asp Val Ala
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Peptide_070

<400> SEQUENCE: 133

Ile Phe Leu Glu Val Asp Val Asp Asp Cys Gln Asp Val Ala Ser
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Peptide_071

<400> SEQUENCE: 134

Phe Leu Glu Val Asp Val Asp Asp Cys Gln Asp Val Ala Ser Glu
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Peptide_072

<400> SEQUENCE: 135

Leu Glu Val Asp Val Asp Asp Cys Gln Asp Val Ala Ser Glu Cys
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Peptide_073

<400> SEQUENCE: 136

Glu Val Asp Val Asp Asp Cys Gln Asp Val Ala Ser Glu Cys Glu
1               5                   10                  15

<210> SEQ ID NO 137
<211> LENGTH: 15

```
<212> TYPE: PRT
<213> ORGANISM: Artificial Sequence
<220> FEATURE:
<223> OTHER INFORMATION: Peptide_074

<400> SEQUENCE: 137

Val Asp Val Asp Cys Gln Asp Val Ala Ser Glu Cys Glu Val
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Peptide_075

<400> SEQUENCE: 138

Asp Val Asp Asp Cys Gln Asp Val Ala Ser Glu Cys Glu Val Lys
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Peptide_076

<400> SEQUENCE: 139

Val Asp Asp Cys Gln Asp Val Ala Ser Glu Cys Glu Val Lys Cys
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Peptide_077

<400> SEQUENCE: 140

Asp Asp Cys Gln Asp Val Ala Ser Glu Cys Glu Val Lys Cys Met
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Peptide_078

<400> SEQUENCE: 141

Asp Cys Gln Asp Val Ala Ser Glu Cys Glu Val Lys Cys Met Pro
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Peptide_079

<400> SEQUENCE: 142

Cys Gln Asp Val Ala Ser Glu Cys Glu Val Lys Cys Met Pro Thr
1               5                   10                  15

<210> SEQ ID NO 143
<211> LENGTH: 15
<212> TYPE: PRT
```

```
<213> ORGANISM: Artificial Sequence
<220> FEATURE:
<223> OTHER INFORMATION: Peptide_080

<400> SEQUENCE: 143

Gln Asp Val Ala Ser Glu Cys Glu Val Lys Cys Met Pro Thr Phe
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Peptide_081

<400> SEQUENCE: 144

Asp Val Ala Ser Glu Cys Glu Val Lys Cys Met Pro Thr Phe Gln
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Peptide_082

<400> SEQUENCE: 145

Val Ala Ser Glu Cys Glu Val Lys Cys Met Pro Thr Phe Gln Phe
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Peptide_083

<400> SEQUENCE: 146

Ala Ser Glu Cys Glu Val Lys Cys Met Pro Thr Phe Gln Phe Phe
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Peptide_084

<400> SEQUENCE: 147

Ser Glu Cys Glu Val Lys Cys Met Pro Thr Phe Gln Phe Phe Lys
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Peptide_085

<400> SEQUENCE: 148

Glu Cys Glu Val Lys Cys Met Pro Thr Phe Gln Phe Phe Lys Lys
1               5                   10                  15

<210> SEQ ID NO 149
<211> LENGTH: 15
<212> TYPE: PRT
<213> ORGANISM: Artificial Sequence
```

```
<220> FEATURE:
<223> OTHER INFORMATION: Peptide_086

<400> SEQUENCE: 149

Cys Glu Val Lys Cys Met Pro Thr Phe Gln Phe Phe Lys Lys Gly
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Peptide_087

<400> SEQUENCE: 150

Glu Val Lys Cys Met Pro Thr Phe Gln Phe Phe Lys Lys Gly Gln
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Peptide_088

<400> SEQUENCE: 151

Val Lys Cys Met Pro Thr Phe Gln Phe Phe Lys Lys Gly Gln Lys
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Peptide_089

<400> SEQUENCE: 152

Lys Cys Met Pro Thr Phe Gln Phe Phe Lys Lys Gly Gln Lys Val
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Peptide_090

<400> SEQUENCE: 153

Cys Met Pro Thr Phe Gln Phe Phe Lys Lys Gly Gln Lys Val Gly
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Peptide_091

<400> SEQUENCE: 154

Met Pro Thr Phe Gln Phe Phe Lys Lys Gly Gln Lys Val Gly Glu
1               5                   10                  15

<210> SEQ ID NO 155
<211> LENGTH: 15
<212> TYPE: PRT
<213> ORGANISM: Artificial Sequence
<220> FEATURE:
```

-continued

<223> OTHER INFORMATION: Peptide_092

<400> SEQUENCE: 155

Pro Thr Phe Gln Phe Phe Lys Lys Gly Gln Lys Val Gly Glu Phe
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Peptide_093

<400> SEQUENCE: 156

Thr Phe Gln Phe Phe Lys Lys Gly Gln Lys Val Gly Glu Phe Ser
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Peptide_094

<400> SEQUENCE: 157

Phe Gln Phe Phe Lys Lys Gly Gln Lys Val Gly Glu Phe Ser Gly
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Peptide_095

<400> SEQUENCE: 158

Gln Phe Phe Lys Lys Gly Gln Lys Val Gly Glu Phe Ser Gly Ala
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Peptide_096

<400> SEQUENCE: 159

Phe Phe Lys Lys Gly Gln Lys Val Gly Glu Phe Ser Gly Ala Asn
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Peptide_097

<400> SEQUENCE: 160

Phe Lys Lys Gly Gln Lys Val Gly Glu Phe Ser Gly Ala Asn Lys
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Peptide_098

```
<400> SEQUENCE: 161

Lys Lys Gly Gln Lys Val Gly Glu Phe Ser Gly Ala Asn Lys Glu
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Peptide_099

<400> SEQUENCE: 162

Lys Gly Gln Lys Val Gly Glu Phe Ser Gly Ala Asn Lys Glu Lys
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Peptide_100

<400> SEQUENCE: 163

Gly Gln Lys Val Gly Glu Phe Ser Gly Ala Asn Lys Glu Lys Leu
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Peptide_101

<400> SEQUENCE: 164

Gln Lys Val Gly Glu Phe Ser Gly Ala Asn Lys Glu Lys Leu Glu
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Peptide_102

<400> SEQUENCE: 165

Lys Val Gly Glu Phe Ser Gly Ala Asn Lys Glu Lys Leu Glu Ala
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Peptide_103

<400> SEQUENCE: 166

Val Gly Glu Phe Ser Gly Ala Asn Lys Glu Lys Leu Glu Ala Thr
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Peptide_104
```

<400> SEQUENCE: 167

Gly Glu Phe Ser Gly Ala Asn Lys Glu Lys Leu Glu Ala Thr Ile
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Peptide_105

<400> SEQUENCE: 168

Glu Phe Ser Gly Ala Asn Lys Glu Lys Leu Glu Ala Thr Ile Asn
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Peptide_106

<400> SEQUENCE: 169

Phe Ser Gly Ala Asn Lys Glu Lys Leu Glu Ala Thr Ile Asn Glu
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Peptide_107

<400> SEQUENCE: 170

Ser Gly Ala Asn Lys Glu Lys Leu Glu Ala Thr Ile Asn Glu Leu
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Peptide_108

<400> SEQUENCE: 171

Gly Ala Asn Lys Glu Lys Leu Glu Ala Thr Ile Asn Glu Leu Val
1               5                   10                  15

<210> SEQ ID NO 172
<211> LENGTH: 26
<212> TYPE: PRT
<213> ORGANISM: Artificial Sequence
<220> FEATURE:
<223> OTHER INFORMATION: B264 and B266-1 epitope

<400> SEQUENCE: 172

Ala Thr Trp Cys Gly Pro Cys Lys Met Ile Lys Pro Phe Phe His Ser
1               5                   10                  15

Leu Ser Glu Lys Tyr Ser Asn Val Ile Phe
            20                  25

<210> SEQ ID NO 173
<211> LENGTH: 15
<212> TYPE: PRT
<213> ORGANISM: Artificial Sequence
<220> FEATURE:

<223> OTHER INFORMATION: B266-1 epitope

<400> SEQUENCE: 173

Pro Thr Phe Gln Phe Phe Lys Lys Gly Gln Lys Val Gly Glu Phe
1               5                   10                  15

<210> SEQ ID NO 174
<211> LENGTH: 21
<212> TYPE: PRT
<213> ORGANISM: Artificial Sequence
<220> FEATURE:
<223> OTHER INFORMATION: B264 epitope

<400> SEQUENCE: 174

Val Lys Gln Ile Glu Ser Lys Thr Ala Phe Gln Glu Ala Leu Asp Ala
1               5                   10                  15

Ala Gly Asp Lys Leu
            20

<210> SEQ ID NO 175
<211> LENGTH: 17
<212> TYPE: PRT
<213> ORGANISM: Artificial Sequence
<220> FEATURE:
<223> OTHER INFORMATION: B264 epitope

<400> SEQUENCE: 175

Ser Glu Cys Glu Val Lys Cys Met Pro Thr Phe Gln Phe Phe Lys Lys
1               5                   10                  15

Gly

<210> SEQ ID NO 176
<211> LENGTH: 20
<212> TYPE: PRT
<213> ORGANISM: Artificial Sequence
<220> FEATURE:
<223> OTHER INFORMATION: B264 epitope

<400> SEQUENCE: 176

Pro Thr Phe Gln Phe Phe Lys Lys Gly Gln Lys Val Gly Glu Phe Ser
1               5                   10                  15

Gly Ala Asn Lys
            20

<210> SEQ ID NO 177
<211> LENGTH: 78
<212> TYPE: DNA
<213> ORGANISM: Artificial Sequence
<220> FEATURE:
<223> OTHER INFORMATION: B264 and B266-1 epitope

<400> SEQUENCE: 177
gctacctggt gcggcccgtg taaaatgatt aaaccgtttt tccatagcct gtctgaaaaa    60
tacagtaacg ttatcttt                                                  78

<210> SEQ ID NO 178
<211> LENGTH: 45
<212> TYPE: DNA
<213> ORGANISM: Artificial Sequence
<220> FEATURE:
<223> OTHER INFORMATION: B266-1 epitope

<400> SEQUENCE: 178
ccgacgttcc agttttttcaa aaaaggtcaa aaagtcggtg aattt                   45

```
<210> SEQ ID NO 179
<211> LENGTH: 63
<212> TYPE: DNA
<213> ORGANISM: Artificial Sequence
<220> FEATURE:
<223> OTHER INFORMATION: B264 epitope

<400> SEQUENCE: 179
gtcaaacaga tcgaatcaaa aaccgcattt caagaagccc tggacgccgc tggtgacaaa      60
ctg                                                                   63

<210> SEQ ID NO 180
<211> LENGTH: 51
<212> TYPE: DNA
<213> ORGANISM: Artificial Sequence
<220> FEATURE:
<223> OTHER INFORMATION: B264 epitope

<400> SEQUENCE: 180
agcgaatgcg aagtgaaatg tatgccgacg ttccagtttt tcaaaaaagg t               51

<210> SEQ ID NO 181
<211> LENGTH: 60
<212> TYPE: DNA
<213> ORGANISM: Artificial Sequence
<220> FEATURE:
<223> OTHER INFORMATION: B264 epitope

<400> SEQUENCE: 181
ccgacgttcc agttttttcaa aaaaggtcaa aaagtcggtg aatttagcgg tgccaacaaa     60

<210> SEQ ID NO 182
<211> LENGTH: 14
<212> TYPE: PRT
<213> ORGANISM: Artificial Sequence
<220> FEATURE:
<223> OTHER INFORMATION: TRX1-M1 mutant protein

<400> SEQUENCE: 182

Gln Ile Glu Ser Lys Thr Ala Glu Ile Glu Gly Lys Glu Asp
1               5                   10

<210> SEQ ID NO 183
<211> LENGTH: 12
<212> TYPE: PRT
<213> ORGANISM: Artificial Sequence
<220> FEATURE:
<223> OTHER INFORMATION: M2 mutant protein

<400> SEQUENCE: 183

Gln Glu Ala Leu Asp Ala His Ala Ala Leu Ser Ser
1               5                   10

<210> SEQ ID NO 184
<211> LENGTH: 10
<212> TYPE: PRT
<213> ORGANISM: Artificial Sequence
<220> FEATURE:
<223> OTHER INFORMATION: M4 mutant protein

<400> SEQUENCE: 184

Tyr Ser Asn Val Ile Phe Gly Asn Met Val
1               5                   10
```

```
<210> SEQ ID NO 185
<211> LENGTH: 11
<212> TYPE: DNA
<213> ORGANISM: Artificial Sequence
<220> FEATURE:
<223> OTHER INFORMATION: BamH1 Restriction Site

<400> SEQUENCE: 185
cctaggctat a                                                          11

<210> SEQ ID NO 186
<211> LENGTH: 212
<212> TYPE: PRT
<213> ORGANISM: Artificial Sequence
<220> FEATURE:
<223> OTHER INFORMATION: light chain of antibody 9G7

<400> SEQUENCE: 186
```

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Leu Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro Thr Phe
                85                  90                  95

Gly Ala Gly Thr Lys Leu Glu Ile Lys Arg Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

```
<210> SEQ ID NO 187
<211> LENGTH: 452
<212> TYPE: PRT
<213> ORGANISM: Artificial Sequence
<220> FEATURE:
<223> OTHER INFORMATION: heavy chain of antibody 9GF

<400> SEQUENCE: 187
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

-continued

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Leu Gln Tyr Ser Ala Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Val His Thr Phe Pro Ala Leu Leu Gln Ser
                165                 170                 175

Gly Leu Tyr Thr Met Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
            340                 345                 350

Gln Val Tyr Ile Leu Pro Pro Ala Glu Gln Leu Ser Arg Lys Asp
        355                 360                 365

Val Ser Leu Thr Cys Leu Val Val Gly Phe Asn Pro Gly Asp Ile Ser
    370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu
                405                 410                 415

Asn Met Lys Thr Ser Lys Trp Glu Lys Thr Asp Ser Phe Ser Cys Asn
            420                 425                 430

Val Arg His Glu Gly Leu Lys Asn Tyr Tyr Leu Lys Lys Thr Ile Ser
        435                 440                 445

Arg Ser Pro Gly

<210> SEQ ID NO 188
<211> LENGTH: 219
<212> TYPE: PRT
<213> ORGANISM: Artificial Sequence
<220> FEATURE:
<223> OTHER INFORMATION: light chain of antibody 2B4

<400> SEQUENCE: 188

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Leu Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 189
<211> LENGTH: 442
<212> TYPE: PRT
<213> ORGANISM: Artificial Sequence
<220> FEATURE:
<223> OTHER INFORMATION: heavy chain of antibody 2B4

<400> SEQUENCE: 189

```
Gln Val Gln Leu Gln Gln Ser Phe Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Thr Ser Asp Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80
```

```
Met Gln Leu Ser Ser Leu Thr Ser Glu Asp Ser Ala Val Tyr Phe Cys
                 85                  90                  95

Ala Ser Glu Gly Gly Phe Leu Tyr Tyr Phe Asp Tyr Trp Gly Gln Gly
            100                 105                 110

Thr Thr Leu Thr Val Ser Ser Ala Lys Thr Thr Pro Pro Ser Val Tyr
            115                 120                 125

Pro Leu Ala Pro Gly Ser Ala Ala Gln Thr Asn Ser Asn Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
                180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
            210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly
            435                 440

<210> SEQ ID NO 190
<211> LENGTH: 112
<212> TYPE: PRT
<213> ORGANISM: Artificial Sequence
<220> FEATURE:
<223> OTHER INFORMATION: light chain of antibody B266-1

<400> SEQUENCE: 190
```

```
Asp Val Leu Lys Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 191
<211> LENGTH: 100
<212> TYPE: PRT
<213> ORGANISM: Artificial Sequence
<220> FEATURE:
<223> OTHER INFORMATION: Mus musculus IGKV1-117*01

<400> SEQUENCE: 191

```
Asp Val Leu Lys Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
            100
```

<210> SEQ ID NO 192
<211> LENGTH: 12
<212> TYPE: PRT
<213> ORGANISM: Artificial Sequence
<220> FEATURE:
<223> OTHER INFORMATION: Mus musculus

<400> SEQUENCE: 192

```
Tyr Thr Phe Gly Gly Gly Thr Lys Leu Glu Ile Lys
1               5                   10
```

<210> SEQ ID NO 193
<211> LENGTH: 119
<212> TYPE: PRT
<213> ORGANISM: Artificial Sequence
<220> FEATURE:
<223> OTHER INFORMATION: heavy chain of antibody B266-1

<400> SEQUENCE: 193

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
```

```
            20                  25                  30

Thr Met His Trp Val Lys Gln Arg Pro Gly Gln Gly Leu Glu Trp Ile
        35                  40                  45

Gly Tyr Ile Asn Pro Thr Ser Asp Tyr Thr Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Glu Gly Gly Phe Leu Tyr Tyr Phe Asp Tyr Trp Gly Gln Gly
            100                 105                 110

Thr Thr Leu Thr Val Ser Ser
        115

<210> SEQ ID NO 194
<211> LENGTH: 98
<212> TYPE: PRT
<213> ORGANISM: Artificial Sequence
<220> FEATURE:
<223> OTHER INFORMATION: IGHV1-4*01 Mus musculus

<400> SEQUENCE: 194

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 195
<211> LENGTH: 15
<212> TYPE: PRT
<213> ORGANISM: Artificial Sequence
<220> FEATURE:
<223> OTHER INFORMATION: IGHJ2*01 Mus musculus

<400> SEQUENCE: 195

Tyr Phe Asp Tyr Trp Gly Gln Gly Thr Thr Leu Thr Val Ser Ser
1               5                   10                  15

<210> SEQ ID NO 196
<211> LENGTH: 105
<212> TYPE: PRT
<213> ORGANISM: Artificial Sequence
<220> FEATURE:
<223> OTHER INFORMATION: light chain of antibody B264

<400> SEQUENCE: 196

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Ile Ser Tyr Met
            20                  25                  30
```

Tyr Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro Thr Phe
                85                  90                  95

Gly Ala Gly Thr Lys Leu Glu Leu Lys
            100                 105

<210> SEQ ID NO 197
<211> LENGTH: 94
<212> TYPE: PRT
<213> ORGANISM: Artificial Sequence
<220> FEATURE:
<223> OTHER INFORMATION: IGKV4-70*01 Mus musculus

<400> SEQUENCE: 197

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

Met Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro
                85                  90

<210> SEQ ID NO 198
<211> LENGTH: 12
<212> TYPE: PRT
<213> ORGANISM: Artificial Sequence
<220> FEATURE:
<223> OTHER INFORMATION: IGKJ5*01 Mus musculus

<400> SEQUENCE: 198

Leu Thr Phe Gly Ala Gly Thr Lys Leu Glu Leu Lys
1               5                   10

<210> SEQ ID NO 199
<211> LENGTH: 116
<212> TYPE: PRT
<213> ORGANISM: Artificial Sequence
<220> FEATURE:
<223> OTHER INFORMATION: heavy chain of antibody B264

<400> SEQUENCE: 199

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr

```
                65                  70                  75                  80
Leu Gln Leu Ser Ser Leu Thr Ser Glu Asp Thr Ala Val Tyr Tyr Cys
                    85                  90                  95

Ala Leu Leu Gln Tyr Ser Ala Met Asp Tyr Trp Gly Gln Gly Thr Ser
                100                 105                 110

Val Thr Val Ser
        115

<210> SEQ ID NO 200
<211> LENGTH: 98
<212> TYPE: PRT
<213> ORGANISM: Artificial Sequence
<220> FEATURE:
<223> OTHER INFORMATION: IGHV14-3*02 Mus musculus

<400> SEQUENCE: 200

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg

<210> SEQ ID NO 201
<211> LENGTH: 16
<212> TYPE: PRT
<213> ORGANISM: Artificial Sequence
<220> FEATURE:
<223> OTHER INFORMATION: IGHJ4*01 Mus musculus

<400> SEQUENCE: 201

Tyr Tyr Ala Met Asp Tyr Trp Gly Gln Gly Thr Ser Val Thr Val Ser
1               5                   10                  15

<210> SEQ ID NO 202
<211> LENGTH: 103
<212> TYPE: PRT
<213> ORGANISM: Artificial Sequence
<220> FEATURE:
<223> OTHER INFORMATION: Human TRX1

<400> SEQUENCE: 202

Val Lys Gln Ile Glu Ser Lys Thr Ala Phe Gln Glu Ala Leu Asp Ala
1               5                   10                  15

Ala Gly Asp Lys Leu Val Val Val Asp Phe Ser Ala Thr Trp Cys Gly
            20                  25                  30

Pro Cys Lys Met Ile Lys Pro Phe Phe His Ser Leu Ser Glu Lys Tyr
        35                  40                  45

Ser Asn Val Ile Phe Leu Glu Val Asp Val Asp Asp Cys Gln Asp Val
    50                  55                  60

Ala Ser Glu Cys Glu Val Lys Cys Met Pro Thr Phe Gln Phe Phe Lys
65                  70                  75                  80
```

Lys Gly Gln Lys Val Gly Glu Phe Ser Gly Ala Asn Lys Glu Lys Leu
                85                  90                  95

Glu Ala Thr Ile Asn Glu Leu
            100

<210> SEQ ID NO 203
<211> LENGTH: 103
<212> TYPE: PRT
<213> ORGANISM: Artificial Sequence
<220> FEATURE:
<223> OTHER INFORMATION: Chrysochloris asiatica TRX1

<400> SEQUENCE: 203

Val Lys Glu Ile Glu Gly Lys Glu Asp Phe His Ala Ala Leu Ser Ser
1               5                   10                  15

Ala Gly Asp Lys Leu Val Val Val Asp Phe Ser Ala Thr Trp Cys Gly
            20                  25                  30

Pro Cys Lys Met Ile Lys Pro Phe Tyr His Ser Leu Ser Glu Lys Phe
        35                  40                  45

Gly Asn Met Val Phe Leu Glu Val Asp Val Asp Cys Gln Asp Val
    50                  55                  60

Ala Ser Glu Cys Glu Val Lys Cys Met Ile Thr Phe Gln Phe Tyr Lys
65                  70                  75                  80

Lys Arg Glu Lys Val Gly Glu Phe Ser Gly Val Asn Lys Glu Lys Leu
                85                  90                  95

Glu Ala Ile Ile Asn Glu Leu
            100

<210> SEQ ID NO 204
<211> LENGTH: 103
<212> TYPE: PRT
<213> ORGANISM: Artificial Sequence
<220> FEATURE:
<223> OTHER INFORMATION: Sequence homology between human TRX1 and
      Chrysochloris asistica TRX1
<220> FEATURE:
<221> NAME/KEY: MISC_FEATURE
<222> LOCATION: (3)..(3)
<223> OTHER INFORMATION: X is Gln (Q) or Glu (E).
<220> FEATURE:
<221> NAME/KEY: MISC_FEATURE
<222> LOCATION: (6)..(6)
<223> OTHER INFORMATION: X is Ser (S) or Gly (G).
<220> FEATURE:
<221> NAME/KEY: MISC_FEATURE
<222> LOCATION: (8)..(8)
<223> OTHER INFORMATION: X is Thr (T) or Glu (E).
<220> FEATURE:
<221> NAME/KEY: MISC_FEATURE
<222> LOCATION: (9)..(9)
<223> OTHER INFORMATION: X is Ala (A) or Asp (D).
<220> FEATURE:
<221> NAME/KEY: MISC_FEATURE
<222> LOCATION: (11)..(11)
<223> OTHER INFORMATION: X is Gln (Q) or His (H).
<220> FEATURE:
<221> NAME/KEY: MISC_FEATURE
<222> LOCATION: (12)..(12)
<223> OTHER INFORMATION: X is Glu (E) or Ala (A).
<220> FEATURE:
<221> NAME/KEY: MISC_FEATURE
<222> LOCATION: (15)..(15)
<223> OTHER INFORMATION: X is Asp (D) or Ser (S).
<220> FEATURE:
<221> NAME/KEY: MISC_FEATURE
<222> LOCATION: (16)..(16)
<223> OTHER INFORMATION: X is Ala (A) or Ser (S).
<220> FEATURE:
<221> NAME/KEY: misc_feature -continued

```
<222> LOCATION: (41)..(41)
<223> OTHER INFORMATION: X is Phe (F) or Tyr (Y).
<220> FEATURE:
<221> NAME/KEY: MISC_FEATURE
<222> LOCATION: (48)..(48)
<223> OTHER INFORMATION: X is Tyr (Y) or Phe (F).
<220> FEATURE:
<221> NAME/KEY: MISC_FEATURE
<222> LOCATION: (49)..(49)
<223> OTHER INFORMATION: X is Ser (S) or Gly (G).
<220> FEATURE:
<221> NAME/KEY: misc_feature
<222> LOCATION: (51)..(51)
<223> OTHER INFORMATION: X is Val (V) or Met (M).
<220> FEATURE:
<221> NAME/KEY: misc_feature
<222> LOCATION: (52)..(52)
<223> OTHER INFORMATION: X is Ile (I) or Val (V).
<220> FEATURE:
<221> NAME/KEY: MISC_FEATURE
<222> LOCATION: (74)..(74)
<223> OTHER INFORMATION: X is Phe (F) or Ile (I).
<220> FEATURE:
<221> NAME/KEY: MISC_FEATURE
<222> LOCATION: (79)..(79)
<223> OTHER INFORMATION: X is Phe (F) or Tyr (Y).
<220> FEATURE:
<221> NAME/KEY: MISC_FEATURE
<222> LOCATION: (82)..(82)
<223> OTHER INFORMATION: X is Gly (G) or Arg (R).
<220> FEATURE:
<221> NAME/KEY: MISC_FEATURE
<222> LOCATION: (83)..(83)
<223> OTHER INFORMATION: X is Gln (Q) or Glu (E).
<220> FEATURE:
<221> NAME/KEY: MISC_FEATURE
<222> LOCATION: (91)..(91)
<223> OTHER INFORMATION: X is Ala (A) or Val (V).
<220> FEATURE:
<221> NAME/KEY: MISC_FEATURE
<222> LOCATION: (99)..(99)
<223> OTHER INFORMATION: X is Thr (T) or Ile (I).

<400> SEQUENCE: 204

Val Lys Xaa Ile Glu Xaa Lys Xaa Xaa Phe Xaa Xaa Ala Leu Xaa Xaa
1               5                   10                  15

Ala Gly Asp Lys Leu Val Val Val Asp Phe Ser Ala Thr Trp Cys Gly
            20                  25                  30

Pro Cys Lys Met Ile Lys Pro Phe Xaa His Ser Leu Ser Glu Lys Xaa
        35                  40                  45

Xaa Asn Xaa Xaa Phe Leu Glu Val Asp Val Asp Cys Gln Asp Val
    50                  55                  60

Ala Ser Glu Cys Glu Val Lys Cys Met Xaa Thr Phe Gln Phe Xaa Lys
65                  70                  75                  80

Lys Xaa Xaa Lys Val Gly Glu Phe Ser Gly Xaa Asn Lys Glu Lys Leu
            85                  90                  95

Glu Ala Xaa Ile Asn Glu Leu
            100

<210> SEQ ID NO 205
<211> LENGTH: 104
<212> TYPE: PRT
<213> ORGANISM: Artificial Sequence
<220> FEATURE:
<223> OTHER INFORMATION: Chrysochloris asiatica TRX

<400> SEQUENCE: 205

Val Lys Glu Ile Glu Gly Lys Glu Asp Phe His Ala Ala Leu Ser Ser
1               5                   10                  15
```

-continued

```
Ala Gly Asp Lys Leu Val Val Val Asp Phe Ser Ala Thr Trp Cys Gly
         20                  25                  30

Pro Cys Lys Met Ile Lys Pro Phe Tyr His Ser Leu Ser Glu Lys Phe
         35                  40                  45

Gly Asn Met Val Phe Leu Glu Val Asp Val Asp Cys Gln Asp Val
 50                  55                  60

Ala Ser Glu Cys Glu Val Lys Cys Met Ile Thr Gln Phe Tyr Lys
65                   70                  75                  80

Lys Arg Glu Lys Val Gly Glu Phe Ser Gly Val Asn Lys Glu Lys Leu
             85                  90                  95

Glu Ala Ile Ile Asn Glu Leu Cys
            100
```

<210> SEQ ID NO 206
<211> LENGTH: 104
<212> TYPE: PRT
<213> ORGANISM: Artificial Sequence
<220> FEATURE:
<223> OTHER INFORMATION: Human TRX

<400> SEQUENCE: 206

```
Val Lys Gln Ile Glu Ser Lys Thr Ala Phe Gln Glu Ala Leu Asp Ala
1               5                   10                  15

Ala Gly Asp Lys Leu Val Val Val Asp Phe Ser Ala Thr Trp Cys Gly
             20                  25                  30

Pro Cys Lys Met Ile Lys Pro Phe Phe His Ser Leu Ser Glu Lys Tyr
         35                  40                  45

Ser Asn Val Ile Phe Leu Glu Val Asp Val Asp Cys Gln Asp Val
 50                  55                  60

Ala Ser Glu Cys Glu Val Lys Cys Met Pro Thr Phe Gln Phe Lys
65                   70                  75                  80

Lys Gly Gln Lys Val Gly Glu Phe Ser Gly Ala Asn Lys Glu Lys Leu
             85                  90                  95

Glu Ala Thr Ile Asn Glu Leu Val
            100
```

<210> SEQ ID NO 207
<211> LENGTH: 103
<212> TYPE: PRT
<213> ORGANISM: Artificial Sequence
<220> FEATURE:
<223> OTHER INFORMATION: M1 mutant

<400> SEQUENCE: 207

```
Val Lys Glu Ile Glu Gly Lys Glu Phe Gln Glu Ala Leu Asp Ala Ala
1               5                   10                  15

Gly Asp Lys Leu Val Val Val Asp Phe Ser Ala Thr Trp Cys Gly Pro
             20                  25                  30

Cys Lys Met Ile Lys Pro Phe Phe His Ser Leu Ser Glu Lys Tyr Ser
         35                  40                  45

Asn Val Ile Phe Leu Glu Val Asp Val Asp Cys Gln Asp Val Ala
 50                  55                  60

Ser Glu Cys Glu Val Lys Cys Met Pro Thr Phe Gln Phe Phe Lys Lys
65                   70                  75                  80

Gly Gln Lys Val Gly Glu Phe Ser Gly Ala Asn Lys Glu Lys Leu Glu
             85                  90                  95

Ala Thr Ile Asn Glu Leu Val
            100
```

```
<210> SEQ ID NO 208
<211> LENGTH: 104
<212> TYPE: PRT
<213> ORGANISM: Artificial Sequence
<220> FEATURE:
<223> OTHER INFORMATION: M2 mutant

<400> SEQUENCE: 208
```

Val Lys Gln Ile Glu Ser Lys Thr Ala Phe His Ala Ala Leu Ser Ser
1               5                   10                  15

Ala Gly Asp Lys Leu Val Val Asp Phe Ser Ala Thr Trp Cys Gly
            20                  25                  30

Pro Cys Lys Met Ile Lys Pro Phe Phe His Ser Leu Ser Glu Lys Tyr
            35                  40                  45

Ser Asn Val Ile Phe Leu Glu Val Asp Val Asp Cys Gln Asp Val
        50                  55                  60

Ala Ser Glu Cys Glu Val Lys Cys Met Pro Thr Phe Gln Phe Phe Lys
65                  70                  75                  80

Lys Gly Gln Lys Val Gly Glu Phe Ser Gly Ala Asn Lys Glu Lys Leu
                85                  90                  95

Glu Ala Thr Ile Asn Glu Leu Val
            100

```
<210> SEQ ID NO 209
<211> LENGTH: 104
<212> TYPE: PRT
<213> ORGANISM: Artificial Sequence
<220> FEATURE:
<223> OTHER INFORMATION: M3 mutant

<400> SEQUENCE: 209
```

Val Lys Gln Ile Glu Ser Lys Thr Ala Phe Gln Glu Ala Leu Asp Ala
1               5                   10                  15

Ala Gly Asp Lys Leu Val Val Val Asp Phe Ser Ala Thr Trp Cys Gly
            20                  25                  30

Pro Cys Lys Met Ile Lys Pro Phe Tyr His Ser Leu Ser Glu Lys Tyr
            35                  40                  45

Ser Asn Val Ile Phe Leu Glu Val Asp Val Asp Cys Gln Asp Val
        50                  55                  60

Ala Ser Glu Cys Glu Val Lys Cys Met Pro Thr Phe Gln Phe Phe Lys
65                  70                  75                  80

Lys Gly Gln Lys Val Gly Glu Phe Ser Gly Ala Asn Lys Glu Lys Leu
                85                  90                  95

Glu Ala Thr Ile Asn Glu Leu Val
            100

```
<210> SEQ ID NO 210
<211> LENGTH: 103
<212> TYPE: PRT
<213> ORGANISM: Artificial Sequence
<220> FEATURE:
<223> OTHER INFORMATION: M4 mutant

<400> SEQUENCE: 210
```

Val Lys Gln Ile Glu Ser Lys Thr Ala Phe Gln Glu Ala Leu Asp Ala
1               5                   10                  15

Ala Gly Asp Lys Leu Val Val Val Asp Phe Ser Ala Thr Trp Cys Gly
            20                  25                  30

-continued

Pro Cys Lys Met Ile Lys Pro Phe Phe His Ser Leu Ser Glu Lys Phe
        35                  40                  45

Gly Asn Met Val Leu Glu Val Asp Val Asp Asp Cys Gln Asp Val Ala
 50                  55                  60

Ser Glu Cys Glu Val Lys Cys Met Pro Thr Phe Gln Phe Phe Lys Lys
65                   70                  75                  80

Gly Gln Lys Val Gly Glu Phe Ser Gly Ala Asn Lys Glu Lys Leu Glu
                85                  90                  95

Ala Thr Ile Asn Glu Leu Val
            100

<210> SEQ ID NO 211
<211> LENGTH: 104
<212> TYPE: PRT
<213> ORGANISM: Artificial Sequence
<220> FEATURE:
<223> OTHER INFORMATION: M5 mutant

<400> SEQUENCE: 211

Val Lys Gln Ile Glu Ser Lys Thr Ala Phe Gln Glu Ala Leu Asp Ala
 1               5                  10                  15

Ala Gly Asp Lys Leu Val Val Val Asp Phe Ser Ala Thr Trp Cys Gly
                20                  25                  30

Pro Cys Lys Met Ile Lys Pro Phe Phe His Ser Leu Ser Glu Lys Tyr
        35                  40                  45

Ser Asn Val Ile Phe Leu Glu Val Asp Val Asp Asp Cys Gln Asp Val
 50                  55                  60

Ala Ser Glu Cys Glu Val Lys Cys Met Ile Thr Phe Gln Phe Phe Lys
65                   70                  75                  80

Lys Gly Gln Lys Val Gly Glu Phe Ser Gly Ala Asn Lys Glu Lys Leu
                85                  90                  95

Glu Ala Thr Ile Asn Glu Leu Val
            100

<210> SEQ ID NO 212
<211> LENGTH: 104
<212> TYPE: PRT
<213> ORGANISM: Artificial Sequence
<220> FEATURE:
<223> OTHER INFORMATION: M6 mutant

<400> SEQUENCE: 212

Val Lys Gln Ile Glu Ser Lys Thr Ala Phe Gln Glu Ala Leu Asp Ala
 1               5                  10                  15

Ala Gly Asp Lys Leu Val Val Val Asp Phe Ser Ala Thr Trp Cys Gly
                20                  25                  30

Pro Cys Lys Met Ile Lys Pro Phe Phe His Ser Leu Ser Glu Lys Tyr
        35                  40                  45

Ser Asn Val Ile Phe Leu Glu Val Asp Val Asp Asp Cys Gln Asp Val
 50                  55                  60

Ala Ser Glu Cys Glu Val Lys Cys Met Pro Thr Phe Gln Phe Tyr Lys
65                   70                  75                  80

Lys Arg Glu Lys Val Gly Glu Phe Ser Gly Ala Asn Lys Glu Lys Leu
                85                  90                  95

Glu Ala Thr Ile Asn Glu Leu Val
            100

<210> SEQ ID NO 213

```
<211> LENGTH: 105
<212> TYPE: PRT
<213> ORGANISM: Artificial Sequence
<220> FEATURE:
<223> OTHER INFORMATION: M7 mutant

<400> SEQUENCE: 213

Val Lys Gln Ile Glu Ser Lys Thr Ala Phe Gln Glu Ala Leu Asp Ala
1               5                   10                  15

Ala Gly Asp Lys Leu Val Val Val Asp Phe Ser Ala Thr Trp Cys Gly
                20                  25                  30

Pro Cys Lys Met Ile Lys Pro Phe Phe His Ser Leu Ser Glu Lys Tyr
            35                  40                  45

Ser Asn Val Ile Phe Leu Glu Val Asp Val Asp Asp Cys Gln Asp Val
        50                  55                  60

Ala Ser Glu Cys Glu Val Lys Cys Met Pro Thr Phe Gln Phe Phe Lys
65                  70                  75                  80

Lys Gly Gln Lys Val Gly Glu Phe Ser Ser Ala Asn Lys Glu Lys Leu
                85                  90                  95

Glu Ala Thr Ile Asn Glu Leu Val Cys
            100                 105

<210> SEQ ID NO 214
<211> LENGTH: 104
<212> TYPE: PRT
<213> ORGANISM: Artificial Sequence
<220> FEATURE:
<223> OTHER INFORMATION: M8 mutant

<400> SEQUENCE: 214

Val Lys Gln Ile Glu Ser Lys Thr Ala Phe Gln Glu Ala Leu Asp Ala
1               5                   10                  15

Ala Gly Asp Lys Leu Val Val Val Asp Phe Ser Ala Thr Trp Cys Gly
                20                  25                  30

Pro Cys Lys Met Ile Lys Pro Phe Phe His Ser Leu Ser Glu Lys Tyr
            35                  40                  45

Ser Asn Val Ile Phe Leu Glu Val Asp Val Asp Asp Cys Gln Asp Val
        50                  55                  60

Ala Ser Glu Cys Glu Val Lys Cys Met Pro Thr Phe Gln Phe Phe Lys
65                  70                  75                  80

Lys Gly Gln Lys Val Gly Glu Phe Ser Gly Ala Asn Lys Glu Lys Leu
                85                  90                  95

Glu Ala Ile Ile Asn Glu Leu Cys
            100

<210> SEQ ID NO 215
<211> LENGTH: 18
<212> TYPE: DNA
<213> ORGANISM: Artificial Sequence
<220> FEATURE:
<223> OTHER INFORMATION: Xba1 Restriction Site

<400> SEQUENCE: 215
attactttcg atagatct                                               18
```